US008658350B2

(12) United States Patent
Lewinsohn et al.

(10) Patent No.: US 8,658,350 B2
(45) Date of Patent: Feb. 25, 2014

(54) **METHODS FOR DETECTING *MYCOBACTERIUM TUBERCULOSIS* DISEASE**

(75) Inventors: Deborah A. Lewinsohn, Portland, OR (US); David M. Lewinsohn, Portland, OR (US)

(73) Assignees: Oregon Health & Science University, Portland, OR (US); The United States of America as represented by the Department of Veterans Affairs, Washington, DC (US)

( * ) Notice: Subject to any disclaimer, the term of this patent is extended or adjusted under 35 U.S.C. 154(b) by 63 days.

(21) Appl. No.: 13/119,938

(22) PCT Filed: Sep. 22, 2009

(86) PCT No.: PCT/US2009/057891
§ 371 (c)(1), (2), (4) Date: Mar. 18, 2011

(87) PCT Pub. No.: WO2010/034007
PCT Pub. Date: Mar. 25, 2010

(65) Prior Publication Data
US 2011/0183342 A1 Jul. 28, 2011

Related U.S. Application Data

(60) Provisional application No. 61/099,162, filed on Sep. 22, 2008.

(51) Int. Cl.
*C12Q 1/00* (2006.01)
*C12Q 1/68* (2006.01)
*G01N 33/53* (2006.01)
*G01N 33/567* (2006.01)

(52) U.S. Cl.
USPC .................. 435/4; 435/6.1; 435/7.1; 435/7.2

(58) Field of Classification Search
None
See application file for complete search history.

(56) References Cited

U.S. PATENT DOCUMENTS 7,572,597 B2 * 8/2009 Lalvani et al. ............... 435/7.32
2002/0131976 A1 9/2002 Lalvani et al.
2004/0141985 A1 7/2004 Lalvani et al.

FOREIGN PATENT DOCUMENTS

WO     WO 01/62893 A2     8/2001
WO     2004/005925     *     1/2004
WO     WO 2007/106536 A2     9/2007

OTHER PUBLICATIONS

International Search Report from parent PCT Application No. PCT/US2009/057891, 7 pages (mailed May 10, 2010).
Lewinsohn et al., "Immunodominant Tuberculosis CD8 Antigens Preferentially Restricted by HLA-B," *PLOS Pathogens*, 3(9):1240-1249, 2007.
Written Opinion from parent PCT Application No. PCT/US2009/057891, 8 pages (May 10, 2010).
Caccamo et al., "Analysis of Mycobacterium tuberculosis-specific CD8 T-cells in patients with active tuberculosis and in individuals with latent infection," *Public Libary of Science* 4(5):E5528-1 (May 13, 2009).
European Examination Report from corresponding EPC Application No. 11 169 004.6, 6 pages (mailed May 21, 2013).
Jacobsen et al., "Clonal expansion of CD8+ effector T cells in childhood tuberculosis," *Journal of Immunology* 179(2): 1331-1339 (Jul. 1, 2007).
Lancioni et al., "CD8+ cells provide an immunologic signature of tuberculosis in young children," *American Journal of Respiratory and Critical Care Medicine* 185(2): 206-212 (Jan. 15, 2012).
Marais et al., "Childhood Pulmonary Tuberculosis," *American Journal of Respiratory and Critical Care Medicine* 173(10):1078-1090 (May 15, 2006).

* cited by examiner

*Primary Examiner* — Albert Navarro
(74) *Attorney, Agent, or Firm* — Klarquist Sparkman, LLP

(57) ABSTRACT

Methods for detecting an infection with *Mycobacterium tuberculosis* (Mtb) in a subject are disclosed, wherein the subject is a child, a subject with a latent *Mycobacterium tuberculosis* infection. Method are also disclose for detecting an extra-pulmonary *Mycobacterium tuberculosis* infection in a subject. The methods include detecting the presence of $CD8^+$ T cells that specifically recognize an Mtb polypeptide. The methods include in vitro assays for detecting the presence of $CD8^+$ T cells in a biological sample.

26 Claims, 11 Drawing Sheets

Identification of Antigen

Media  ESAT-6  CFP10  Mtb8.4  Mtb9.8  Ag85p1  Ag85p2  Mtb39p1  Mtb39p2  MSL  19kDa  PHA

Identification of 15mer Peptide 1-15  5-19  9-23  13-27  17-31  21-35  25-39  29-43  33-47  37-51  41-55  45-59

49-63  53-67  57-71  61-75  65-79  69-83  73-87  77-91  81-95  85-99  PHA  Media

Identification of Minimal Epitopes 2-10  3-11  4-12  5-13  Media  PHA 1-15  2-12  3-13  1-10  2-11  3-12

Identification of Restricting Allele

Control

Autologous — A2301 A24 B3701 B4501 C0602 C1601

IHW 9058 — A0201 B4501 C1601

NACR 0371 — A0201 A0301 B3701 B4402 C0501 C0602

D433 — A2402 A2901 B4002 B4403 C0202 C1601

D14 — A3 A24 B62 B18 C0304 C1203

IHW 9029 — A2301 B1401 C0802

D451 — A0301 A3001 B0702 B1301 C0602 C0702

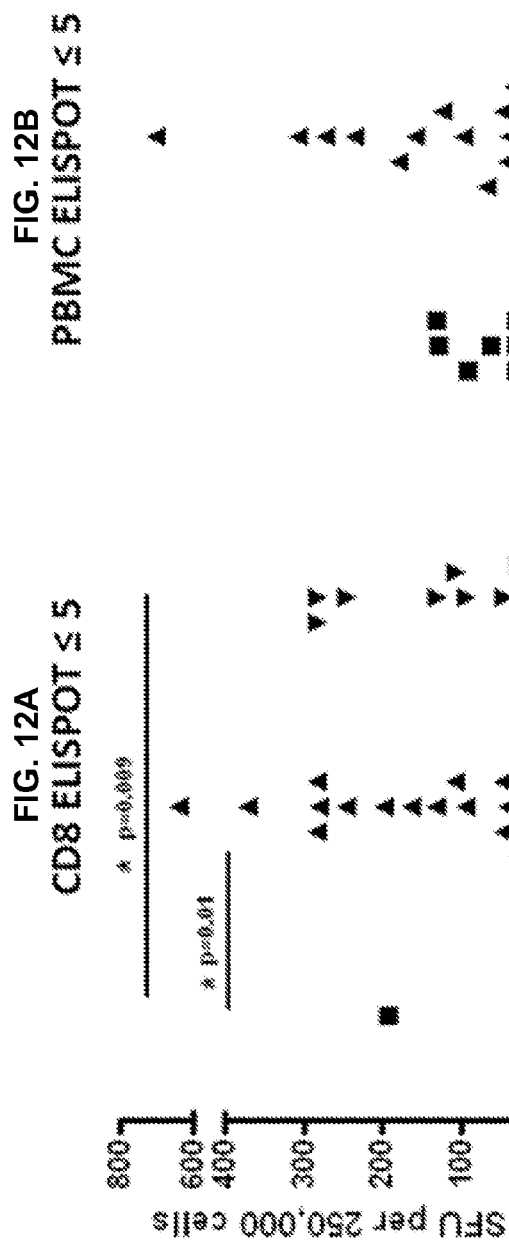
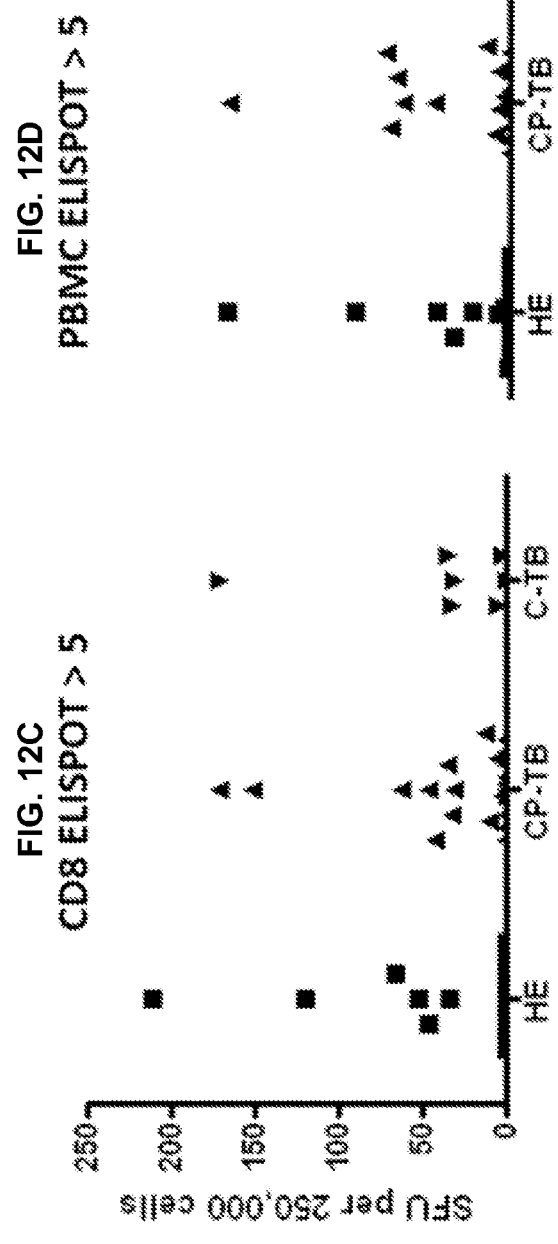
FIG. 12A CD8 ELISPOT ≤ 5
FIG. 12B PBMC ELISPOT ≤ 5
FIG. 12C CD8 ELISPOT > 5
FIG. 12D PBMC ELISPOT > 5

METHODS FOR DETECTING *MYCOBACTERIUM TUBERCULOSIS* DISEASE

CROSS REFERENCE TO RELATED APPLICATIONS

This is the U.S. National Stage of International Application No. PCT/US2009/057891, filed Sep. 22, 2009, which was published in English under PCT Article 21(2), which in turn claims the benefit of U.S. Provisional Application No. 61/099,162, filed Sep. 22, 2008, which is-incorporated by reference herein by reference in its entirety.

STATEMENT OF GOVERNMENT SUPPORT

This invention was made with United States government support pursuant to Grant No. AI054474 and AI070022 from the National Institutes of Heath; the United States government has certain rights in the invention. This invention was also made with support from the Department of Veterans Affairs.

FIELD

This application relates to the field of diagnosis, specifically to methods for detecting a *Mycobacterium tuberculsosis* (Mtb) infection in a subject, specifically in children and/or for the diagnosis of a latent infection.

RELATED SUBJECT MATTER

This application is related to the subject matter of U.S. Provisional Application No. 60/782,364, filed Mar. 14, 2006, and PCT Application No. PCT/US2007/006534, filed Mar. 14, 2007, which are both incorporated herein by reference.

BACKGROUND

*Mycobacteria* are a genus of aerobic intracellular bacterial organisms that, upon infection of a host, survive within endosomal compartments of monocytes and macrophages. Human mycobacterial diseases include tuberculosis (caused by *M. tuberculosis*), leprosy (caused by *M. leprae*), Bairnsdale ulcers (caused by *M. ulcerans*), and various infections caused by *M. marinum, M. kansasii, M. scrofulaceum, M. szulgai, M. xenopi, M. fortuitum, M. chelonei, M. haemophilum* and *M. intracellulare* (see Wolinsky, E., Chapter 37 in Microbiology: Including Immunology and Molecular Genetics, 3rd Ed., Harper & Row, Philadelphia, 1980).

One third of the world's population harbors *M. tuberculosis* and is at risk for developing tuberculosis (TB). Young children bear the burden of developing tuberculosis (TB) disproportionately. Once infected, children are not only more susceptible to TB than adults, but also are more likely to develop a severe form of the disease. Specifically, following infection more than 90% of immunocompetent adults will establish an asymptomatic, latent TB infection (LTBI), which carries a 5-10% life-time risk of reactivation disease. Whereas, in the majority of young infants, a primary Mtb infection will advance to active TB, and then in a substantial proportion of those with active TB, the disease will progress to a more severe form (e.g., military TB). In addition to an increased susceptibility to TB, prompt diagnosis in children is complicated by the fact that children with progressive primary infections seldom present with a positive sputum acid-fast *bacillus* smear, which is commonly seen in adult pulmonary reactivation disease. Early detection is essential since progression of the disease occurs during the period of diagnostic delay.

In immunocompromised patients, tuberculosis is increasing at a nearly logarithmic rate, and multidrug resistant strains are appearing. In addition, Mycobacterial strains which were previously considered to be nonpathogenic strains (e.g., *M. avium*) have now become major killers of immunosuppressed AIDS patients. Moreover, current Mycobacterial vaccines are either inadequate (such as the BCG vaccine for *M. tuberculosis*) or unavailable (such as for *M. leprae*) (Kaufmann, S., Microbiol. Sci. 4:324-328, 1987; U.S. Congress, Office of Technology Assessment, The Continuing Challenge of Tuberculosis, pp. 62-67, OTA-H-574, U.S. Government Printing Office, Washington, D.C., 1993).

Inhibiting the spread of tuberculosis requires effective vaccination and accurate, early diagnosis of the disease. Currently, vaccination with live bacteria is the most efficient method for inducing protective immunity. The most common *Mycobacterium* employed for this purpose is *Bacillus* Calmette-Guerin (BCG), an avirulent strain of *Mycobacterium bovis*. However, the safety and efficacy of BCG is a source of controversy and some countries, such as the United States, do not vaccinate the general public.

Diagnosis of tuberculosis is commonly achieved using a skin test, which involves intradermal exposure to tuberculin PPD (protein-purified derivative). Antigen-specific T cell responses result in measurable induration at the injection site by 48 to 72 hours after injection, which indicates exposure to Mycobacterial antigens. However, the sensitivity and specificity of this test are not ideal; individuals vaccinated with BCG cannot be distinguished from infected individuals. In addition, it is not particularly effective in diagnosing children or LTBI. Accordingly, there is a need in the art for improved diagnostic methods for detecting tuberculosis, specifically for detecting LTBI and for diagnosing TB infections in children.

SUMMARY

Methods for diagnosing an infection with *Mycobacterium tuberculosis* (Mtb) are disclosed herein. In some embodiments, the methods are of use for detecting a latent tuberculosis infection (LTBI) and/or for detecting Mtb infection in children. In additional embodiments, the methods are of use for detecting an extra-pulmonary infection. The methods including isolating $CD8^+$ T cells and detecting CD8+ T cells that specifically respond to an Mtb polypeptide of interest. The methods can include detecting the expression of a cytokine, such as, but not limited to interferon (IFN)-γ. In some embodiments, the methods and utilize ESAT-6 and/or CFP-10 polypeptides, such as but not limited to detecting tuberculosis disease in children.

In several embodiments, methods are provided for detecting *Mycobacterium tuberculosis* in a subject. These methods can be used to detect tuberculosis disease, including pulmonary tuberculosis disease and/or extra-pulmonary tuberculosis disease. These methods include contacting a biological sample from the subject comprising T cells, such as $CD8^+$ T cells, with one or more *Mycobacterium* polypeptides, or an antigen presenting cell presenting the one or more *Mycobacterium* polypeptides. The one or more *Mycobacterium* polypeptides can include ESAT9 and CFP10, or an antigenic epitope thereof. The one or more *Mycobacterium* polypeptides can also include an amino acid sequence set forth as (a) one of the amino acid sequences set forth as SEQ ID NO: 1, SEQ ID NO: 2, SEQ ID NO: 3, SEQ ID NO: 4, SEQ ID NO:

5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 39 or SEQ ID NO: 61; or (b) at least nine to twenty consecutive amino acids of at least one of the amino acid sequences set forth as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 7, SEQ ID NO: 8, SEQ ID NO: 9, SEQ ID NO: 10, SEQ ID NO: 11, SEQ ID NO: 12, SEQ ID NO: 39 or SEQ ID NO: 61, wherein the nine to twenty consecutive amino acids specifically bind major histocompatibility complex (MHC) class I; or one of the amino acid sequences set forth as SEQ ID NOs: 39-83. It is determined whether the T cells specifically recognize the *Mycobacterium* polypeptide.

In additional embodiments, the methods also include administering to the subject an effective amount of a *Mycobacterium* polypeptide into the skin, subcutaneously or intradermally. The *Mycobacterium* polypeptide can be ESAT6 or CFP10, or an antigenic epitope thereof. The *Mycobacterium* polypeptide includes an amino acid sequence set forth as (a) one of the amino acid sequences set forth as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 31 or SEQ ID NO: 61; or (b) at least nine to twenty consecutive amino acids of at least one of the amino acid sequences set forth as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 7, SEQ ID NO: 8, SEQ ID NO: 9, SEQ ID NO: 10, SEQ ID NO: 11, SEQ ID NO: 12, SEQ ID NO: 39 or SEQ ID NO: 61, wherein the nine to twenty consecutive amino acids specifically bind major histocompatibility complex (MHC) class I, or one of the amino acid sequences set forth as SEQ ID NO: 39-83. The presence of T cells that specifically recognize the *Mycobacterium* polypeptide are detected in the subject.

The methods can also include detecting a delayed type hypersensitivity reaction in a subject and/or can include detecting specific Mtb polypeptides and polynucleotides. The disclosed assays can be used individually or in combination. The *Mycobacterium tuberculosis* infection can be a latent or active infection.

Additionally, reagents and kits for the detection of a *Mycobacterium* infection in a subject are described.

The foregoing and other features and advantages will become more apparent from the following detailed description of several embodiments, which proceeds with reference to the accompanying figures.

BRIEF DESCRIPTION OF THE FIGURES

FIGS. 12a-12d are a set of graphs wherein CD8 ELISPOT results are depicted as spot forming units (SFU) above the predetermined cut off for children ≤5 (12A) and for children >5 (12C). PBMC ELISPOT results for children ≤5 and >5 are shown in (12B) and (12D). Ugandan children ≤5 with CP-TB or C-TB had a significant and robust response by CD8 T cell ELISPOT whereas healthy exposed children did not exhibit this response (12A). By comparison, in HE contacts there is a measurable response by PBMC ELISPOT and this response did not differ in magnitude from the children with CP-TB or C-TB (12B). When analyzed categorically using the pre-defined cut-off, children ≤5 with confirmed or probable TB were more likely to have a positive CD8 ELISPOT (p=0.01) whereas there was no categorical association with the PBMC ELISPOT and clinical subgroup. For children >5, due to the small number of children in the C-TB group for the CD8 (n=7) and for the PBMC (n=5), magnitude and categorical statistical comparisons were not performed, however SFU are shown for descriptive purposes. For the >5 age group, comparing the HE, with the CP-TB group, there was no difference in magnitude of the SFU or by categorical analysis (12C and 12D). Statistical analysis for the magnitude utilized wilxocon rank sum test, two sided; for the categorical analysis, chi-squared analysis was performed.

SEQUENCE LISTING

Figure 1:
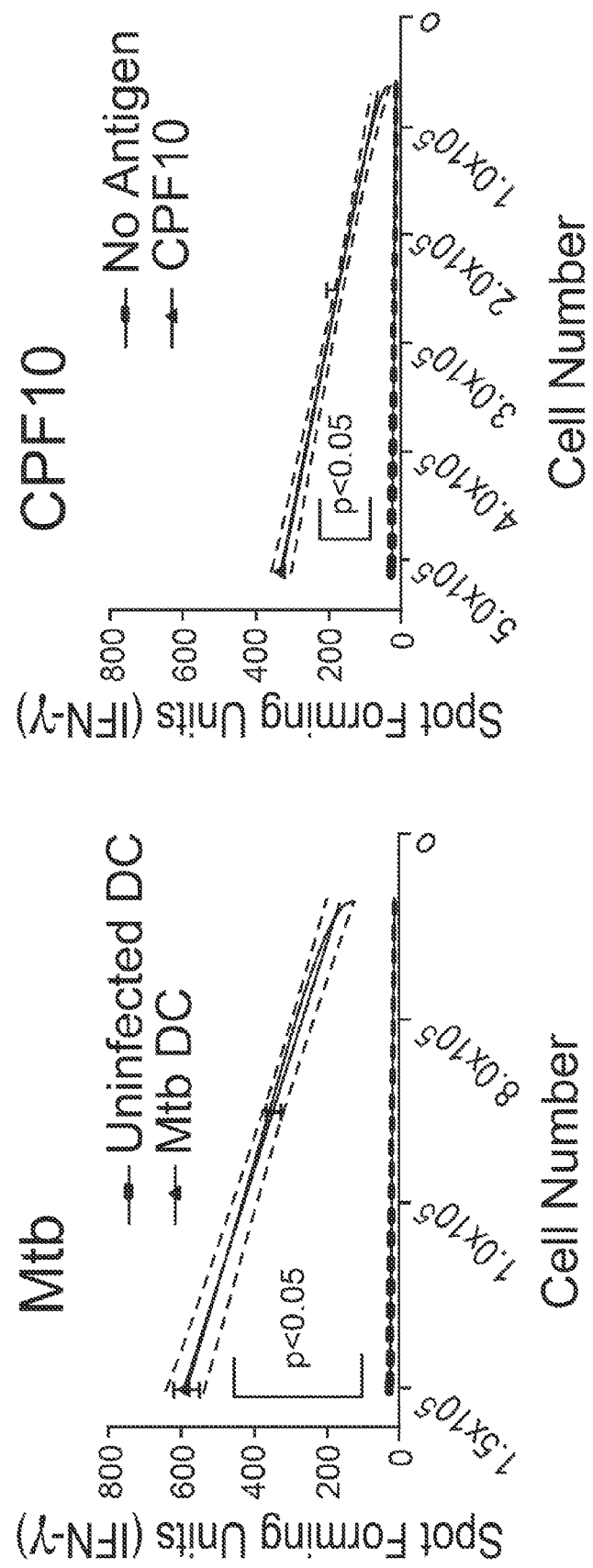
FIG. 1 is two graphs showing the determination of human effector cell frequencies ex vivo using the IFN-γ ELISPOT assay. Magnetic bead-purified CD8$^+$ T cells were cultured with DC (20,000/well) either infected with Mtb (H37Rv, MOI=50) or pulsed with peptide pool representing CFP10 (5 μg/ml each peptide; 15-mers overlap 11 aa) in an IFN-γ ELISPOT assay. Each responding T cell population was tested in duplicate at four different cell concentrations. To determine the effector cell frequency of antigen-specific T cells, the average number of spots per well for each duplicate was plotted against the number of responder cells per well. Linear regression analysis was used to determine the slope of the line, which represents the frequency of antigen-specific T cells. The assay was considered positive (reflecting the presence of a primed T cell response), if the binomial probability for the number of spots was significantly different by experimental and control assays.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The sequence listing is submitted as an ASCII text file, created on Mar. 18, 2011, 96.0 KB, which is incorporated by reference herein. In the accompanying sequence listing:

SEQ ID NOs: 1-12 are the amino acid sequence of Mtb polypeptides.

SEQ ID NOs: 13-14 are amino acids of Mtb peptides.

SEQ ID NOs: 15-25 are the nucleic acid sequences of polynucleotides encoding the Mtb polypeptides.

SEQ ID NOs: 26-38 are the amino acid sequences of specific Mtb epitopes.

SEQ ID NO: 39-83 are the amino acid sequence of specific CFP10 and ESAT6 Mtb polypeptides of use.

SEQ ID NO: 84 is the amino acid sequence of an exemplary linker.

DETAILED DESCRIPTION

Methods for detecting an infection with *Mycobacterium tuberculosis* in a subject are disclosed. The subject is a child or a subject with LTBI. The methods include detecting the presence of T cells, specifically CD8+ T cells, that specifically recognize a *Mycobacterium tuberculosis* (Mtb) polypeptide. The methods include in vitro assays for detecting the presence of reactive CD8+ T cells in a biological sample, and can also include in vivo assays that detect a delayed type hypersensitivity reaction. These methods are of use to detect tuberculosis disease in children, including pulmonary tuberculosis disease and extra-pulmonary tuberculosis disease. These methods are also of use to detect extra-pulmonary tuberculosis disease in adults with a latent tuberculosis infection.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Adjuvant:

A vehicle used to enhance antigenicity. Adjuvants include a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants (for example see U.S. Pat. No. 6,194,388; U.S. Pat. No. 6,207,646; U.S. Pat. No. 6,214,806; U.S. Pat. No. 6,218,371; U.S. Pat. No. 6,239,116; U.S. Pat. No. 6,339,068; U.S. Pat. No. 6,406,705; and U.S. Pat. No. 6,429,199). Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L and 41 BBL Amplification:

Of a nucleic acid molecule (e.g., a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Antigen:

A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and 2-dimensional nuclear magnetic resonance.

An antigen can be a tissue-specific antigen, or a disease-specific antigen. These terms are not exclusive, as a tissue-specific antigen can also be a disease specific antigen. A tissue-specific antigen is expressed in a limited number of tissues, such as a single tissue. A tissue specific antigen may be expressed by more than one tissue, such as, but not limited to, an antigen that is expressed in more than one reproductive tissue, such as in both prostate and uterine tissue. A disease-specific antigen is expressed coincidentally with a disease process. Specific non-limiting examples of a disease-specific antigen are an antigen whose expression correlates with, or is predictive of, tuberculosis. A disease-specific antigen can be an antigen recognized by T cells or B cells. An Mtb-specific antigen is specific for Mtb.

Antibody:

Immunoglobulin molecules and immunologically active portions of immunoglobulin molecules, i.e., molecules that contain an antigen binding site that specifically binds (immunoreacts with) an antigen, such as an Mtb polypeptide.

A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the $V_L$, $V_H$, $C_L$ and $C_{H1}$ domains; (ii) an $F_d$ fragment consisting of the $V_H$ and $C_{H1}$ domains; (iii) an Fv fragment consisting of the $V_L$ and $V_H$ domains of a single arm of an antibody, (iv) a dAb fragment (Ward et al., Nature 341:544-546, 1989) which consists of a $V_H$ domain; (v) an isolated complementarity determining region (CDR); and (vi) a $F(ab')_2$ fragment, a bivalent fragment comprising two Fab fragments linked by a disulfide bridge at the hinge region.

Immunoglobulins and certain variants thereof are known and many have been prepared in recombinant cell culture (e.g., see U.S. Pat. No. 4,745,055; U.S. Pat. No. 4,444,487; WO 88/03565; EP 256,654; EP 120,694; EP 125,023; Faoulkner et al., Nature 298:286, 1982; Morrison, J. Immunol. 123:793, 1979; Morrison et al., Ann Rev. Immunol 2:239, 1984).

Animal:

Living multi-cellular vertebrate organisms, a category that includes, for example, mammals and birds. The term mammal includes both human and non-human mammals. Similarly, the term "subject" includes both human and veterinary subjects. A "child" is a human subject less than about 18 years of age. In some embodiments, a "young child" is a human subject of about 1 to about 5 years of age. An "older child" is a human subject of about 6 to about 12 years of age. An "infant" is a human subject less than one year of age. A "teenager" is a human subject of about 13 to about 18 years of age. A "prepubescent subject" has not undergone puberty, and in some examples is a human subject less than about 11 years of age.

Antigen Presenting Cell (APC):

A cell that can present an antigen to T cell, such that the T cells are activated. Dendritic cells are the principle antigen presenting cells (APCs) involved in primary immune responses. Their major function is to obtain antigen in tissues, migrate to lymphoid organs and present the antigen in order to activate T cells.

When an appropriate maturational cue is received, dendritic cells are signaled to undergo rapid morphological and physiological changes that facilitate the initiation and development of immune responses. Among these are the up-regulation of molecules involved in antigen presentation; production of pro-inflammatory cytokines, including IL-12, key to the generation of Th1 responses; and secretion of chemokines that help to drive differentiation, expansion, and migration of surrounding naive Th cells. Collectively, these up-regulated molecules facilitate the ability of dendritic cells to coordinate the activation and effector function of other surrounding lymphocytes that ultimately provide protection for the host.

cDNA (Complementary DNA):

A piece of DNA lacking internal, non-coding segments (introns) and regulatory sequences that determine transcription. cDNA is synthesized in the laboratory by reverse transcription from messenger RNA extracted from cells.

CD4:

Cluster of differentiation factor 4, a T cell surface protein that mediates interaction with the MHC Class II molecule. CD4 also serves as the primary receptor site for HIV on T cells during HIV infection. Cells that express CD4 are often helper T cells.

CD8:

Cluster of differentiation factor 8, a T cell surface protein that mediates interaction with the MHC Class I molecule. Cells that express CD8 are often cytotoxic T cells. "CD8+ T cell mediated immunity" is an immune response implemented by presentation of antigens to CD8+ T cells.

cDNA (Complementary DNA):

A piece of DNA lacking internal, non-coding segments (introns) and regulatory sequences that determine transcription. cDNA is synthesized in the laboratory by reverse transcription from messenger RNA extracted from cells.

Conservative Variants:

"Conservative" amino acid substitutions are those substitutions that do not substantially affect or decrease an activity or antigenicity of the *Mycobacterium* polypeptide. Specific, non-limiting examples of a conservative substitution include the following examples:

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the substituted polypeptide also immunoreact with the unsubstituted polypeptide, or that an immune response can be generated against the substituted polypeptide that is similar to the immune response against and unsubstituted polypeptide, such a *Mycobacterium* antigen. Thus, in one embodiment, non-conservative substitutions are those that reduce an activity or antigenicity.

Consists Essentially of/Consists of:

With regard to a polypeptide, a polypeptide that consists essentially of a specified amino acid sequence if it does not include any additional amino acid residues. However, the polypeptide can include additional non-peptide components, such as labels (for example, fluorescent, radioactive, or solid particle labels), sugars or lipids. A polypeptide that consists of a specified amino acid sequence does not include any additional amino acid residues, nor does it include additional non-peptide components, such as lipids, sugars or labels.

Contacting:

The process of incubating one agent in the presence of another. Thus, when a cell is contacted with an agent, the cell is incubated with the agent for a sufficient period of time for the agent and the cell to interact.

Costimulatory Molecule:

Although engagement of the TCR with peptide-MHC delivers one signal to the T cell, this signal alone can be insufficient to activate the T cell. Costimulatory molecules are molecules that, when bound to their ligand, deliver a second signal required for the T cell to become activated. The most well-known costimulatory molecule on the T cell is CD28, which binds to either B7-1 (also called CD80) or B7-2 (also known as CD86). An additional costimulatory molecule is B7-3. Accessory molecules that also provide a second signal for the activation of T cells include intracellular adhesion molecule (ICAM-1 and ICAM-2), leukocyte function associated antigen (LFA-1, LFA-2 and LFA-3). Integrins and tumor necrosis factor (TNF) superfamily members can also serve as co-stimulatory molecules.

Cytokine:

Proteins made by cells that affect the behavior of other cells, such as lymphocytes. In one embodiment, a cytokine is a chemokine, a molecule that affects cellular trafficking. Specific, non-limiting examples of cytokines include the interleukins (IL-2, IL-4, IL-6, IL-10, IL-21, etc.), and interferon (IFN)-γ.

Degenerate Variant:

A polynucleotide encoding an epitope of an Mtb polypeptide that includes a sequence that is degenerate as a result of the genetic code. There are 20 natural amino acids, most of which are specified by more than one codon. Therefore, all degenerate nucleotide sequences are included in this disclosure as long as the amino acid sequence of the Mtb polypeptide encoded by the nucleotide sequence is unchanged.

Dendritic Cell (DC):

Dendritic cells are the principle antigen presenting cells (APCs) involved in primary immune responses. Dendritic cells include plasmacytoid dendritic cells and myeloid dendritic cells. Their major function is to obtain antigen in tissues, migrate to lymphoid organs and present the antigen in order to activate T cells. Immature dendritic cells originate in the bone marrow and reside in the periphery as immature cells.

Diagnostic:

Identifying the presence or nature of a pathologic condition, such as, but not limited to, tuberculosis. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" means predicting the probability of development (for example, severity) of a pathologic condition, such as tuberculosis.

Displaying:

The process of localizing a peptide:antigen complex, or a peptide, on the outer surface of a cell where the peptide: antigen complex or peptide is accessible to a second cell, molecules displayed by a second cell, or soluble factors. A peptide, or a peptide:antigen complex, is "displayed" by a cell when it is present on the outer surface of the cell and is accessible to a second cell, to molecules displayed by the second cell, or to soluble factors.

Epitope:

An antigenic determinant. These are particular chemical groups or peptide sequences on a molecule that are antigenic, i.e. that elicit a specific immune response. An antibody specifically binds a particular antigenic epitope on a polypeptide, such a *Mycobacterium* polypeptide.

Expression Control Sequences:

Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences. In one embodiment, the promoter is a cytomegalovirus promoter.

Fractionating:

Subjecting a sample to conditions or procedures which separate the components of the sample based on physical or chemical properties such as, but not limited to, size, charge, solubility, or composition. Example of fractionation procedures include, but are not limited to, selective precipitation, organic extraction, size exclusion dialysis or chromatography, such as ion exchange chromatography. In one embodiment, a fraction is a soluble extract or an organic extract of an organism, such as a *Mycobacterium*.

Functionally Equivalent:

Sequence alterations, such as in an epitope of an antigen, that yield the same results as described herein. Such sequence alterations can include, but are not limited to, conservative substitutions, deletions, mutations, frameshifts, and insertions.

Heterologous:

Originating from separate genetic sources or species. A polypeptide that is heterologous to an Mtb polypeptide originates from a nucleic acid that does not encode the Mtb polypeptide. In one specific, non-limiting example, a polypeptide comprising nine consecutive amino acids from an Mtb polypeptide, or at most 20 consecutive amino acids from the Mtb polypeptide, and a heterologous amino acid sequence includes a β-galactosidase, a maltose binding protein, and albumin, hepatitis B surface antigen, or an immunoglobulin amino acid sequence. Generally, an antibody that specifically binds to a protein of interest will not specifically bind to a heterologous protein.

Host Cells:

Cells in which a vector can be propagated and its DNA expressed. The cell may be prokaryotic or eukaryotic. The cell can be mammalian, such as a human cell. The term also includes any progeny of the subject host cell. It is understood that all progeny may not be identical to the parental cell since there may be mutations that occur during replication. However, such progeny are included when the term "host cell" is used.

Human Leukocyte Antigen (HLA):

A genetic designation of the human major histocompatibility complex (MHC). Individual loci are designated by uppercase letters, as in HLA-E, and alleles are designated by numbers, as in HLA-A*0201. The three main MHC class I genes are called HLA-A, HLA-B, and HLA-C. However, there are many genes that encode In microglobulin-associated cell surface molecules that are linked to the MHC class I genes. The expression of these genes is variable, both in the tissue distribution and the amount expressed on cells; these genes have been termed the MHC class IB genes.

Immune Response:

A response of a cell of the immune system, such as a B cell, natural killer cell, or a T cell, to a stimulus. In one embodiment, the response is specific for a particular antigen (an "antigen-specific response"). In one embodiment, an immune response is a T cell response, such as a Th1, Th2, or Th3 response. In another embodiment, an immune response is a response of a suppressor T cell.

Immunogenic Peptide:

A peptide which comprises an allele-specific motif or other sequence such that the peptide will bind an MHC molecule and induce a T cell response, such as a $CD8^+$ T cell response, or a B cell response (such as antibody production) against the antigen from which the immunogenic peptide is derived. In additional example, immunogenic peptide induce cytokine production from $CD8^+$ T cells.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide.

Immunogenic peptides can also be identified by measuring their binding to a specific MHC protein and by their ability to stimulate CD8+ T cells when presented in the context of the MHC protein. In one example, an immunogenic "Mtb peptide" is a series of contiguous amino acid residues from the Mtb protein generally between 9 and 20 amino acids in length, such as about 8 to 11 residues in length. Specific immunogenic polypeptides are disclosed herein that are 9 or 10 amino acid residues in length, or at most 12 amino acids in length.

Generally, immunogenic Mtb polypeptides can be used to induce an immune response in a subject, such as a B cell response or a T cell response. In one example, an immunogenic Mtb polypeptide, when bound to a Major Histocompatibility Complex Class I molecule, activates CD8+ T cells, such as cytotoxic T lymphocytes (CTLs) against Mtb. Induction of CTLs using synthetic peptides and CTL cytotoxicity assays known in the art, see U.S. Pat. No. 5,662,907, which is incorporated herein by reference. In one example, an immunogenic peptide includes an allele-specific motif or other sequence such that the peptide will bind an MHC molecule and induce a CD8+ response against the antigen from which the immunogenic peptide is derived. A CD8+ T cell that specifically recognizes an Mtb polypeptide is activated, proliferates, and/or secretes cytokines in response to that specific polypeptide, and not to other, non-related polypeptides.

Immunogenic Composition:

A composition comprising an immunogenic Mtb polypeptide or a nucleic acid encoding the immunogenic Mtb polypeptide that induces a measurable T response against Mtb, such as a CD8+ T cell response, or induces a measurable B cell response (such as production of antibodies that specifically bind an Mtb polypeptide). For in vitro use, the immunogenic composition can consist of the isolated nucleic acid, vector including the nucleic acid/or immunogenic peptide. For in vivo use, the immunogenic composition will typically comprise the nucleic acid, vector including the nucleic acid, and or immunogenic polypeptide, in pharmaceutically acceptable carriers, and/or other agents. An immunogenic composition can optionally include an adjuvant, a costimulatory molecule, or a nucleic acid encoding a costimulatory molecule. An Mtb polypeptide, or nucleic acid encoding the polypeptide, can be readily tested for its ability to induce a CD8+ T cell response.

Inhibiting or Treating a Disease:

Inhibiting a disease, such as tuberculosis, refers to inhibiting the full development of a disease. In several examples, inhibiting a disease refers to lessening symptoms of a tuberculosis. "Treatment" refers to a therapeutic intervention that ameliorates a sign or symptom of a disease or pathological condition related to the disease, such as tuberculosis.

Interferon Gamma (γ):

IFN-γ is a dimeric protein with subunits of 146 amino acids. The protein is glycosylated at two sites, and the pI is 8.3-8.5. IFN-γ is synthesized as a precursor protein of 166 amino acids including a secretory signal sequence of 23 amino acids. Two molecular forms of the biologically active protein of 20 and 25 kDa have been described. Both of them are glycosylated at position 25. The 25 kDa form is also glycosylated at position 97. The observed differences of natural IFN-γ with respect to molecular mass and charge are due to variable glycosylation patterns. 40-60 kDa forms observed under non-denaturing conditions are dimers and tetramers of IFN-γ. The human gene has a length of approximately 6 kb. It contains four exons and maps to chromosome 12q24.1.

IFN-γ can be detected by sensitive immunoassays, such as an ELSA test that allows detection of individual cells producing IFN-γ. Minute amounts of IFN-γ can be detected indirectly by measuring IFN-induced proteins such as Mx protein. The induction of the synthesis of IP-10 has been used also to measure IFN-γ concentrations. In addition, bioassays can be used to detect IFN-γ, such as an assay that employs induction of indoleamine 2,3-dioxygenase activity in 2D9 cells. The production of IFN-γ can be used to assess T cell activation, such as activation of a T cell by an HLA-E presented *Mycobacterium* antigen.

Isolated:

An "isolated" nucleic acid has been substantially separated or purified away from other nucleic acid sequences in the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids.

Label:

A detectable compound or composition that is conjugated directly or indirectly to another molecule to facilitate detection of that molecule. Specific, non-limiting examples of labels include fluorescent tags, enzymatic linkages, and radioactive isotopes.

Linker Sequence:

A linker sequence is an amino acid sequence that covalently links two polypeptide domains. Linker sequences can be included in the between the Mtb epitopes disclosed herein to provide rotational freedom to the linked polypeptide domains and thereby to promote proper domain folding and presentation to the MHC. By way of example, in a recombinant polypeptide comprising two Mtb domains, linker sequences can be provided between them, such as a polypeptide comprising Mtb polypeptide-linker-Mtb polypeptide. Linker sequences, which are generally between 2 and 25 amino acids in length, are well known in the art and include, but are not limited to, the glycine(4)-serine spacer (GGGGS (SEQ ID NO: 84)×3) described by Chaudhary et al., *Nature* 339:394-397, 1989.

Lymphocytes:

A type of white blood cell that is involved in the immune defenses of the body. There are two main types of lymphocytes: B cells and T cells.

Mammal:

This term includes both human and non-human mammals. Similarly, the term "patient" or "subject" includes both human and veterinary subjects.

*Mycobacteria:*

A genus of aerobic intracellular bacterial organisms. Upon invasion of a host, these organisms survive within endosomal compartments of monocytes and macrophages. Human mycobacterial diseases include tuberculosis (caused by *M. tuberculosis*), Leprosy (caused by *M. leprae*), Bairnsdale ulcers (caused by *M. ulcerans*), and other infections that can be caused by *M. marinum, M. kansasii, M. scrofulaceum, M. szulgai, M. xenopi, M. fortuitum, M. haemophilum, M. chelonei*, and *M. intracelluare. Mycobacterium* strains that were previously considered to be nonpathogenic (such as *M. avium*) are also now known to be major killers of immunosuppressed AIDS patients.

The major response to mycobacteria involves cell mediated hypersensitivity (DTH) reactions with T cells and macrophages playing major roles in the intracellular killing and walling off (or containing) of the organism (granuloma formation). A major T cell response involves CD4+ lymphocytes that recognize myocbacterial heat shock proteins and immunodominant antigens.

Operably Linked:

A first nucleic acid sequence is operably linked with a second nucleic acid sequence when the first nucleic acid sequence is placed in a functional relationship with the second nucleic acid sequence. For instance, a promoter is operably linked to a coding sequence if the promoter effects the transcription or expression of the coding sequence. Generally, operably linked DNA sequences are contiguous and, where necessary to join two protein coding regions, the open reading frames are aligned.

ORF (Open Reading Frame):

A series of nucleotide triplets (codons) coding for amino acids without any termination codons. These sequences are usually translatable into a polypeptide.

Peptide Modifications:

*Mycobacterium* polypeptides include synthetic embodiments of peptides described herein. In addition, analogues (non-peptide organic molecules), derivatives (chemically functionalized peptide molecules obtained starting with the disclosed peptide sequences) and variants (homologs) of these proteins can be utilized in the methods described herein. Each polypeptide of the invention is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of a *Mycobacterium* polypeptide having measurable or enhanced ability to generate an immune response. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press: Buffalo Grove, Ill., pp. 165-174 and *Principles of Pharmacology* Munson (ed.) 1995, Ch. 102, for descriptions of techniques used in CADD. Also included are mimetics prepared using such techniques.

Pharmaceutical Agent or Drug:

A chemical compound or composition capable of inducing a desired therapeutic or prophylactic effect when properly administered to a subject.

Pharmaceutically Acceptable Carriers:

The pharmaceutically acceptable carriers useful with the polypeptides and nucleic acids described herein are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide:

A linear nucleotide sequence, including sequences of greater than 100 nucleotide bases in length.

Polypeptide:

Any chain of amino acids, regardless of length or post-translational modification (e.g., glycosylation or phosphorylation). A "peptide" is a chain of amino acids that is less than 100 amino acids in length. In one embodiment, a "peptide" is a portion of a polypeptide, such as at about 10, 20, 30, 40, 50, or 100 contiguous amino acids of a polypeptide that is greater than 100 amino acids in length.

Portion of a Nucleic Acid Sequence:

At least 10, 20, 30 or 40 contiguous nucleotides of the relevant sequence, such as a sequence encoding an antigen. In some instances it would be advantageous to use a portion consisting of 50 or more nucleotides. For instance, when describing a portion of an antigen (such as an antigenic epitope), it may be advantageous to remove a portion of the relevant sequence comprising at least 10, 20, 30, 40 or 50 nucleotides up to a length.

Probes and Primers:

Nucleic acid probes and primers may readily be prepared based on the nucleic acids provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (1989) and Ausubel et al. (1987).

Primers are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in *Molecular Cloning: A Laboratory Manual,* 2nd ed., vol. 1-3, ed. Sambrook et al., Cold Spring Harbor Laboratory Press, Cold Spring Harbor, N.Y., 1989, and *Current Protocols in Molecular Biology*, ed. Ausubel et al., Greene Publishing and Wiley-Interscience, New York, 1987 (with periodic updates). PCR primer pairs can be derived from a known sequence, for example, by using computer programs intended for that purpose such as Primer (Version 0.5,© 1991, Whitehead Institute for Biomedical Research, Cambridge, Mass.).

Preventing or Treating a Disease:

"Preventing" a disease refers to inhibiting the full development of a disease, for example in a person who is known to be at risk of infection with *M. tuberculosis*, or *M. leprae*. An example of a person with a known predisposition is someone living with a person diagnosed with tuberculosis, health care professionals, or someone in the family, or who has been exposed to *M. tuberculosis*. "Preventing an active infection" refers to preventing a latent infection from transforming into tuberculosis.

"Treatment" refers to a therapeutic intervention that ameliorates a sign or symptom of a disease or pathological condition, such as tuberculosis, after it has begun to develop.

Promoter:

A promoter is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. The promoter can be a constitutive or an inducible promoter. A specific, non-limiting example of a promoter is the HCMV IE promoter.

Purified:

The term purified does not require absolute purity; rather, it is intended as a relative term. Thus, for example, a purified antigen preparation is one in which the antigen is more pure than the protein in its originating environment within a cell. A preparation of an antigen is typically purified such that the antigen represents at least 50% of the total protein content of the preparation. However, more highly purified preparations may be required for certain applications. For example, for such applications, preparations in which the antigen comprises at least 75% or at least 90% of the total protein content may be employed. In some examples a purified antigen is at least 90%, at least 95%, at least 98% or at least 99% of the total protein content.

Recombinant:

A recombinant nucleic acid or polypeptide is one that has a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques.

Sequence Identity:

The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Variants of antigen polypeptides will possess a relatively high degree of sequence identity when aligned using standard methods.

Methods of alignment of sequences for comparison are well known in the art. Altschul et al. (1994) presents a detailed consideration of sequence alignment methods and homology calculations. The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI website. A description of how to determine sequence identity using this program is available at the NCBI website, as are the default parameters.

Variants of antigenic polypeptides, such as a *Mycobacterium* polypeptide, are typically characterized by possession of at least 50% sequence identity counted over the full length alignment with the amino acid sequence of a native antigen sequence using the NCBI Blast 2.0, gapped blastp set to default parameters. Proteins with even greater similarity to the reference sequences will show increasing percentage identities when assessed by this method, such as at least 60%, at least 65%, at least 70%, at least 75%, at least 80%, at least 90% or at least 95% sequence identity. When less than the entire sequence is being compared for sequence identity, variants will typically possess at least 75% sequence identity over short windows of 10-20 amino acids, and may possess sequence identities of at least 85% or at least 90% or 95% depending on their similarity to the reference sequence. Methods for determining sequence identity over such short windows are described at the NCBI website. Variants of MHC domain polypeptides also retain the biological activity of the native polypeptide. For the purposes of this invention, that activity is conveniently assessed by incorporating the variant domain in the appropriate $\beta1\alpha1$ or $\alpha1\alpha2$ polypeptide and determining the ability of the resulting polypeptide to inhibit antigen specific T-cell proliferation in vitro, or to induce T suppressor cells or the expression of IL-10 as described in detail below.

Therapeutically Active Polypeptide:

An agent, such as an epitope of Mtb that causes induction of an immune response, as measured by clinical response (for example increase in a population of immune cells, increased cytolytic activity against Mtb, or measurable reduction of a symptom of an infection). Therapeutically active molecules can also be made from nucleic acids. Examples of a nucleic acid based therapeutically active molecule is a nucleic acid sequence that encodes an Mtb epitope, wherein the nucleic acid sequence is operably linked to a control element such as a promoter.

In one embodiment, a therapeutically effective amount of an Mtb polypeptide is an amount used to generate an immune response. In several examples, "treatment" refers to a therapeutic intervention that ameliorates a sign or symptom of tuberculosis.

Therapeutically Effective Dose:

A dose sufficient to prevent advancement, or to cause regression of the disease, or which is capable of relieving symptoms caused by the disease. In one embodiment, a therapeutically effective dose is a dose sufficient to prevent advancement or relieve symptoms of tuberculosis.

Transduced and Transformed:

A virus or vector "transduces" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Tuberculosis (TB) Disease:

A disease that is generally caused by *Mycobacterium tuberculosis* infection. Tuberculosis disease includes pulmonary and extra-pulmonary tuberculosis disease. Tuberculosis disease is a symptomatic condition resulting from infection with Mtb.

Pulmonary tuberculosis disease is a pulmonary disease caused Mtb. According to the Center for Disease Control, symptoms usually include coughing, and can included coughing up blood or sputum, pain in the chest, weakness, weight loss, fever, chills, and night sweats.

Transmission of *M. tuberculosis* occurs by the airborne route in confined areas with poor ventilation. In more than 90% of cases, following infection with *M. tuberculosis*, the immune system prevents development of disease from *M. tuberculosis*, often called, active tuberculosis. However, not all of the *M. tuberculosis* is killed, and thus tiny, hard capsules are formed. "Primary tuberculosis" is disease that develops following an initial infection, usually in children. The initial focus of infection is a small subpleural granuloma accompanied. by granulomatous hilar lymph node infection. Together, these make up the Ghon complex. In nearly all cases, these granulomas resolve and there is no further spread of the infection. "Secondary tuberculosis" is seen mostly in adults as a reactivation of previous infection (or re-infection), particularly when health status declines. The granulomatous inflammation is much more florid and widespread. Typically, the upper lung lobes are most affected, and cavitation can occur. "Latent" tuberculosis is an Mtb infection in an individual that can be detected by a diagnostic assay, such as, but not limited to a tuberculin skin test (TST) wherein the infection does not produce symptoms in that individual. "Active" tuberculosis is a symptomatic Mtb infection in a subject.

Microscopically, the inflammation produced with TB infection is granulomatous, with epithelioid macrophages and Langhans giant cells along with lymphocytes, plasma cells, maybe a few polymorphonuclear cells, fibroblasts with collagen, and characteristic caseous necrosis in the center. The inflammatory response is mediated by a type IV hypersensitivity reaction, and skin testing is based on this reaction. In some examples, tuberculosis can be diagnosed by a skin test, an acid fast stain, an auramine stain, or a combination thereof. The most common specimen screened is sputum, but the histologic stains can also be performed on tissues or other body fluids.

TB is a frequent complication of HIV infection. TB infection in subjects infected with a human immunodeficiency virus (HIV) can spread readily and progress rapidly to active disease. Specific symptoms of lung disease due to Mtb infection include chronic cough and spitting blood. Other symptoms of TB disease include fatigue, loss of appetite, weight loss, fever and drenching night sweats.

An Mtb infection is often a pulmonary infection. However, dissemination of tuberculosis outside of lungs can lead to the appearance of a number of uncommon findings with characteristic patterns that include skeletal tuberculosis, genital tract tuberculosis, urinary tract tuberculosis, central nervous system (CNS) tuberculosis, gastrointestinal tuberculosis, adrenal tuberculosis, scrofula, and cardiac tuberculosis. Thus, an MtB infection can also be extrapulmonary. Extrapulmonary sites of infection commonly include lymph nodes, pleura, and osteoarticular areas, although any organ can be involved. The diagnosis of extrapulmonary tuberculosis often is elusive. Generally children and subject who are immunosuppressed are susceptible to extra-pulmonary Mtb infections.

Lymphadenitis is the most commonly occurring form of extrapulmonary tuberculosis. Cervical adenopathy is most common, but inguinal, axillary, mesenteric, mediastinal, and intramammary involvement all have been described. In the United States, pleural tuberculosis accounts for about 5 percent of all tuberculosis cases. Pleural tuberculosis often is an acute illness with cough, pleuritic chest pain, fever, or dyspnea. Bone and joint tuberculosis may account for up to 35 percent of cases of extrapulmonary tuberculosis. Skeletal tuberculosis most often involves the spine, followed by tuberculous arthritis in weight-bearing joints and extraspinal tuberculous osteomyelitis. Central nervous system tuberculosis includes tuberculous meningitis (the most common presentation), intracranial tuberculomas, and spinal tuberculous arachnoiditis. Meningitis results from intense inflammation following rupture of a subependymal tubercle into the subarachnoid space. Abdominal tuberculosis may involve the gastrointestinal tract, peritoneum, mesenteric lymph nodes, or genitourinary tract. Other organs (e.g., liver, spleen, adrenal glands) usually are affected in miliary tuberculosis. Miliary tuberculosis, tuberculous pericarditis, and tuberculosis associated with tumor necrosis factor-alpha (TNF-alpha) inhibitors are additional forms of extra-pulmonary tuberculosis. The term "miliary" tuberculosis refers to any progressive, disseminated form of tuberculosis; the disease can occur during primary dissemination or after years of untreated tuberculosis. Miliary disease is seen in 10 percent of patients who have AIDS and pulmonary tuberculosis, and in 38 percent of those who have AIDS and extrapulmonary tuberculosis.

A six- to nine-month regimen (two months of isoniazid, rifampin, pyrazinamide, and ethambutol, followed by four to seven months of isoniazid and rifampin) is recommended as initial therapy for all forms of extrapulmonary tuberculosis unless the organisms are known or strongly suspected to be resistant to the first-line drugs.

Vector:

A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art. Vectors include plasmid vectors, including plasmids for expression in gram negative and gram positive bacterial cell. Exemplary vectors include those for expression in *E. coli* and *Salmonella*. Vectors also include viral vectors, such as, but are not limited to, retrovirus, *orthopox*, avipox, fowlpox, capripox, suipox, adenoviral, herpes virus, alpha virus, baculovirus, Sindbis virus, vaccinia virus and poliovirus vectors. Vectors also include vectors for expression in yeast cells Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Method for Detecting an Mtb Infection

Detection of T Cells

Methods for detection of a *Mycobacterium* infection in children and in subjects with a latent tuberculosis infection (LTBI) are disclosed herein. The child can be any child, including an infant, young child, older child, a child less than about five years of age, a child of ten years of age or less, a prepubescent child or a teenager. In several examples, the child is ten years of age or less, such as seven years of age or less or five years of age or less, or from five to ten years of age. In some embodiments, the child has a household contact with TB or LTBI. A household contact is any individual cohabitating with the child. In other embodiments the subject is any subject suspected of having LTBI. In one example, a subject suspected of having LTBI has a house contact with an Mtb infection or has traveled to a country with a high incidence of tuberculosis.

In one embodiment, the method is method for detecting tuberculosis disease, including pulmonary and/or extra-pulmonary tuberculosis disease. Tuberculosis disease is a symptomatic condition resulting from infection with Mtb. Pulmonary tuberculosis disease is disease caused Mtb which results in pnuemonia. Methods are provided herein for detecting pulmonary tuberculosis, such as in a child. The child can be any child, including an infant, young child, older child, a child less than about five years of age, a child of ten years of age or less, a child of five to ten years of age, a prepubescent child or a teenager. The child can also be as seven years of age or less, or six years of age or less, or from four to eleven years of age.

Methods are also disclosed to detect an extra-pulmonary infection with tuberculosis in either an adult subject or a child. The child can be any child, including an infant, young child, older child, a child less than about five years of age, a child of ten years of age or less, a child of five to ten years of age, a prepubescent child or a teenager. The child can also be as seven years of age or less, or six years of age or less, or from four to eleven years of age. In other examples, the subject is immunocompromised as a result of a genetic disorder, immunosuppressive therapy, or an infection with an immunodeficiency virus such as a human immunodeficiency virus (HIV).

The extra-pulmonary tuberculosis can be any form of the disease, including lymphadenitis, pleural tuberculosis, bone and joint tuberculosis central nervous system tuberculosis, abdominal tuberculosis, miliary tuberculosis, tuberculous pericarditis, and tuberculosis associated with tumor necrosis factor-alpha (TNF-alpha) inhibitors. The method can be used to detect skeletal tuberculosis of the spine, tuberculous arthritis in weight-bearing joints, and extraspinal tuberculous osteomyelitis. The method can be used to diagnose central nervous system tuberculosis including tuberculous meningitis (the most common presentation), intracranial tuberculomas, and spinal tuberculous arachnoiditis. The method can also be used to diagnose abdominal tuberculosis, such as an infection of the gastrointestinal tract, peritoneum, mesenteric lymph nodes, or genitourinary tract.

In several embodiments, a *Mycobacterium* infection (and/or tuberculosis disease) can be detected based on the presence of $CD8^+$ T cells in a biological sample, wherein the T cells specifically react with a Mtb polypeptide. In one example, the sample is incubated with one or more *Mycobacterium* polypeptides, as disclosed herein, a polynucleotide encoding the one or more Mtb polypeptide and an APC that expresses the one or more Mtb polypeptide or a fragment thereof that binds MHC. The presence or absence of specific activation of the $CD8^+$ T cells is detected. The activation of the $CD8^+$ T cells indicates that a Myobacterium infection is present. In one example, the activation of $CD8^+$ T cells is detected by measuring the expression of cytokine, such as, but not limited to, interferon-$\gamma$.

In several embodiments, the method includes isolating $CD8^+$ T cells. In several embodiments, a biological sample comprising T cells is obtained from a subject of interest. Suitable biological samples include, but are not limited to, blood samples, peripheral blood mononuclear cells, sputum, saliva, cerebral spinal fluid or samples of isolated T cells (such as $CD3^+$ T cells), lymph node tissue, lung tissue, or other tissue sample.

The $CD8^+$ T cells which recognize the peptide in the detection method have generally been presensitized in vivo to the Mtb polypeptide of interest. In several embodiments, these antigen-experienced T cells are generally present in the peripheral blood of a host which has been exposed to the antigen at a frequency of 1 to $10^6$ to 1 in $10^3$ peripheral blood mononuclear cells (PBMCs).

T cells can be isolated from a subject of interest, such as but not limited to an infant, young child, older child, child of five to ten years of age, child of less than five years of age, child of less than ten years of age, teenager, child cohabitating with an individual with TB or LTBI, any subject with a suspected LTBI, or suspected of having tuberculosis disease, such as pulmonary disease. T cells can also be isolated from any subject suspected of having an extra-pulmonary mTB infection, including children, pre-pubescent and adult subjects. The T cells can be isolated by routine techniques (such as by Ficoll/Hypaque density gradient centrifugation of peripheral blood lymphocytes, or by fluorescence activated cell sorting). In one embodiment the T cells used in the assay are in the form of unprocessed or diluted samples, or are freshly isolated T cells (such as in the form of freshly isolated mononuclear cells (MCs) or peripheral blood mononuclear cells (PBMCs) which are used directly ex vivo, such that they are not cultured before being used in the method. However the T cells can be cultured before use, for example in the presence of one or more of the peptides, and generally also exogenous growth promoting cytokines. During culturing the peptides are typically presented on the surface of cells such as APCs. Pre-culturing of the T cells may lead to an increase in the sensitivity of the method. Thus, the T cells can be converted into cell lines, such as short term cell lines.

Methods of determining the presence or absence of a cell surface marker, such as CD8, are well known in the art.

Typically, labeled antibodies specifically directed to the marker are used to identify the cell population. The antibodies can be conjugated to other compounds including, but not limited to, enzymes, magnetic beads, colloidal magnetic beads, haptens, fluorochromes, metal compounds, radioactive compounds or drugs. The enzymes that can be conjugated to the antibodies include, but are not limited to, alkaline phosphatase, peroxidase, urease and β-galactosidase. The fluorochromes that can be conjugated to the antibodies include, but are not limited to, fluorescein isothiocyanate, tetramethylrhodamine isothiocyanate, phycoerythrin, allophycocyanins and Texas Red. For additional fluorochromes that can be conjugated to antibodies see Haugland, R. P., *Molecular Probes: Handbook of Fluorescent Probes and Research Chemicals* (1992-1994). The metal compounds that can be conjugated to the antibodies include, but are not limited to, ferritin, colloidal gold, and particularly, colloidal superparamagnetic beads. The haptens that can be conjugated to the antibodies include, but are not limited to, biotin, digoxigenin, oxazalone, and nitrophenol. The radioactive compounds that can be conjugated or incorporated into the antibodies are known to the art, and include but are not limited to technetium 99m ($^{99}$Tc), $^{125}$I and amino acids comprising any radionuclides, including, but not limited to, $^{14}$C, $^{3}$H and $^{35}$S.

Fluorescence activated cell sorting (FACS) can be used to sort cells that express CD8, by contact the cells with an appropriately labeled antibody. In one embodiment, additional antibodies and FACS sorting can further be used to produce substantially purified populations of CD8$^+$CD3$^+$ cells, or to purify cells that do not express detectable levels of CD4 or CD56.

A FACS employs a plurality of color channels, low angle and obtuse light-scattering detection channels, and impedance channels, among other more sophisticated levels of detection, to separate or sort cells. Any FACS technique may be employed as long as it is not detrimental to the viability of the desired cells. (For exemplary methods of FACS see U.S. Pat. No. 5,061,620, herein incorporated by reference). Similarly, FACS can be used to substantially purify CD8$^+$ cells, such as CD8+ cells that express CD3 but do not express CD56 or CD4.

However, other techniques of differing efficacy may be employed to purify and isolate desired populations of cells. The separation techniques employed should maximize the retention of viability of the fraction of the cells to be collected. The particular technique employed will, of course, depend upon the efficiency of separation, cytotoxicity of the method, the ease and speed of separation, and what equipment and/or technical skill is required.

Separation procedures may include magnetic separation, using antibody-coated magnetic beads, affinity chromatography, cytotoxic agents, either joined to a monoclonal antibody or used in conjunction with complement, and "panning," which utilizes a monoclonal antibody attached to a solid matrix, or another convenient technique. Antibodies attached to magnetic beads and other solid matrices, such as agarose beads, polystyrene beads, hollow fiber membranes and plastic petri dishes, allow for direct separation. Cells that are bound by the antibody can be removed from the cell suspension by simply physically separating the solid support from the cell suspension. The exact conditions and duration of incubation of the cells with the solid phase-linked antibodies will depend upon several factors specific to the system employed. The selection of appropriate conditions, however, is well within the skill in the art.

The unbound cells then can be eluted or washed away with physiologic buffer after sufficient time has been allowed for the cells expressing a marker of interest (such as CD8) to bind to the solid-phase linked antibodies. The bound cells are then separated from the solid phase by any appropriate method, depending mainly upon the nature of the solid phase and the antibody employed.

Antibodies may be conjugated to biotin, which then can be removed with avidin or streptavidin bound to a support, or fluorochromes, which can be used with a fluorescence activated cell sorter (FACS), to enable cell separation (see above). The CD8 cells initially may be separated from other cells by the cell-surface expression of CD3. In one specific, non-limiting example, CD3$^+$ cells are positively selected by magnetic bead separation, wherein magnetic beads are coated with CD3 reactive monoclonal antibody. The CD3$^+$ cells then are then removed from the magnetic beads.

Release of the CD3$^+$ cells from the magnetic beads can effected by culture release or other methods. Purity of the isolated CD3$^+$ cells is then checked with a FACSCAN® flow cytometer (Becton Dickinson, San Jose, Calif.), for example, if so desired. In one embodiment, further purification steps are performed, such as FACS sorting the population of cells released from the magnetic beads.

In one embodiment, magnetic bead separation is used to first separate a population of cells that do not express more than one lineage specific markers, for example, B220, CD4, CD45, CD5, or CD56. In addition, panning can be used to separate cells that do not express one or more B cell or macrophage lineage specific markers (for panning methods see Small et al., *J Immunol Methods* 3; 167(1-2):103-7, 1994, herein incorporated by reference).

In several embodiments, once isolated, the CD8$^+$ T cells are incubated in vitro for two to nine days, such as about four days, at 37° C. with an Mtb polypeptide or fragment thereof that binds MHC. In several examples, the Mtb polypeptide or fragment thereof that binds MHC is included (at a concentration of, for example, about 5 to about 25 μg/ml, such as about 5, about 10, about 15, or about 20 μg/ml). In several examples, another aliquot of a T cell sample can be incubated in the absence of the Mtb polypeptide as a control. More than one Mtb polypeptide can also be utilized.

In one embodiment, mononuclear cells (MCs) are separated from the sample. The MCs include the T cells and antigen presenting cells (APCs). Thus in the method the APCs present in the separated MCs can present the peptide to the T cells. In another embodiment only T cells, such as only CD8$^+$ T cells, can be purified from the sample.

The APC used in the method may be any cell which has MHC class I molecules on its surface. It may or may not be a specialized antigen presenting cell, such as a B cell, dendritic cell or macrophage. The APC used in the method may be from the same host as the T cell. Generally, the APC is capable of presenting the peptide to a T cell. The APC can be a freshly isolated ex vivo cell or a cultured cell such as a cell from of a cell line. The APC can be allogeneic or autologous.

T cells derived from the sample from the subject of interest can be placed into an assay with all the Mtb polypeptides (or a pool of the Mtb polypeptides, or a specific Mtb polypeptide) which it is intended to test the relevant panel or the T cells can be divided and placed into separate assays each of which contain one or more of the peptides. In one embodiment, one or more of the polypeptides with an amino acid sequence set forth as SEQ ID NOs: 1-12, SEQ ID NO: 39 or SEQ ID NO: 61, or a fragment of one or more of these polypeptides that bind MHC, is utilized. In additional embodiments, one or more of the polypeptides is ESAT6 or CFP10, but any Mtb polypeptide can be utilized. Additional peptides of use are set forth in SEQ ID NOs: 39-83. Two or more of any of the Mtb peptides disclosed herein can be used for simultaneous, separate or sequential use of T cells that recognize these polypeptides. Additional combinations of any of the Mtb polypeptides disclosed herein can be utilized. Pools of Mtb polypeptdies are also of use.

In one embodiment the one or more peptide(s) is (are) provided to the presenting cell in the absence of the T cell. This cell is then provided to T cells isolated from the subject, typically after being allowed to present the peptide on its surface.

The duration for which the peptide is contacted with the cells will vary depending on the method used for determining recognition of the peptide. Typically $10^5$ to $10^7$, such as about $5 \times 10^5$ to $10^6$ T cells are added to each assay. In the case where peptide is added directly to the assay its concentration is typically from about $10^{-1}$ to about $10^3$ µg/ml, such as about 0.5 to about 50 µg/ml or about 1 to about 10 µg/ml. The length of time for which the T cells are incubated with the peptide can be from about 4 to about 24 hours, such as from about 6 to about 16 hours, or for about 12 hours.

The determination of the specific recognition of the peptide by the T cells, such as $CD8^+$ T cells can be performed by measuring the binding of the peptide to the T cells. Typically T cells which bind the peptide can be sorted based on this binding, for example using a fluorescence activated cell sorting (FACS) technique (see above). The detection of the presence of T cells which recognize the peptide will be deemed to occur if the frequency of cells sorted using the peptide is above a control value.

Determination of whether the T cells recognize the peptide can also be done by detecting a change in the state of the T cells in the presence of the peptide or determining whether the T cells bind the peptide. The change in state is generally caused by antigen specific functional activity of the T cell after the T cell receptor binds the peptide. Generally when binding the T cell receptor the peptide is bound to an MHC class I molecule, which may be present on the surface of a PBMC or an antigen presenting cell (APC).

T cell activation can be detected by any means known to one of skill in the art. In one example, $CD8^+$ T cell activation is detected by evaluating cytolytic activity; In another example, $CD8^+$ T cell activation is detected by proliferation. In several examples, a level of proliferation that is at least two fold greater and/or a level of cytolytic activity that is at least 20% greater than in uninfected subjects indicates the presence of a *Mycobacterium* infection in the subject of interest, such as a child, a subject with LTBI. In additional examples, a level of proliferation that is at least two fold greater and/or a level of cytolytic activity that is at least 20% greater than in uninfected subjects indicates that the subject has an extra-pulmonary tuberculosis disease and/or has a pulmonary tuberculosis disease. The subject can be any subject of interest, such as a child.

The change in state of the T cell may be the start of or increase in secretion of a substance from the T cell, such as a cytokine, such as interferon (IFN)-γ, IL-2 or TNF-α. In one example, the substance can be detected by allowing it to bind to a specific binding agent and then measuring the presence of the specific binding agent/substance complex. The specific binding agent is typically an antibody, such as polyclonal or monoclonal antibodies that binds the substance, such as the cytokine. Antibodies to cytokines are commercially available, or can be made using standard techniques.

Typically the specific binding agent such as the antibody is immobilized on a solid support. After the cytokine is allowed to bind the solid support can optionally be washed to remove material which is not specifically bound to the antibody. The antibody/cytokine complex can be detected by using a second binding agent which will bind the complex, such as an antibody that is labeled (either directly or indirectly) with a label. Generally, the second agent binds the substance at a site which is different from the site which binds the first agent.

In several examples, the second binding agent can be detected by a third agent which is labeled directly or indirectly by a detectable label. For example the second agent may include a biotin, allowing detection by a third agent which comprises a strepavidin and a label, such as an enzymatic, radioactive or fluorescent label.

In one embodiment the detection system is an ELISPOT assay, such as the assay described in PCT Publication No. WO 98/23960 or US Patent Publication No. 2005/0208594 both incorporated herein by reference. In one example, IFN-γ secreted from the T cell is bound by a first IFNγ specific antibody which is immobilized on a solid support. The bound IFN-γ is then detected using a second IFN-γ specific antibody which is labeled with a detectable label. Exemplary labeled antibodies are commercially available, such as from MABTECH™ (Stockholm, Sweden). An exemplary ELISPOT assay is described in the Examples section below. The detection method can be any other method for the detection of the expression of cytokines, see for example, Published European Patent Application No. EP1867988, which is incorporated by reference herein.

The change in state of the T cell also can be measured may be the increase in the uptake of substances by the T cell, such as the uptake of thymidine. The change in state can also be measured by an increase in the size of the T cells, or proliferation of the T cells, or a change in cell surface markers on the T cell.

Reagents are provided herein for the detection of CD8 expressing cells ($CD8^+$) that specifically bind a Mtb polypeptide as disclosed herein. These reagents are tetrameric MHC Class I/immunogenic TARP polypeptide complexes. These tetrameric complexes include an Mtb polypeptide, such as a polypeptide of nine to twenty amino acids in length that specifically binds MHC class I.

Tetrameric MHC Class I/peptide complexes can be synthesized using methods well known in the art (Altmann et al., *Science* 274:94, 1996, which is herein incorporated by reference). In one specific non-limiting example, purified HLA heavy chain polypeptide and β2-microglobulin (β2m) can be synthesized by means of a prokaryotic expression system. One specific, non-limiting example of an expression system of use is the pET system (R&D Systems, Minneapolis, Minn.). The heavy chain is modified by deletion of the transmembrane and cytosolic tail and COOH-terminal addition of a sequence containing the biotin protein ligase (Bir-A) enzymatic biotinylation site. Heavy chain, β2m, and peptide are then refolded. The refolded product can be isolated by any means known in the art, and then biotinylated by Bir-A. A tetramer is then produced by contacting the biotinylated product with strepavidin.

In one embodiment, the strepavidin is labeled. Suitable labels include, but are not limited to, enzymes, magnetic beads, colloidal magnetic beads, haptens, fluorochromes, metal compounds, radioactive compounds or drugs. The enzymes that can be conjugated to strepavidin include, but are not limited to, alkaline phosphatase, peroxidase, urease and β-galactosidase. The fluorochromes that can be conjugated to the strepavidin include, but are not limited to, fluorescein isothiocyanate, tetramethylrhodamine isothiocyanate, phycoerythrin, allophycocyanins and Texas Red. For additional fluorochromes that can be conjugated to strepavidin, see Haugland, R. P., *Molecular Probes: Handbook of Fluores-* cent Probes and Research Chemicals (1992-1994). The metal compounds that can be conjugated to the strepavidin include, but are not limited to, ferritin, colloidal gold, and particularly, colloidal superparamagnetic beads. The haptens that can be conjugated to the strepavidin include, but are not limited to, biotin, digoxigenin, oxazalone, and nitrophenol. The radioactive compounds that can be conjugated to strepavidin are known to the art, and include but are not limited to technetium 99m ($^{99}$Tc), $^{125}$I and amino acids comprising any radionuclides, including, but not limited to, $^{14}$C, $^{3}$H and $^{35}$S. Generally, strepavidin labeled with a fluorochrome is utilized in the methods disclosed herein.

In one embodiment, suspension of cells including T cells that specifically recognize an Mtb polypeptide is produced, and the cells are reacted with the tetramer in suspension. In one embodiment, these reagents are used to label cells, which are then analyzed by fluorescence activated cell sorting (FACS). A machine for FACS employs a plurality of color channels, low angle and obtuse light-scattering detection channels, and impedance channels, among other more sophisticated levels of detection, to separate or sort cells. Any FACS technique can be employed as long as it is not detrimental to the detection of the desired cells. (For exemplary methods of FACS see U.S. Pat. No. 5,061,620, incorporated herein by reference).

Method for Detecting an Mtb Infection

Skin Test Confirmation

In another aspect, in addition to the methods using CD8$^+$ T cells disclosed above, a confirmatory test is performed to confirm the diagnosis of an *Mycobacterium* infection, and in particular tuberculosis, using a skin test. A "skin test" is any assay performed directly on a patient in which a delayed-type hypersensitivity (DTH) reaction (such as induration, swelling, reddening or dermatitis) is measured following administration into the skin, such as the intradermal injection of one or more polypeptides described above. Such injection can be achieved using any suitable device sufficient to contact the polypeptide or polypeptides with dermal cells of the patient, such as a tuberculin syringe or 1 ml syringe. In several examples, the reaction is measured at least 48 hours after injection, such as between about 48 and about 72 hours after injection.

A DTH reaction is a cell-mediated immune response which is greater in subjects that have been exposed previously to the test antigen (the Mtb polypeptide, fragment thereof that binds MHC, or fusion protein thereof). The response can be measured visually, such as using a ruler. In several examples, a response that is greater than about 0.5 cm in diameter, such as greater than about 1.0 cm in diameter, is a positive response, and is indicative of *Mycobacterium* infection.

The Mtb polypeptides can be formulated for use in a skin test as pharmaceutical compositions containing a polypeptide and a physiologically acceptable carrier. These compositions typically contain one or more of the Mtb polypeptides (or a fragment thereof that binds MHC or a fusion protein thereof) in an amount ranging from about 1 μg to about 100 μg, such as from about 10 μg to about 50 μg in a volume of 0.1 ml. The carrier employed in a pharmaceutical composition can be a saline solution with appropriate preservatives, such as phenol and/or TWEEN80™.

Generally, the polypeptide employed in a skin test is of sufficient size such that it remains at the site of injection for the duration of the reaction period. In several examples, a polypeptide that is at least nine amino acids in length is sufficient. Without being bound by theory, the polypeptide is broken down by macrophages within hours of injection to allow presentation to T-cells. Such polypeptides can contain repeats of one or more of the above disclosed sequences and/or other immunogenic or non-immunogenic sequences.

Thus, the determination of the recognition of the peptide by the T cells can be measured in vivo. In several examples, the peptide is administered to the individual and then a response which indicates recognition of the peptide may be measured. In one embodiment the peptide is administered intradermally, typically in a similar manner to the Mantoux test. The peptide can be administered epidermally. The peptide is typically administered by needle, such as by injection, but can be administered by other methods such as ballistics, for example the ballistics techniques which have been used to deliver nucleic acids. Published EPC Application No. EP-A-0693119 describes techniques which can typically be used to administer the peptide. In several examples, from 0.001 to 1000 μg, for example from 0.01 to 100 μg or 0.1 to 10 μg of peptide is administered. Alternatively an agent can be administered which is capable of providing the peptides in vivo. Thus a polynucleotide capable of expressing the polypeptide can be administered. The polynucleotide typically has any of the characteristics of the polynucleotide which is discussed below. Polypeptide is expressed from the polynucleotide in vivo and recognition of the peptide in vivo may be measured. Typically from 0.001 to 1000 μg, for example from 0.01 to 100 μg or 0.1 to 10 μg of polynucleotide is administered.

Method for Detecting an Mtb Infection: Confirmatory Test, Detection of Antibodies In another aspect, in addition to the methods using CD8$^+$ T cells disclosed above, a confirmatory test is performed using one or more polypeptide(s) in an assay to determine the presence or absence of antibodies to the polypeptide(s) in a biological sample (such as, but not limited to, whole blood, sputum, serum, plasma, saliva, or cerebrospinal fluid) relative to a control. The presence of such antibodies indicates previous sensitization to mycobacterial antigens which may be indicative of *Mycobacterium* infection and, in particular, tuberculosis.

In embodiments in which more than one polypeptide is employed, the polypeptides can be complementary, such that one component polypeptide will detect infection in samples where the infection would not be detected by another component polypeptide). Complementary polypeptides may generally be identified by using each polypeptide individually to evaluate serum samples obtained from a series of patients known to be infected with *Mycobacterium*. After determining which samples are correctly identified as positive with each polypeptide, combinations of two or more polypeptides may be formulated that are capable of detecting infection in most, or all, of the samples tested. Complementary polypeptides are of use to improve sensitivity of a diagnostic test. Thus, more than one of the above-described Mtb polypeptides can be included in an assay. Additional polypeptides from Mtb (those not described herein) optionally can be included in the assay.

There are a variety of assay formats that can be used to detect antibodies in a sample (see, for example, Harlow and Lane, Antibodies: A Laboratory Manual, Cold Spring Harbor Laboratory (1988), which is incorporated herein by reference). In general, the presence or absence of an Mtb infection in a patient may be determined by (a) contacting a biological sample obtained from a patient with one or more Mtb polypeptides; (b) detecting in the sample the presence (or absence) of an antibody that binds to the polypeptide(s); and (c) comparing the level of antibody with a control. The control can be a standard value, such as a pre-determined cut-off value. The control can be the amount of antibodies in a subject known to be infected with Mtb, or the amount of antibodies that specifically bind the polypeptide(s) in a subject known not to be infected with Mtb.

In several embodiments, the assay involves the use of a polypeptide immobilized on a solid support. Antibodies that specifically bind the polypeptide(s) of interest bind to the solid support. The bound antibody can then be detected using a detection reagent that includes a detectable label. Suitable detection reagents include labeled antibodies that bind to the antibody/polypeptide complex. Suitable detection reagents also include second unlabeled antibodies that bind to the antibody polypeptide complex and a third antibody that specifically binds the second antibody. Suitable detection reagents also include unbound polypeptide labeled with a reporter group (such as in a semi-competitive assay).

Alternatively, a competitive assay may be utilized, in which an antibody that binds to the polypeptide of interest is labeled with a reporter group is incubated with the sample. Following incubation, the antibody is then allowed to bind to the immobilized antigen after incubation of the antigen with the sample. The extent to which components of the sample inhibit the binding of the labeled antibody to the immobilized polypeptide is indicative of the reactivity of the sample with the immobilized polypeptide.

A solid support used in an assay disclosed herein can be any solid material to which the antigen may be attached. For example, the solid support can be a test well in a microtiter plate or a nitrocellulose or other suitable membrane. Alternatively, the solid support may be a bead or disc, such as glass, fiberglass, latex or a plastic material such as polystyrene or polyvinylchloride. The support can also be a magnetic particle or a fiber optic sensor, such as those disclosed, for example, in U.S. Pat. No. 5,359,681.

The polypeptides can be bound to the solid support using a variety of techniques. The binding of the polypeptides can be accomplished by a noncovalent association, such as adsorption, or covalent attachment, such as a direct linkage between the antigen and functional groups on the support or a linkage through a cross-linking agent.

For binding by adsorption, binding can be achieved by contacting one or more Mtb polypeptide(s) (generally in a buffer) with the solid support for a suitable amount of time. The contact time for binding is typically between about 1 hour and 1 day. In general, binding is achieved by contacting a polystyrene or polyvinylchloride solid support with an amount of the one or more Mtb polypeptide(s) ranging from about 10 ng to about 1 µg, such as about 100 ng of antigen.

Covalent attachment of the Mtb polypeptide(s) of interest to a solid support can generally be achieved by reacting the support with a bifunctional reagent that reacts with both the support and a functional group, such as a hydroxyl or amino group, on the polypeptide. For example, an Mtb polypeptide can be bound to supports having an appropriate polymer coating using benzoquinone or by condensation of an aldehyde group on the support with an amine and an active hydrogen on the polypeptide (Pierce Immunotechnology Catalog and Handbook, at A12 A13, 1991).

In certain embodiments, the assay is an enzyme linked immunosorbent assay (ELISA). This assay can be performed by first contacting a polypeptide antigen that has been immobilized on a solid support (such as in the well of a microtiter plate) with the sample in a manner such that antibodies present within the sample that specifically bind the polypeptide of interest bind the immobilized polypeptide. Unbound sample is then removed and a detection reagent capable of binding to the immobilized antibody-polypeptide complex is added. The amount of detection reagent that remains bound is determined using a method appropriate for the specific detection reagent. For example, the detection method can detect fluorescence or the presence of an enzymatic activity.

In some embodiments, the polypeptide is immobilized on the support; any remaining protein binding sites on the support are typically blocked. Any suitable blocking agent can be used to block the unbound protein binding sites, such as bovine serum albumin or TWEEN 20™ can be employed. The immobilized polypeptide is then incubated with the sample, and the antibody is allowed to bind to the antigen. The sample can be diluted with a suitable diluent, for example a buffer such as phosphate-buffered saline (PBS) prior to incubation. In general, an appropriate contact time (incubation time) is a period of time that is sufficient to detect the presence of antibody in a *Mycobacterium*-infected sample. In one specific, non-limiting example, the contact time is sufficient to achieve a level of binding that is at least 95% of that achieved at equilibrium between bound and unbound antibody. The time necessary to achieve equilibrium can be determined by assaying the level of binding that occurs over a period of time. At room temperature, an incubation time of about 30 minutes is generally sufficient.

Unbound sample can then be removed by washing the solid support with an appropriate buffer, such as PBS containing 0.1% TWEEN 20™. A detection reagent can then be added to the solid support. A detection reagent can be any compound that binds to the immobilized antibody-polypeptide complex and can be detected. In several embodiments, the detection reagent contains a binding agent (such as, for example, Protein A, Protein G, immunoglobulin, lectin or free antigen) conjugated to a label. Labels of use include enzymes (such as horseradish peroxidase), substrates, cofactors, inhibitors, dyes, radionuclides, luminescent groups, fluorescent groups and biotin. The conjugation of a binding agent to a label can be achieved using methods known in the art; conjugated binding agents are also commercially available (such as from Zymed Laboratories, San Francisco, Calif., and Pierce, Rockford, Ill.).

The detection reagent is incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the label. For radioactive labels, scintillation counting or autoradiographic methods can be used for detection. Spectroscopic methods may be used to detect dyes, luminescent groups and fluorescent groups used as labels. Biotin can be detected using avidin coupled to a different label, such as a radioactive label, fluorescent label or an enzymatic label. Enzymatic labels can be detected by the addition of substrate (generally for a specific period of time), followed by spectroscopic or other analysis of the reaction products.

To determine the presence or absence of anti-Mycobacterium antibodies in the sample, the signal detected from the label that bound to the solid support is generally compared to a control. In one embodiment, the control is a standard value, such as the average mean signal obtained when the immobilized antigen is incubated with samples from an uninfected patient. In general, a sample generating a signal that is two or three standard deviations above the control is considered positive for *Mycobacterium* infection. In another embodiment, the control value is determined using a Receiver Operator Curve, according to the method of Sackett et al., Clinical Epidemiology: A Basic Science for Clinical Medicine, Little Brown and Co., pp. 106 107 (1985). Briefly, in this embodiment, the control value is determined from a plot of pairs of true positive rates (sensitivity) and false positive rates (100% specificity) that correspond to each possible control value for the diagnostic test result. The control value on the plot that encloses the largest area is the most accurate cut-off value, and a sample generating a signal that is higher than the cut-off value determined by this method is considered positive. Alternatively, the cut-off value may be shifted to minimize the false positive rate, or to minimize the false negative rate. In general, a sample generating a signal that is higher than the cut-off value determined by this method is considered positive for tuberculosis.

In a related embodiment, the assay is performed in a rapid flow-through or strip test format, wherein the antigen is immobilized on a membrane, such as, but not limited to, nitrocellulose. In a flow-through test, antibodies within the sample bind to the immobilized polypeptide as the sample passes through the membrane. A detection reagent (for example, protein A-colloidal gold) binds to the antibody-polypeptide complex as the solution containing the detection reagent flows through the membrane. The detection of bound detection reagent can be performed as described above.

In one example of the strip test format, one end of the membrane to which the polypeptide is bound is immersed in a solution containing the sample. The sample migrates along the membrane through a region containing the detection reagent and to the area of immobilized polypeptide. The concentration of the detection reagent at the polypeptide indicates the presence of anti-Mycobacterium antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an enzyme linked immunosorbant assay (ELISA). In several embodiments, the amount of polypeptide immobilized on the membrane ranges from about 25 ng to about 1 µg, such as from about 50 ng to about 500 ng. Such tests can typically be performed with a very small volume of patient serum or blood.

Method for Detecting an Mtb Infection

Confirmatory Test for Detection of Polynucleotides

In another aspect, in addition to the methods using $CD8^+$ T cells disclosed above, a confirmatory test is performed by detecting the presence, absence, or level of mRNA encoding a *Mycobacterium* polypeptide in a biological sample. In several examples, hybridization assays are utilized, such as Northern blot or dot blot assays. In additional examples, PCR based assays are utilized.

General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., BioTechniques 18:42044 (1995). In particular, RNA isolation can be performed using purification kit, buffer set and protease from commercial manufacturers, such as QIAGEN®, according to the manufacturer's instructions. For example, total RNA from cells in culture (such as those obtained from a subject) can be isolated using QIAGEN®RNeasy mini-columns. Other commercially available RNA isolation kits include MASTERPURE®. Complete DNA and RNA Purification Kit (EPICENTRE®Madison, Wis.), and Paraffin Block RNA Isolation Kit (Ambion, Inc.). Total RNA from tissue samples can be isolated using RNA Stat-60 (Tel-Test). RNA prepared a biological sample can be isolated, for example, by cesium chloride density gradient centrifugation.

Methods for quantitating mRNA are well known in the art. In one example, the method utilizes reverse transcriptase polymerase chain reaction (RT-PCR). Generally, the first step in gene expression profiling by RT-PCR is the reverse transcription of the RNA template into cDNA, followed by its exponential amplification in a PCR reaction. The two most commonly used reverse transcriptases are avian myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN® RT-PCR can be performed using commercially available equipment, such as, for example, ABI PRISM 7700® Sequence Detection System™ (Perkin-Elmer-Applied Biosystems, Foster City, Calif., USA), or Lightcycler (Roche Molecular Biochemicals, Mannheim, Germany). In one embodiment, the 5' nuclease procedure is run on a real-time quantitative PCR device such as the ABI PRISM 7700®. Sequence Detection System®. The system includes of thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

In some examples, 5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, RT-PCR is can be performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH), beta-actin, and 18S ribosomal RNA.

A more recent variation of the RT-PCR technique is the real time quantitative PCR, which measures PCR product accumulation through a dual-labeled fluorigenic probe (i.e., TAQMAN® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Held et al., Genome Research 6:986 994, 1996). Quantitative PCR is also described in U.S. Pat. No. 5,538,848, the disclosure of which is incorporated herein by reference. Related probes and quantitative amplification procedures are described in U.S. Pat. No. 5,716,784 and U.S. Pat. No. 5,723,591, the disclosures of which are incorporated herein by reference. Instruments for carrying out quantitative PCR in microtiter plates are available from PE Applied Biosystems, 850 Lincoln Centre Drive, Foster City, Calif. 94404 under the trademark ABI PRISM® 7700.

The steps of a representative protocol for quantitating gene expression using fixed, paraffin-embedded tissues as the RNA source, including mRNA isolation, purification, primer extension and amplification are given in various published journal articles (see Godfrey et al. J. Molec. Diagnostics 2: 84 91, 2000; K. Specht et al., Am. J. Pathol. 158: 419 29, 2001). Briefly, a representative process starts with cutting about 10 μm thick sections of paraffin-embedded tissue sample. The RNA is then extracted, and protein and DNA are removed. After analysis of the RNA concentration, RNA repair and/or amplification steps can be included, if necessary, and RNA is reverse transcribed using gene specific promoters followed by RT-PCR.

An alternative quantitative nucleic acid amplification procedure is described in U.S. Pat. No. 5,219,727, which is incorporated herein by reference. In this procedure, the amount of a target sequence in a sample is determined by simultaneously amplifying the target sequence and an internal standard nucleic acid segment. The amount of amplified DNA from each segment is determined and compared to a standard curve to determine the amount of the target nucleic acid segment that was present in the sample prior to amplification.

In some embodiments of this method, the expression of a "house keeping" gene or "internal control" can also be evaluated. These terms are meant to include any constitutively or globally expressed gene whose presence enables an assessment of cytokine mRNA levels. Such an assessment comprises a determination of the overall constitutive level of gene transcription and a control for variations in RNA recovery.

Monitoring the Progression of an Infection and/or Effectiveness of Therapy

In several embodiments, the diagnostic methods disclosed herein are used for monitoring the progression of a *Mycobacterium* infection, such as in a child, or a subject with LTBI. In this embodiment, assays as described above for the diagnosis of a *Mycobacterium* infection may be performed over time, and the change in the reactivity of $CD8^+$ T cells is measured. For example, the assays can be performed about every 12, 24, 36, 48, 60 or 72 hours for a specified period, such as over months or weeks, and thereafter performed as needed.

Generally, the *Mycobacterium* infection is progressing in those patients in whom the reactivity of $CD8^+$ T cells, such as detected using expression of a cytokine, such as IFN-γ, increases over time. In contrast, the *Mycobacterium* infection is not progressing when the reactivity of the $CD8^+$ T cells either remains constant or decreases with time. In this manner, the effectiveness of a particular therapeutic regimen can be assessed, such as in children or subjects with LTBI.

In one embodiment, the presence of T cells, such as $CD8^+$ T cells and/or $CD4^+$ T cells, that specifically recognize an Mtb polypeptide is assessed in a subject, such as a child. The subject is administered a therapeutic protocol. The presence of the T cells that specifically recognize the Mtb polypeptide is then assessed. An decrease or no change in the amount of $CD8^+$ T cells that specifically recognize the Mtb polypeptide as compared to the amount of the $CD8^+$ T cells, respectively, that specifically recognize the Mtb polypeptide prior to the administration of the therapeutic protocol indicates that the therapeutic protocol in not effective. An increase in the amount of the $CD8^+$ T cells and that specifically recognize the Mtb polypeptide as compared to the amount of the $CD8^+$ T cells that specifically recognize the Mtb polypeptide prior to the administration of the therapeutic protocol indicates that the therapeutic protocol is effective. $CD4^+$ cells can also be measured.

It should be noted that for any of the above-described assays, to improve sensitivity, multiple *Mycobacterium* markers may be assayed within a given sample. It will be apparent that the assays disclosed herein can be used in combination. Thus, sets of *Mycobacterium* polypeptides, and combinations of assays can be for optimal sensitivity and specificity.

*Mycobacterium* Polypeptides

It is disclosed herein that several *Mycobacterium* polypeptides can be used to induce an immune response to Mtb, such as a T cell response. The *Mycobacterium* polypeptides can be used in diagnostic assays to identify subjects infected with a *Mycobacterium* such as Mtb. In several embodiments, the polypeptide comprises or consists of the amino acid sequence set forth as:

```
1. MX1SRFMTDPHAMRDMAGRFEVHAQTVEDEARRMWASAQNISG
AGWSGMAEATSLDTMX2X3MNQAFRNIVNMLHGVRDGLVRDANNY
EQQEQASQQILS, (SEQ ID NO: 1, wherein X1 is A or T,
X2 is T or A and X3 is any amino acid,
such as Q or no amino acid)
```

In several examples, the polypeptide comprises, consists essentially of or consists of the amino acid sequence set forth as:

```
a. MASRFMTDPHAMRDMAGRFEVHAQTVEDEARRMWASAQNISGA
GWSGMAEATSLDTMTQMNQAFRNIVNMLHGVRDGLVRDANNYEQ
```

QEQASQQILS (SEQ ID NO: 2) (See also TUBERCULIST No. Rv1038c, as
available on Mar. 1, 2007, incorporated herein by reference, known as
EsxJ, ES6_2, TB11.0, QILSS)

b. MASRFMTDPHAMRDMAGRFEVHAQTVEDEARRMWASAQNISG
AGWSGMAEATSLDTMAQMNQAFRNIVNMLHGVRDGLVRDANNYE
QQEQASQQILSS (SEQ ID NO: 3, TUBERCULIST No. Rv1197, as
available on Mar. 1, 2007, incorporated herein by reference, also know as
EsxK, ES6_3, TB11.0, QILSS)

c. MASRFMTDPHAMRDMAGRFEVHAQTVEDEARRMWASAQNISG
AGWSGMAEATSLDTMT+MNQAFRNIVNMLHGVRDGLVRDANNYE
QQEQASQQILSS (SEQ ID NO: 4, TUBERCULIST No. Rv 1992, as
available on Mar. 1, 2007, incorporated herein by reference, as known as
EsxM, TB11.0, QILSS.

d. MATRFMTDPHAMRDMAGRFEVHAQTVEDEARRMWASAQNISG
AGWSGMAEATSLDTMAQMNQAFRNIVNMLHGVRDGLVRDANNYE
QQEQASQQILSS (SEQ ID NO: 5, TUBERCULIST No. Rv 2347c, as
available on Mar. 1, 2007, incorporated herein by reference, also known as
EsxP, ES6_7, QILSS)

e. MTSRFMTDPHAMRDMAGRFEVHAQTVEDEARRMWASAQNISG
AGWSGMAEATSLDTMTQMNQAFRNIVNMLHGVRDGLVRDANNYE
QQEQASQQILSS (SEQ ID NO: 6, TUBERCULIST No. Rv3620c, as
available on Mar. 1, 2007, incorporated herein by reference, also known as
EsxW, ES6_10, QILSS).

In additional embodiments, the polypeptide comprises, consists essentially of, or consists of the amino acid sequence set forth as:

2. MSYMIATPAALTAAATDIDGIGSAVSVANAAAVAATTGVLAAGG
DEVLAAIARLFNANAEEYHALSAQVAAFQTLFVRTLTGGCGVFRRR
RGRQCVTAAEHRAAGAGRRQRRRRSGDGQW
RLRQQRHFGCGGQPEFRQHSEHRR (SEQ ID NO: 7, TUBERCULIST
NO. Rv1088, as available on Mar. 1, 2007, incorporated herein by
reference, also known as PE9).

3. VSLVIATPQLLATAALDLASIGSQVSAANAAAAMPTTEVVAAAA
DEVSAAIAGLFGAHARQYQALSVQVAAFHEQFVQALTAAAGRYAST
EAAVERSLLGAVNAPTEALLGRPLIGNGADGTAPGQPGAAGGLLFG
NGGNGAAGGFGQTGGSGGAAGLIGNGGNGGAGGTGAAGGAGGNG
GWLWGNGGNGGVGGTSVAAGIGGAGGNGGNAGLFGHGGAGGTG
GAGLAGANGVNPTPGPAASTGDSPADVSGIGDQTGGDGGTGGHGTA
GTPTGGTGGDGATATAGSGKATGGAGGDGGTAAAGGGGNGGDG
GVAQGDIASAFGGDGGNGSDGVAAGSGGGSGGAGGGAFVHIATAT
STGGSGGFGGNGAASAASGADGGAGGAGGNGGAGGLLFGDGGNG
GAGGAGGIGGDGATGGPGGSGGNAGIARFDSPDPEAEPDVVGGKGG
DGGKGGSGLGVGGAGGTGGAGGNGGAGGLLFGNGGNGGNAGAGG
DGGAGVAGGVGGNGGGGGTATFHEDPVAGVWAVGGVGGDGGSG
GSSLGVGGVGGAGGVGGKGGASGMLIGNGGNGGSGGVGGAGGVG
GAGGDGGNGGSGGNASTFGDENSIGGAGGTGGNGGNGANGGNGG
AGGIAGGAGGSGGFLSGAAGVSGADGIGGAGGAGGAG
GAGGSGGEAGAGGLTNGPGSPGVSGTEGMAGAPG (SEQ ID NO: 8,
TUBERCULIST NO. Rv2487, as available on Mar. 1, 2007, incorporated
herein by reference, also known as PE_PGRS42)

4. MHQVDPNLTRRKGRLAALAIAAMASASLVTVAVPATANADPEPA
PPVPTTAASPPSTAAAPPAPATPVAPPPPAAANTPNAQPGDPNAAPPP
ADPNAPPPPVIAPNAPQPVRIDNPVGGFSFALPAGWVESDAAHFDYG
SALLSKTTGDPPFPGQPPPVANDTRIVLGRLDQKLYASAEATDSKAA
ARLGSDMGEFYMPYPGTRINQETVSLDANGVSGSASYYEVKFSDPSK
PNGQIWTGVIGSPAANAPDAGPPQRWFVVWLGTANNPVDKGAAKA
LAESIRPLVAPPPAPAPAPAEP APAPAPAGEVAPTPTTPTPQRTLPA
(SEQ ID NO: 9, TUBERCULIST No. Rv1860, as available on Mar. 1,
2007, incorporated herein by reference, also known as Apa, modD, mpt32)

5. MLLALLRQHIRPYRRLVAMLMMLQLVSTLASLYLPTVNAAIVDD
GVAKGDTATIVRLGAVMLGVTGLQVLCAIGAVYLGSRTGAGFGRDL
RSAMFEHIITFSERETARFGAPTLLTRSTNDVRQILFLVQMTATVLVT
APIMCVGGIIMAIHQEAALTWLLLVSVPILAVANYWIISHMLPLFRRM
QSLIDGINRVMRDQLSGVRVVRAFTREGYERDKFAQANTALSNAAL
SAGNWQALMLPVTTLTINASSVALIWFGGLRIDSGQMQVGSLIAFLS
YFAQILMAVLMATMTLAVLPRASVCAERITEVLSTPAALGNPDNPKF
PTDGVTGVVRLAGATFTYPGADCPVLQDISLTARPGTTTAIVGSTGS
GKSTLVSLICRLYDVTAGAVLVDGIDVREYHTERLWSAIGLVPQRSY
LFSGTVADNLRYGGGPDQVVTEQEMWEALRVAAADGFVQTDGLQT

-continued

RVAQGGVNFSGGQRQRLAIARAVIRRPAIYVFDDAFSALDVHTDAK
VHASLRQVSGDATIIVVTQRISNAAQADQVIVVDNGKIVGTGTHETL
LADCPTYAEFAASQSLSATVGGVG (SEQ ID NO: 10, TUBERCULIST
NO. Rv1273c, as available Mar. 1, 2007, incorporated herein by reference).

6. MSYVIAAPEMLATTAADVDGIGSAIRAASASAAGPTTGLLAAAA
DEVSSAAAALFSEYARECQEVLKQAAAFHGEFTRALAAAGAAYAQ
AEASNTAAMSGTAGSSGALGSVGMLSGNPLTALMMGGTGEPILSDR
VLAIIDSAYIRPIFGPNNPVAQYTPEQWWPFIGNLSLDQSIAQGVTLLN
NGINAELQNGHDVVVFGYSQSAAVATNEIRALMALPPGQAPDPSRL
AFTLIGNINNPNGGVLERYVGLYLPFLDMSFNGATPPDSPYQTYMYT
GQYDGYAHNPQYPLNILSDLNAFMGIRWVHNAYPFTAAEVANAVPL
PTSPGYTGNTHYYMFLTQDLPLLQPIRAIPFVGTPIAELIQPDLRVLVD
LGYGYGYADVPTPASLFAPINPIAVASALATGTVQGPQAALVSIGLLP
QSALPNTYPYLPSANPGLMFNFGQSSVTELSVLSGALGSVARLIPPIA
(SEQ ID NO: 11, TUBERCULIST NO. Rv0159c, as available Mar. 1,
2007, incorporated herein by reference, also know as PE3 or PE).

7. MEFPVLPPEINSVLMYSGAGSSPLLAAAAAWDGLAEELGSAAVSF
GQVTSGLTAGVWQGAAAAAMAAAAAPYAGWLGSVAAAAEAVAG
QARVVVGVFEAALAATVDPALVAANRARLVALAVSNLLGQNTPAIA
AAEAEYELMWAADVAAMAGYHSGASAAAAALPAFSPPAQALGGG
VGAFLTALFASPAKALSLNAGLGNVGNYNVGLGNVGVFNLGAGNV
GGQNLGFGNAGGTNVGFNLGNGNVGFGNSGLGAGLAGLGNIGLG
NAGSSNYGFANLGVGNIGFGNTGTNNVGVGLTGNHLTGIGGLNSGT
GNIGLFNSGTGNVGFFNSGTGNFGVFNSGNYNTGVGNAGTASTGLF
NAGNFNTGVVNVGSYNTGSFNAGDTNTGGFNPGGVNTGWLNTGNT
NTGIANSGNVNTGAFISGNFNNGVLWVGDYQGLFGVSAGSSIPAIPIG
LVLNGDIGPITIQPIPILPTIPLSIHQTVNLGPLVVPDIVIPAFGGGIGIPIN
IGPLTITPITLFAQQTFVNQLPFPTFSLGKITIPQIQTFDSNGQLVSFIGPI
VIDTTIPGPTNPQIDLTIRWDTPPITLFPNGISAPDNPLGLLVSVSISNPG
FTIPGFSVPAQPLPLSIDIEGQIDGFSTPPITIDRIPLTVGGGVTIGPITIQG
LHIPAAPGVGNTTTAPSSGFFNSGAGGVSGFGNVGAGSSGWWNQAP
SALLGAGSGVGNVGTLGSGVLNLGSGISGFYNTSVLPFGTPAAVSGI
GNLGQQLSGVSAAGTTLRSMLAGNLGLANVGNFNTGFGNVGDVNL
GAANIGGHNLGLGNVGDGNLGLGNIGHGNLGFANLGLTAGAAGVG
NVGFGNAGINNYGLANMGVGNIGFANTGTGNIGIGLVGDHRTGIGG
LNSGIGNIGLFNSGTGNVGFFNSGTGNFGIGNSGRFNTGIGNSGTAST
GLFNAGSFSTGIANTGDYNTGSFNAGDTNTGGFNPGGINTGWFNTGH
ANTGLANAGTFGTGAFMTGDYSNGLLWRGGYEGLVGVRVGPTISQF
PVTVHAIGGVGPLHVAPVPVPAVHVEITDATVGLGPFTVPPISIPSLP
IASITGSVDLAANTISPIRALDPLAGSIGLFLEPFRLSDPFITIDAFQVVA
GVLFLENIIVPGLTVSGQILVTPTPIPLTLNLDTTPWTLFPNGFTIPAQT
PVTVGMEVANDGFTFFPGGLTFPRASAGVTGLSVGLDAFTLLPDGFT
LDTVPATFDGTILIGDIPIPIIDVPAVPGFGNTTTAPSSGFFNTGGGGGS
GFANVGAGTSGWWNQGHDVLAGAGSGVANAGTLSSGVLNVGS
GISGWYNTSTLGAGTPAVVSGIGNLGQQLSGFLANGTVLNRSPIVNIG
WADVGAFNTGLGNVGDLNWGAANIGAQNLGLGNLGSGNVGFGNIG
AGNVGFANSGPAVGLAGLGNVGLSNAGSNNWGLANLGVGNIGLAN
TGTGNIGIGLVGDYQTGIGGLNSGSGNIGLFNSGTGNVGFFNTGTGNF
GLFNSGSFNTGIGNSGTGSTGLFNAGNFNTGIANPGSYNTGSFNVGDT
NTGGFNPGDINTGWFNTGIMNTGTRNTGALMSGTDSNGMLWRGDH
EGLFGLSYGITIPQFPIRITTTGGIGPIVIPDTTILPPLHLQITGDADYSFT
VPDIPIPAIHIGINGVVTVGFTAPEATLLSALKNNGSFISFGPITLSNIDIP
PMDFTLGLPVLGPITGQLGPIHLEPIVVAGIGVPLEIEPIPLDAISLSESIP
IRIPVDIPASVIDGISMSEVVPIDASVDIPAVTITGTTISAIPLGFDIRTSA
GPLNIPIIDIPAAPGFGNSTQMPSSGFFNTGAGGGSGIGNLGAGVSGLL
NQAGAGSLVGTLSGLGNAGTLASGVLNSGTAISGLFNVSTLDATTPA
VISGFSNLGDHMSGVSIDGLIAILTFPPAESVFDQIIDAAIAELQHLDIG
NALALGNVGGVNLGLANVGEFNLGAGNVGNINVGAGNLGGSNLGL
GNVGTGNLGFGNIGAGNFGFGNAGLTAGAGGLGNVGLGNAGS
GSWGLANVGVGNIGLANTGTGNIGIGLTGDYRTGIGGLNSGTGNLGL
FNSGTGNIGFFNTGTGNFGLFNSGSYSTGVGNAGTASTGLFNAGNFN
TGLANAGSYNTGSLNVGSFNTGGVNPGTVNTGWFNTGHTNTGLFNT
GNVNTGAFNSGSFNNGALWTGDYHGLVGFSFSIDIAGSTLLDLNETL
NLGPIHIEQIDIPGMSLFDVHEIVEIGPFTIPQVDVPAIPLEIHESIHMDPI
VLVPATTIPAQTRTIPLDIPASPGSTMTLPLISMRFEGEDWILGSTAAIP
NFGDPFPAPTQGITIHTGPGPGTTGELKISIPGFEIPQIATTRFLLDVNIS
GGLPAFTLFAGGLTIPTNAIPLTIDASGALDPITIFPGGYTIDPLPLHLAL
NLTVPDSSIPIIDVPPTPGFGNTTATPSSGFFNSGAGGVSGFGNVGSNL
SGWWNQAASALAGSGSGVLNVGTLGSGVLNVGSGVSGIYN
TSVLPLGTPAVLSGLGNVGHQLSGVSAAGTALNQIPILNIGLADVGNF
NVGFGNVGDVNLGAANLGAQNLGLGNVGTGNLGFANVGHGNIGFG
NSGLTAGAAGLGNTGFGNAGSANYGFANQGVRNIGLANTGTGNIGI
GLVGDNLTGIGGLNSGAGNIGLFNSGTGNIGFFNSGTGNFGIGNSGSF
NTGIGNSGTGSTGLFNAGSFNTGVANAGSYNTGSFNAGDTNTGGFNP
GTINTGWFNTGHTNTGIANSGNVGTGAFMSGNFSNGLLWRGDHEGL
FSLFYSLDVPRITIVDAHLDGGFGPVVLPPIPVPAVNAHLTGNVAMGA
FTIPQIDIPALTPNITGSAAFRIVVGSVRIPPVSVIVEQIINASVGAEMRI
DPFEMWTQGTNGLGITFYSFGSADGSPYATGPLVFGAGTSD
GSHLTISASSGAFTTPQLETGPITLGFQVPGSVNAITLFPGGLTFPATSL

```
LNLDVTAGAGGVDIPAITWPEIAASADGSVYVLASSIPLINIPPTPGIG
NSTITPSSGFFNAGAGGGSGFGNFGAGTSGWWNQAHTALAGAGSGF
ANVGTLHSGVLNLGSGVSGIYNTSTLGVGTPALVSGLGNVGHQLSG
LLSGGSAVNPVTVLNIGLANVGSHNAGFGNVGEVNLGAANLGAHNL
GFGNIGAGNLGFGNIGHGNVGVGNSGLTAGVPGLGNVGLGNAGGN
NWGLANVGVGNIGLANTGTGNIGIGLTGDYQTGIGGLNSGAGNLGL
FNSGAGNVGFFNTGTGNFGLFNSGSFNTGVGNSGTGSTGLFNAGSFN
TGVANAGSYNTGSFNVGDTNTGGFNPGSINTGWLNAGNANTGVAN
AGNVNTGAFVTGNFSNGILWRGDYQGLAGFAVGYTLPLFPAVGAD
VSGGIGPITVLPPIHIPPIPVGFAAVGGIGPIAIPDISVPSIHLGLDPAVHV
GSITVNPITVRTPPVLVSYSQGAVTSTSGPTSEIWVKPSFFPGIRIAPSS
GGGATSTQGAYFVGPISIPSGTVTFPGFTIPLDPIDIGLPVSLTIPGFTIP
GGTLIPTLPLGLALSNGIPPVDIPAIVLDRILLDLHADTTIGPINVPIAGF
GGAPGFGNSTTLPSSGFFNTGAGGGSGFSNTGAGMSGLLNAMSDPLL
GSASGFANFGTQLSGILNRGAGISGVYNTGALGVVTAAVVSGFGNV
GQQLSGLLFTGVGP (SEQ ID NO: 12, TUBERCULIST No. 3350c, as
available Mar. 1, 2007, herein incorporated by reference, also known as
PPE56 or PPE.
```

In additional embodiments, an Mtb polypeptide comprises, consists essentially of, or consists of ESAT-6:

(SEQ ID NO: 39)
MTEQQWNFAGIEAAASAIQGNVTSIHSLLDEGKQSLTKL
AAWGGGSGSEAYQGVQQKWDATATELNNALQNLARTISEAG
QAMASTEGNVTGMFA

Peptides of Use:

| | |
|---|---|
| MTEQQWNFAGIEAAA | SEQ ID NO: 40 |
| QWNFAGIEAAASAIQ | SEQ ID NO: 41 |
| AGIEAAASAIQGNVT | SEQ ID NO: 42 |
| AAASAIQGNVTSIHS | SEQ ID NO: 43 |
| AIQGNVTSIHSLLDE | SEQ ID NO: 44 |
| NVTSIHSLLDEGKQS | SEQ ID NO: 45 |
| IHSLLDEGKQSLTKL | SEQ ID NO: 46 |
| LDEGKQSLTKLAAAWG | SEQ ID NO: 47 |
| KQSLTKLAAAWGGSG | SEQ ID NO: 48 |
| TKLAAAWGGSGSEAY | SEQ ID NO: 49 |
| AAWGGSGSEAYQGVQ | SEQ ID NO: 50 |
| GSGSEAYQGVQQKWD | SEQ ID NO: 51 |
| EAYQGVQQKWDATAT | SEQ ID NO: 52 |
| GVQQKWDATATELNN | SEQ ID NO: 53 |
| KWDATATELNNALQN | SEQ ID NO: 54 |
| TATELNNALQNLART | SEQ ID NO: 55 |
| LNNALQNLARTISEA | SEQ ID NO: 56 |
| LQNLARTISEAGQAM | SEQ ID NO: 57 |
| ARTISEAGQAMASTE | SEQ ID NO: 58 |
| SEAGQAMASTEGNVT | SEQ ID NO: 59 |
| QAMASTEGNVTGMFA | SEQ ID NO: 60 |

In other embodiments, an MtB polypeptide comprises, consists essentially of, or consists of CFP-10:

(SEQ ID NO: 61)
MAEMKTDAATLAQEAGNFERISGDLKTQIDQVESTAGSLQGQWRG
AAGTAAQAAVVRFQEAANKQKQELDEISTNIRQAGVQYSRADEEQQ
QALSSQMG

Peptides of Use:

| | |
|---|---|
| MAEMKTDAATLAQEA | SEQ ID NO: 62 |
| KTDAATLAQEAGNFE | SEQ ID NO: 63 |
| ATLAQEAGNFERISG | SEQ ID NO: 64 |
| QEAGNFERISGDLKT | SEQ ID NO: 65 |
| NFERISGDLKTQIDQ | SEQ ID NO: 66 |
| ISGDLKTQIDQVEST | SEQ ID NO: 67 |
| LKTQIDQVESTAGSL | SEQ ID NO: 68 |
| IDQVESTAGSLQGQW | SEQ ID NO: 69 |
| ESTAGSLQGQWRGAA | SEQ ID NO: 70 |
| GSLQGQWRGAAGTAA | SEQ ID NO: 71 |
| GQWRGAAGTAAQAAV | SEQ ID NO: 72 |
| GAAGTAAQAAVVRFQ | SEQ ID NO: 73 |
| TAAQAAVVRFQEAAN | SEQ ID NO: 74 |
| AAVVRFQEAANKQKQ | SEQ ID NO: 75 |
| RFQEAANKQKQELDE | SEQ ID NO: 76 |
| AANKQKQELDEISTN | SEQ ID NO: 77 |
| QKQELDEISTNIRQA | SEQ ID NO: 78 |
| LDEISTNIRQAGVQY | SEQ ID NO: 79 |
| STNIRQAGVQYSRAD | SEQ ID NO: 80 |
| RQAGVQYSRADEEQQ | SEQ ID NO: 81 |
| VQYSRADEEQQQALS | SEQ ID NO: 82 |
| RADEEQQQALSSQMG | SEQ ID NO: 83 |

Additional Mtb polypeptides of use are disclosed in U.S. Published Patent Application No. 2005/0208594; PCT Publication No. WO 2005/0909988; U.S. Published Patent Application No. 2003/0147897; U.S. Published Patent Application No. 2004/01151211; U.S. Published Patent Application No.

2005/0272104; U.S. Published Patent Application No. 2006/0024332; U.S. Published Patent Application No. 2006/0115847; U.S. Published Patent Application No. 2007/0009547; U.S. Published Patent Application No. 2007/0184073, which are incorporated by reference herein in their entirety. More than one Mtb polypeptides can be used. In several embodiments, ESAT-6 (SEQ ID NO: 39) and/or CFP-10 (SEQ ID NO: 61) are utilized in the methods disclosed herein.

In another embodiment, an Mtb polypeptide of use in the methods disclosed herein has a sequence at least 75%, 85%, 90%, 95%, 96%, 97%, 98% or 99% homologous to one amino acid sequence set forth in one of SEQ ID NOs: 1-12 or 39-83. For example, the polypeptide can have an amino acid sequence, at least 85%, 90%, 95%, 96%, 97%, 98% or 99% homologous to one of the amino acid sequences set forth in SEQ ID NOs: 1-12 or 39-83. Exemplary sequences can be obtained using computer programs that are readily available on the internet and the amino acid sequences set forth herein. In one example, the polypeptide retains a function of the Mtb protein, such as binding to an antibody that specifically binds the Mtb epitope.

Minor modifications of an Mtb polypeptide primary amino acid sequences may result in peptides which have substantially equivalent activity as compared to the unmodified counterpart polypeptide described herein. Such modifications may be deliberate, as by site-directed mutagenesis, or may be spontaneous. All of the polypeptides produced by these modifications are included herein. Thus, a specific, non-limiting example of an Mtb polypeptide is a conservative variant of the Mtb polypeptide. A table of conservative substitutions is provided herein. Substitutions of the amino acids sequence shown in SEQ ID NOs: 1-12 and 39-83 can be made based on this table. In several embodiments, at most one, at most two, at most three, at most four, or at most five conservative substitutions are introduced into the Mtb polypeptide.

Mtb polypeptides are disclosed herein that can be used to detect an immune response to Mtb. These peptides include or consist of at least nine amino acids, such as nine to twenty amino acids consecutive amino acids of an Mtb polypeptide set forth above. Specific, non-limiting examples are twelve, eleven, ten amino acids, or nine consecutive amino acids of one of the Mtb polypeptides set forth above. In these examples, the Mtb polypeptide does not include the full-length amino acid sequences set forth as SEQ ID NOs: 1-12, SEQ ID NO: 39 and/or SEQ ID NO: 61.

An isolated polypeptide is disclosed that includes nine to twelve consecutive amino acids from an Mtb polypeptide, wherein the isolated polypeptide comprises the amino acid sequence set forth as QTVEDEARRMW (SEQ ID NO: 13). In some embodiments, the polypeptide is nine, ten or eleven amino acids in length. In additional embodiments, the polypeptide consists of the amino acid sequence set forth as SEQ ID NO: 13. An isolated polypeptide is disclosed that includes nine to twelve consecutive amino acids from an Mtb polypeptide, wherein the isolated polypeptide comprises the amino acid sequence set forth as VSAAIAGLF (SEQ ID NO: 14). In some embodiments, the polypeptide is nine, ten or eleven amino acids in length. In additional embodiments, the polypeptide consists of the amino acid sequence set forth as SEQ ID NO: 14.

In further embodiments the polypeptide is nine to twelve consecutive amino acids in length and comprises, consists essentially of, or consists of one of the amino acid sequences set forth as SEQ I DNOs: 40-60 or SEQ ID NOs: 65-83.

In several embodiments, the isolated Mtb polypeptide is included in a fusion protein. Thus, the fusion protein can include the Mtb polypeptide (see above) and a second heterologous moiety, such as a myc protein, an enzyme or a carrier (such as a hepatitis carrier protein or bovine serum albumin) covalently linked to the Mtb polypeptide. In several examples, a polypeptide consisting of nine to twelve amino acids of one of the amino acid sequences set forth as SEQ ID NOs: 1-14, SEQ ID NO: 39 or SEQ ID NO: 61 that bind MHC class I is covalently linked to a carrier. In additional example, a polypeptide consisting of one of the amino acid sequences set forth as one of SEQ ID NOs: 1-14 or consisting of one of the amino acid sequence set forth as SEQ ID NO: 40-60 or 65-83 is covalently linked to a carrier.

In additional examples, the polypeptide can be a fusion protein and can also include heterologous sequences to Mtb (such as amino acid sequences of at least nine amino acids in length that are not included in SEQ ID NO: 1). Thus, in several specific non-limiting examples, the immunogenic peptide is a fusion polypeptide, for example the polypeptide includes six sequential histidine residues, a β-galactosidase amino acid sequence, or an immunoglobulin amino acid sequence. The polypeptide can also be covalently linked to a carrier. In additional embodiments, the protein consists of the Mtb polypeptide.

The polypeptide can optionally include repetitions of one or more of the Mtb polypeptides disclosed herein. In one specific, non-limiting example, the polypeptide includes two, three, four, five, or up to ten repetitions of one of the Mtb polypeptides described above. Alternatively, more than one polypeptide can be included in a fusion polypeptide. Thus, in several examples, the polypeptide can include at least two, at least three, at least four, at least five or at least six of the amino acid sequences set forth as SEQ ID NOs: 1-14 and/or SEQ ID NOs: 39-83. A linker sequence can optionally be included between the Mtb polypeptides.

The Mtb polypeptides disclosed herein can be chemically synthesized by standard methods, or can be produced recombinantly. An exemplary process for polypeptide production is described in Lu et al., *Federation of European Biochemical Societies Letters*. 429:31-35, 1998. They can also be isolated by methods including preparative chromatography and immunological separations.

If desired, polypeptides can also be chemically synthesized by emerging technologies. One such process is described in W. Lu et al., *Federation of European Biochemical Societies Letters*. 429:31-35, 1998. Polypeptides can also be produced using molecular genetic techniques, such as by inserting a nucleic acid encoding Mtb or an epitope thereof into an expression vector, introducing the expression vector into a host cell, and isolating the polypeptide (see below).

Polynucleotides encoding the Mtb polypeptides disclosed herein are also provided. Exemplary nucleic acid sequences are set forth below:

ESXJ (ESAT-6 LIKE PROTEIN 2)

(SEQ ID NO: 15)
atggcctcgcgttttatgacggatccgcacgcgatgcgggacatggcgggccgttttgag gtgcacgcccagacggtggaggacgaggctcgccggatgtgggcgtccgcgcaaaacatc -continued tcgggcgcgggctggagtggcatggccgaggcgacctcgctagacaccatgacccagatg aatcaggcgtttcgcaacatcgtgaacatgctgcacggggtgcgtgacgggctggttcgc gacgccaacaactacgaacagaagagcaggcctcccagcagatcctcagcagctga ESXK (ESAT-6 LIKE PROTEIN 3)
(SEQ ID NO: 16)
atggcctcacgttttatgacggatccgcacgcgatgcgggacatggcgggccgttttgag gtgcacgcccagacggtggaggacgaggctcgccggatgtgggcgtccgcgcaaaacatt tccggtgcgggctggagtggcatggccgaggcgacctcgctagacaccatggcccagatg aatcaggcgtttcgcaacatcgtgaacatgctgcacggggtgcgtgacgggctggttcgc gacgccaacaactacgagcagcaagagcaggcctcccagcagatcctcagcagctaa ESXM (ESAT-6 LIKE PROTEIN ESXM)
(SEQ ID NO: 17)
atggcctcacgttttatgacggatccgcatgcgatgcgggacatggcgggccgttttgag gtgcacgcccagacggtggaggacgaggctcgccggatgtgggcgtccgcgcaaaacatt tccggtgcgggctggagtggcatggccgaggcgacctcgctagacaccatgacctagatg aatcaggcgtttcgcaacatcgtgaacatgctgcacggggtgcgtgacgggctggttcgc gacgccaacaactacgaacagaagagcaggcctcccagcagatcctgagcagctag ESXP (ESAT-6 LIKE PROTEIN 7)
(SEQ ID NO: 18)
atggcaacacgttttatgacggatccgcacgcgatgcgggacatggcgggccgttttgag gtgcacgcccagacggtggaggacgaggctcgccggatgtgggcgtccgcgcaaaacatc tcgggcgcgggctggagtggcatggccgaggcgacctcgctagacaccatggcccagatg aatcaggcgtttcgcaacatcgtgaacatgctgcacggggtgcgtgacgggctggttcgc gacgccaacaactacgagcagcaagagcaggcctcccagcagatcctcagcagctaa ESXW (ESAT-6 LIKE PROTEIN 10)
(SEQ ID NO: 19)
atgacctcgcgttttatgacggatccgcacgcgatgcgggacatggcgggccgttttgag gtgcacgcccagacggtggaggacgaggctcgccggatgtgggcgtccgcgcaaaacatt tccggcgcgggctggagtggcatggccgaggcgacctcgctagacaccatgacccagatg aatcaggcgtttcgcaacatcgtgaacatgctgcacggggtgcgtgacgggctggttcgc gacgccaacaactacgaacagaagagcaggcctcccagcagatcctcagcagctga PE9 (PE FAMILY PROTEIN)
(SEQ ID NO: 20)
atgtcatacatgattgccacaccagcggcgttgacggcggcggcaacggatatcgacggg attggctcggcggttagcgttgcgaacgccgcggcggtcgccgcgacaaccggagtgctg gccgccggtggcgatgaagtgttggcggccatcgctaggctgttcaacgcaaacgccgag gaatatcacgccctcagcgcgcaggtggcggcgtttcaaaccctgtttgtgcgcaccttg actgggggtgcggagtctttcgccggcgccgaggccgccaatgcgtcacagctgcagag catcgcgcggcaggtgcggggcgccgtcaacgccgtcgccggtcaggtgacgggcaatgg cggctccggcaacagcggcacttcggctgcggcggccaacccgaattccgacaacacagc Gagcatcgccgatag PE_PGRS42 (PE-PGRS FAMILY PROTEIN)
(SEQ ID NO: 21)
gtgtcgttggtgatcgcgacgccgcagctgctggcaactgcggctttggatttagcgagt attggttcgcaggtgagcgcggctaatgcggccgcgggcgatgccgacgacggaagtggtg gctgcggctgccgatgaagtgtcggcggcgattgcggggttgttcggggcccatgctcgg cagtatcaggcgctcagcgtacaggtggcagcgtttcacgagcagtttgtgcaggcgttg -continued actgcggccgcgggtcggtatgccagcactgaggccgctgttgagcggagtctgctggt
gcggtgaatgcgccaccgaggcgcttttggggcgcccgttgatcggaaacggcgccgac
gggacggcacccgggcagcctggcgcggccggcgggttgctgtttggcaacggtggcaac
ggcgcggctggcgggttcggtcaaaccggcggcagcggaggcgcggccgggttgatcggc
aacggcggcaacggcggggccggtggtaccggcgcggccggcggtgccggtgggaacggg
gggtggttgtggggcaacggcggcaacggcggtgtcggcggcaccagcgtggccgcaggc
atcggggtgcgggcggtaacggcggcaacgccgggctgttcggccatggcggcgccggt
ggtaccggcggcgccggcctcgccggggcaaacgggtcaatcccacgcccggccccgcg
gccagcaccggggacagcccggcagatgtgtccggcatcggtgatcaaaccggcggcgac
ggcggcacgggcggccatggcactgccggcacgccgaccggtggcaccggcggcgacggt
gccaccgcgacggcaggctcgggcaaggccaccggcggtgccggtggtgacggcggtacc
gccgctgccggtggcggcggcggcaacggcggcgacggcggagtcgcgcagggcgacatt
gcgagcgcctttggcggtgatggtggcaacgggtccgacggtgtagccgccggcagtggg
ggtggtagcggcggcgccggaggcggcgctttcgtacacatcgccactgccacctctacc
ggtggtagcggcggtttcggtggtaacggggctgccagtgccgcctccggcgccgacggt
ggcgcaggggagctggcggcaatggtggcgccggcgggttgctattcggtgatggcggc
aacggtggcgccggtggcgcgggtggtatcggtggtgacggcgccacggggggcccggg
ggaagcggcggcaacgctggcatcgcgaggtttgacagcccagaccccgaggcagaaccc
gatgtggtcggcggcaagggtggtgatggcggcaagggcggcagcggccttggcgtcggc
ggcgccggcggggaccggcggcgcgggcggcaacggcggcgccggcgggttgttgttcggc
aacggcggcaacggcggcaacgccggggccggcggggatggcggcgccggcgttgccggt
ggggttggcggtaacgcggcggtggtggcaccgcgacgtttcacgaagacccggtcgct
ggtgtctgggcggtcggtggcgtaggtggtgatggtggctccggcggcagctcgcttggt
gtcggcggggtgggcggagccggtggcgtgggtggcaagggtggcgccagcggcatgttg
atcggcaacggcggcaacggtggcagcggcggagtcggtggggccggtggagtcggcggg
gctggcggtgacggcggcaacggcggctccggtggcaacgccagtacttttggcgatgag
aactccatcggcggggccggcgggacgggcggcaacggggggcaacggcgcaaacggcggt
aacggtggcgctggcggtattgccggcggtgcgggtgggtcggagggttcctcagcggt
gccgcaggagtcagcggcgctgacggtatcggtggcgcgggcggcgcaggcggtgccggt
ggcgcgggcggtagcggcggtgaggcaggcgcggggggcctcaccaacggccccgggtcc
cctggcgtttccggcaccgaaggcatggccggcgcgcccggctag Rv1860 (FIBRONECTIN ATTACHMENT PROTEIN)
(SEQ ID NO: 22)
atgcatcaggtggaccccaacttgacacgtcgcaagggacgattggcggcactggctatc
gcggcgatggccagcgccagcctggtgaccgttgcggtgccgcgaccgccaacgccgat
ccggagccagcgccccggtacccacaacggccgcctcgccgccgtcgaccgctgcagcg
ccacccgcaccggcgacacctgttgcccccccaccaccggccgccgccaacacgccgaat
gcccagccgggcgatcccaacgcagccacctccgccggccgacccgaacgcaccgccgcca
cctgtcattgccccaaacgcaccccaacctgtccggatcgacaacccggttggaggattc
agcttcgcgctgcctgctggctgggtggagtctgacgccgcccacttcgactacggttca
gcactcctcagcaaaaccaccggggacccgccatttcccggacagccgccgccggtggcc -continued

```
aatgacacccgtatcgtgctcggccggctagaccaaaagctttacgccagcgccgaagcc accgactccaaggccgcggcccggttgggctcggacatgggtgagttctatatgccctac ccgggcacccggatcaaccaggaaaccgtctcgctcgacgccaacggggtgtctggaagc gcgtcgtattacgaagtcaagttcagcgatccgagtaagccgaacggccagatctggacg ggcgtaatcggctcgcccgcggcgaacgcaccggacgccgggcccctcagcgctggttt gtggtatggctcgggaccgccaacaacccggtggacaagggcgcggccaaggcgctggcc gaatcgatccggccttttggtcgccccgccgccggcgccggcaccggctcctgcagagccc gctccggcgccggcgccggccggggaagtcgctcctaccccgacgacaccgacaccgcag Cggaccttaccggcctga
```

Rv1273c (PROBABLE DRUGS-TRANSPORT TRANSMEMBRANE ATP-BINDING PROTEIN ABC TRANSPORTER)

(SEQ ID NO: 23)

```
atgctcctggccctgctgcgccagcacatccgaccgtaccgccggctggtcgcgatgctg atgatgctgcagctggtcagcaccctggcttcgctatacctcccgacggtcaacgccgca atcgtcgacgacggcgtcgccaagggcgacaccgccaccatcgtacggctgggtgcggtg atgcttggggtgaccggattgcaggtgctgtgcgcgatcggggcggtctatctgggctcc cggaccggggcgggtttcggccgtgacctgcgctcggcaatgttcgaacacatcatcacc ttctcggaacgcgagaccgcccgattcggcgctccgacgttgttgacccgcagcaccaac gacgtccggcagatcctgttcctggtccagatgaccgccaccgtgctggtcaccgcaccg atcatgtgcgtcggcggaatcatcatggccatccaccaggaggccgcgctgacatggctg ctgctggtcagcgttccgattctggccgtagcaaactactggatcatctcccacatgctg ccgctcttccgccgcatgcagagcctgatcgacggcatcaacccgggtgatgcgcgatcag ctgtccggggtgcgagtggtccgcgccttcacccgcgaaggctatgaacgcgacaagttc gcgcaggccaatacggcgctgtcgaatgccgcactgagcgccggcaactggcaagcactg atgctgccggtgaccacgctgaccatcaacgcatccagcgtcgcactgatctggttcggt gggctacgcatcgacagcggccagatgcaggtcggctccctgatcgccttcctgtcctac ttcgcccagatcctgatggcggtgttgatggcgaccatgacgctggccgtgctgccacga gcgtcggtctgcgccgaacgcatcaccgaggtgcttccacgcccgccgcactcggtaac cccgacaatcccaagttcccgacggacggggtcacgggcgtagtgcgcttggctggcgca acctttacctatcctggcgccgactgcccggtgctgcaggacatttcgttgactgcgcgg cccggtaccaccaccgcgatcgtcggcagtaccggttcgggcaagtcgacactggtgtcg ttgatctgccggctctacgacgtcaccgctggcgcggtcttggttgacggtatcgacgtc cgcgagtaccacaccgagcggctctggtcagcgatcgggctggtgccccagcgcagctac ctcttctccggaaccgtcgcggacaacctgcgctacggcgggggcccagaccaggtagtc accgagcaggagatgtgggaggcgctgcgggtcgccgcggccgacggctttgtacaaaca gacgggctgcagacgcgtgtcgcccaaggtggtgtcaacttctccggcgggcagcgccaa cggctggcgatagcccgagcggtcatccgacgtccggccatctatgtgttcgacgacgcg ttctccgcacttgacgtgcacaccgacgccaaagtccacgcatcgctgcgacaggtatct ggtgatgcaaccatcattgttgttacacaacggatttcgaatgccgctcaggccgaccag gtcatcgttgtcgataacggtaagatcgtcggcacgggcacccacgaaacgctgctggcc gattgccccacctatgccgaattcgccgcctcacaatcgctgagcgccacggtcggggt Gtagggtga
```

-continued

Rv0159c (PE FAMILY PROTEIN)

(SEQ ID NO: 24)

atgtcctacgtcatcgcggccccggagatgttggcaacgacggccgcggacgtggacggg atcggttcggcgatacgagcggccagcgcgtccgctgcgggtccaacgaccggactgctg gccgcggccgccgatgaggtgtcgtcggccgctgcagcgctgttcagcgaatacgcgcgc gaatgtcaagaggtcctaaagcaggctgcggcgttccatggcgagttcacccgggcgctg gctgccgccggggccgcctatgcccaggctgaagccagcaacaccgctgctatgtcgggc accgccgggtccagcggcgccctcggttctgtcgggatgctgtcaggcaacccgctaacc gcgttgatgatgggcggcaccggggaaccgatccttagtgaccgcgtcttggcgatcatt gacagcgcatacattcggcccattttcgggcccaacaacccggtcgcccagtacacgccc gagcagtggtggccgtttatcgggaacctgtcactggaccaatccatcgcccagggtgtc acgctgctgaacaacggcatcaacgcggaactacaaaatgggcatgacgtcgtcgttttc ggctactcgcaaagcgccgcggtagcgaccaatgaaatacgcgctcttatggcgttacca ccggggccaagccccagatccaagccggctggctttcacgttgatcggtaatatcaataac cccaacggcggcgtcctcgagcgttacgtgggcctttacctcccgttcttggatatgtcg ttcaacggtgcgactccaccggattcccctaccagacctacatgtacaccggccaatac gacggctacgcccacaacccgcagtacccgctcaatatcttgtcggacctcaacgccttc atgggcatcagatgggtgcacaacgcgtaccccttcaccgcggccgaggttgccaatgcc gtgccgttgcccacgtctccgggctacaccggcaacacccattactacatgtttctgacc caggacctgccgctgttgcagccgattcgcgccatcccttcgtagggaccccaatagcc gagctgattcagcccgacctacgggtgctagtcgacttgggctatggctacggctacgcc gacgtacccaccccggccagcctgttcgcgccaatcaacccgatcgcgtggcctcggcc ctggcgaccgggaccgtgcaaggcccccaagccgccctagtaagcatcggattgttaccg cagtccgcgctacccaatacgtatccgtatcttccgtcggcgaatccgggcctgatgttc aacttcggtcaatccagtgtgacggagttgtcggtgctcagtggcgccctcgggtccgta gcgagattgattccaccgatcgcgtga Rv3350c (PPE FAMILY PROTEIN)

(SEQ ID NO: 25)

atggagtttccggtgttgccaccggaaatcaactccgtgctgatgtattcgggtgcgggg tcgagcccgttgctggcggcggccgcggcgtgggatgggctggctgaggagttggggtcg gcggcggtgtcgtttgggcaggtgacgtcgggcctgacggcgggggtgtggcagggtgcg gcggcggcggcgatggcggccgcggcggcgccgtatgcggggtggttgggttcggtggcg gccgcggccgaggcggtggccgggcaggcgcgggtggtggtgggggtctttgaggcggcg ttggcggcgacggtggatccggcgctggtggcggccaaccgggcgcggctggtggcgttg gcggtgtcgaatctgttggggcagaacacgccggcgatcgcggccgccgaggccgagtac gagctgatgtgggccgccgatgtggcggcgatggccggctaccattccggcgcgtcggct gctgccgcggcgttgccggcgttcagcccaccggcgcaggcgctggggggaggtgtcggc gcgttccttaccgccctgttcgccagccctgcgaaggcgctgagcctgaatgcgggtttg ggcaatgtcggcaattacaacgtcgggttgggcaatgtcggggtgttcaacctgggcgcg ggcaatgtgggtgggcagaatctgggtttcggaatgccggtggcaccaatgtcgggttc ggcaacctcggtaacgggaatgtcgggttcggcaactccggtctgggggcgggcctggcc ggcttgggcaatatcgggttggcaatgcgggcagcagcaactatggtttcgcaaacctg ggtgtgggcaacatcggtttcggcaacaccggcaccaacaacgtcggcgtcgggctcacc -continued

```
ggcaaccacctgacgggtatcgggggcctgaattcgggcaccgggaatatcgggttgttc aactccggcaccgggaatgtggggttcttcaattcggggaccgggaacttcggggtgttc aactcgggtaattacaacaccggtgtcggtaatgcggggacggccagcacggggttgttc aatgccggcaattcaacaccggcgtggtgaacgtgggcagttacaacaccggcagtttc aacgccggcgacaccaacaccggtggcttcaaccccggcggtgtgaacaccggctggctg aacaccggcaacaccaacaccggcatcgccaactcgggcaacgtcaacaccggcgcgttc atctcgggcaacttcaacaacggcgtgctgtgggtgggtgactaccagggcctgttcggc gtctccgccggctcgtcgatcccgcaattcccatcggcctggtgctcaacggcgacatc ggcccgatcaccatccagcccatcccgatcctgcccaccatcccgctcagcattcaccaa accgtcaacttgggcccgctggtggttcccgacatcgtgatcccgccttcggcggcggt atcggcatacccatcaacatcggcccgctgaccatcacacccatcaccctgtttgcccaa cagacatttgtcaaccaattgccctttcccaccttcagtttagggaaaatcacaattcca caaatccaaacctttgattctaacggtcagcttgtcagctttatcggccctatcgttatc gacaccaccattcccggacccaccaatccacagattgatttaacgatcagatgggatacc cctccgatcacgctgttcccgaatggcatcagtgctcccgataatcctttggggttgctg gtgagtgtgtcgatcagtaacccgggctttaccatcccgggatttagtgttcccgcgcag ccgttgccgttgtcgatcgatatcgagggccagatcgacgggttcagcaccccgccgatc acgatcgatcgcatcccctgaccgtggggggcggggtcacgatcggccccatcacgatc cagggccttcatatcccggcggcgccgggagtggggaacaccaccacggccccgtcgtcg ggattcttcaactccggtgcggtggggtgtcgggtttcggcaacgtcggcgcgggcagc tcgggctggtggaaccaggcgccgagcgcgctgttgggggccggttcgggtgttggcaac gtgggcaccctgggctcggtgtgctcaacctgggctcagggatctcggggttctacaac accagcgtgttgcctttcgggacaccggcggcggtgtcgggcatcggcaacctgggccag cagctgtcgggggtgtcggcggcgggaaccacgctgcgctcgatgctcgccggcaacctc gggttggccaatgtgggcaacttcaacaccgggttcggaaatgtcggggacgtcaacctg ggtgcggccaacatcggtgggcacaacctgggcctgggcaatgtcggggacggcaacctg gggttggcaacatcggccatggcaacctggggtttgccaacttgggcctgaccgccggc gcggcggggtgggcaatgttggttttggcaatgccggcatcaacaactatggcttggcg aacatgggtgtgggcaatattgggtttgccaacaccggcacgggcaacatcgggatcggg ctggtcggggaccatcggaccgggatcgggggcttgaactccggcatcggcaatatcggg ttgttcaactccggcaccggcaacgtcgggttcttcaattccgggaccggcaacttcggc atcgggaactccggccgcttcaacaccgggatcggtaatagcggaacggccagcaccggg ctcttcaatgccggcagcttcagcaccggcatcgccaacactggtgactacaacacgggc agcttcaacgccggcgacaccaacaccggtggcttcaacccgggcggcatcaacaccggc tggttcaacaccgggcatgccaacaccgggttggccaacgcgggcaccttcggcaccggc gccttcatgacgggcgactacagcaacggcctgttgtggcggggcggctacgagggcctg gtcggcgtccgcgtcgggcccacgatctcccaattcccggtcaccgtgcacgcgatcggc ggggtgggcccgctgcatgtggcgcccgtcccggtacccgccgtgcacgtcgagatcacc gacgccaccgtcggcctgggtccgttcaccgtcccaccgatcagcattccctcacttccc atcgccagcatcaccggaagcgtggacctggccgcaaacaccatctcgccgattcgcgct
```

-continued

```
cttgacccgctcgccggttcgatagggcttttctcgagccgttccgcctcagtgaccca tttatcaccattgatgcgttccaagttgttgccggtgtcttgttcctagagaacatcatt gtgcccggcctcacggttagcggtcagatattggtcaccccgacaccaattcccctaacc ctcaacttggacaccacccegtggacgcttttcccgaatggtttcaccattcccgcgcaa accccgtgacggtgggtatggaggtcgccaacgacgggttcaccttcttcccgggtggg ctgacctttccgcgggcctccgccggggtcaccggactgtccgtggggctggacgcgttc acgctgttgcccgacgggttcaccctcgacaccgtgccggcgaccttcgacggcaccatc ctcatcggcgatatcccgatcccgatcatcgatgtgccggcggtgccggggttcggcaac accaccacggcccatcgtcggggttcttcaacaccggcggcggcggtggatcggggttc gccaacgtcggcgcgggcacgtcgggctggtggaaccagggggcacgacgtgttagcaggg gcgggctcgggagttgccaatgccggcacgctgagctcgggcgtgctgaacgtcggctcg gggatctccgggtggtacaacaccagcaccctgggagcgggcaccccggcggtggtctcg ggcatcggcaacctcggccagcagctgtcgggttcttggcaaatgggaccgtgctcaac cggagcccattgtcaatatcgggtgggccgatgtgggcgcgttcaacaccgggttgggc aatgtggggacctcaactggggtgcggccaacatcggcgcgcagaacctgggcctgggc aatctcggcagcgggaacgtcgggttcggcaacatcggtgccggcaacgtcgggttcgcc aactcgggtccggcggtgggcctggccggcctgggcaacgtggggttgagcaatgccggc agcaacaactggggctggccaacctgggtgtgggcaacatcgggttggccaacaccggc acgggcaacatcgggatcgggctggtcggcgactaccagaccggcatcggcggcctcaac tcgggtagtggcaatatcggattgttcaattccggcaccggcaatgtcgggttcttcaac accggcaccggcaacttcggactgttcaactccggtagtttcaacaccggcatcggtaat agcggaaccggcagtactgggctcttcaatgccggcaatttcaacaccggcatcgccaac cccgggtcgtacaacacgggcagcttcaatgtcggtgataccaacaccggtggtttcaac ccgggcgacatcaacaccggctggttcaacaccggcattatgaatacgggcacccgcaac accggcgccctcatgtcggggaccgacagcaacggcatgctgtggcgcggcgaccacgag ggcctgttcggcctgtcctatggcatcacgatcccgcaattcccgatccgcatcaccacg actggcggtatcggccccatcgtcatcccggacaccacgatccttccgccgctgcacctg cagatcaccggcgacgcggactacagcttcaccgtgcccgacatcccatccccgccatc cacatcggcatcaatgcgtcgtcaccgtcggcttcaccgccccggaagccaccctgctg tccgccctgaagaataacggtagcttcatcagcttcggccccatcacgctctcgaatatc gatattccgcccatggatttcacgttaggcctgcccgttcttggtcctatcacgggccaa ctcggaccaattcatcttgagccaatcgtggtggccgggatcggtgtgcccctggagatc gagcccatcccctggatgcgatttcgttgagtgagtcgattcctatccgcatacctgtt gatattccggcctcggtcatcgatgggatttcaatgtcggaagtggtgccgatcgatgcg tccgtggacatcccggcggtcacgatcacaggcaccaccatttccgcgatcccgctgggc ttcgacattcgcaccagtgccggacccctcaacatcccgatcatcgacatcccggcggcg ccgggcttcgggaactcgacccagatgccgtcgtcggggttcttcaacaccggtgccggc ggcggatcgggcatcggcaacttgggtgcgggcgtgtcgggcctgctcaaccaggccggc gcggggtcactggtggggacactctcggggctgggcaatgccggcaccctggcctcgggt gtgctgaactccggcaccgccatctccgggctgttcaacgtgagcacgctggacgccacc accccggcggtgatctcggggttcagcaacctcggcgaccatatgtcggggggtgtccatc
```

-continued gatggcctgatcgcgatcctcaccttcccacctgccgagtccgtgttcgatcagatcatc gacgcggccatcgccgagctgcagcacctcgacatcggcaacgctttggccttgggcaat gtcggcggggtgaacctcggtttggctaacgtcggtgagttcaacctgggtgcgggcaac gtcggcaacatcaacgtcggcgccggcaacctcggcggcagcaacttggggttgggcaac gtcgggaccggcaacctcgggttcggcaacatcggtgccggcaatttcggattcggcaac gcgggcctgaccgcgggcgcgggggggcctgggcaatgtggggttgggtaacgccggcagc ggcagctgggggttggccaacgtgggtgtgggcaatatcgggttggccaacaccggcacc ggcaacatcgggatcgggctgaccggggactatcggaccgggatcggcggcctgaactcg ggcaccgggaacctcgggttgttcaactcgggcaccggcaacatcgggttcttcaacacc gggaccgggaacttcggctgttcaactcgggcagttacagcaccggtgtggggaatgcg ggcacggccagcaccgggttgttcaacgcggggaacttcaacaccggtctggccaatgcc ggctcctacaacaccggcagcctcaacgtgggcagcttcaacaccggcggcgtcaacccg ggcaccgtcaacaccggctggttcaacaccggccacaccaacaccggcctgttcaacacc ggcaacgtcaacaccggcgcgttcaactccggcagcttcaacaacggggcgctgtggacc ggtgactaccacgggctggtcggcttctccttcagcatcgacatcgccggcagcaccctg ctggacctcaacgaaaccctcaacctgggcccatccacatcgagcagatcgacatcccc ggcatgtcgctgttcgacgtccacgaaatcgtcgagatcggaccctcaccatcccgcag gtcgatgttcccgcgataccgctagagatccacgaatcgatccacatggatcccatcgtc ctggtgcccgccaccacaattcccgcacagacgagaaccattccgctggacatccccgcc tcacccgggtcaaccatgacgcttccgctcatcagcatgcgcttcgaaggcgaggactgg atcctcgggtcgaccgcggcgattcccaatttcggagacccctccgggcgcccacccag ggcatcaccattcacaccggccctggccccggaacgaccggcgagctcaagatatctatt ccgggtttcgagattccgcaaatcgctaccacgagattcctgttggacgtgaacatcagc ggtggtctgccggccttcaccttgttcgcgggtggcctgacgatccccacgaacgccatc ccgttaacgatcgatgcgtccggcgcgctggatccgatcacgattttcccgggtgggtac acgatcgacccgctgccgctgcacctggcgctgaatctcaccgtgcccgacagcagcatc ccgatcatcgatgtcccgccgacgccagggttcggcaacaccacggcgaccccgtcgtcg gggttcttcaactccggcgccggtggggtgtcggggttcggaaacgtcgggtcgaacctg tcgggctggtggaaccaggcggcgagcgcgctggcggggtcgggatcgggggtgttgaat gtcggcacgctgggctcgggtgtgctcaacgtcggctcgggtgtctcggggatctacaac accagcgtgttgccgctcgggacgccggcggtgctgtcgggcctcggcaacgtcggccat cagctgtcgggcgtgtctgcggccgggaccgcgttgaaccagatccccatcctcaacatc gggttggcggatgtgggcaacttcaacgtcgggttcggcaacgtcggggacgttaacctg ggcgcggccaacctcggtgcgcaaaacctggggctgggcaacgtcggcaccggcaacctc ggcttcgccaacgtcggccacggcaatatcggtttcggcaattcgggtctgaccgccggc gcggccggcctgggcaacacggggttcggcaatgccggcagcgccaactatggtttcgcc aaccagggcgtgcgcaacatcgggttggccaacaccggcaccggcaacatcgggatcggg ctggtgggggacaacctcaccggcatcgggggcctgaactccggtgccggcaatatcggc ttgttcaactccggcaccggcaacatcgggttcttcaactccgggaccggcaacttcggc atcggtaactcgggcagcttcaacaccggcatcggcaatagcggaacgggcagcactggg -continued

```
ctcttcaatgccggcagcttcaacaccggcgtggccaacgccggcagctacaacaccggc atcttcaatgccggcgacaccaacaccggggggttcaacccgggcaccatcaacaccggc tggttcaacaccggccacaccaataccggcatcgccaactcgggcaacgtcggcaccggc gcgttcatgtcgggcaacttcagcaacggcctgttgtggcggggtgatcacgagggcctg ttcagcctgttctacagcctcgacgtgccccggatcaccatcgtggacgcccacctcgac ggcggcttcggacccgtggtcctcccgcccatcccggtgccggccgttaatgcgcacctg accggaaacgtcgcgatgggcgcattcaccattccgcagatcgacatccccgcactcacc ccaaacatcaccggaagcgccgccttccgcatcgttgtgggtccgtgcgcattccgccg gtgagtgtcattgtggagcaaataatcaacgcctcggttggggcggagatgaggatagat cccttcgaaatgtggactcaaggcactaatggccttggtataaccttctattcattcgga tcggccgacggttcgccctacgccaccggcccactcgttttcggcgccggcacgagcgac ggaagccatctcaccatttccgcgtccagcggggcgtttaccactccgcagctcgaaact ggcccgatcacgttgggcttccaggtgccggcagcgtcaacgcgatcaccctcttcccc ggtggtttgacgttcccggcgacctcgctgctgaacctggacgtgaccgccggcgccggc ggcgtggacatcccggccatcacctggcccgagatcgcggcgagcgccgacggctcggtg tatgtcctcgccagcagcatcccgctgatcaacatcccgcccaccccgggcattgggaac agcaccatcaccccgtcgtcgggcttcttcaacgccggcgcgggcggggatcgggcttc ggcaacttcggcgcgggcacctcgggctggtggaaccaggcgcacaccgcgctggcgggg gcgggctcgggttttgccaacgttggcacgctgcattccggtgtgctcaacctgggctcg ggtgtctcggggatctacaacaccagcacgctgggggtggggaccccggcgctggtctca ggcctgggcaacgtcggccaccaactgtcggggctgctttccggcgggtccgcggtgaac ccggtgaccgttctgaatatcgggttggccaacgtcggcagccacaacgccggtttcggc aatgtcggggaggtcaacctgggcgcggccaacctcggcgcgcacaacctgggcttcgga aatatcggcgccggcaacctggggttcggcaatattggccacggcaatgtcggagtcggc aactcgggtctgaccgcgggcgtgccgggcctgggcaatgtggggttgggcaatgccggc ggcaacaactgggggttggccaacgtgggcgtgggcaatatcgggttggccaacaccggc accggcaacattgggatcgggctgaccggcgactaccagaccggcatcggcggcctaaat tccggtgccggcaacctggggttgttcaactccggcgccggcaacgtcgggttcttcaac accgggaccggcaacttcgggttgttcaactccggcagcttcaacaccggcgtcggcaat agcggaacgggcagcactgggctcttcaatgccggcagtttcaacaccggtgtggccaac gccggcagctacaacacgggcagcttcaatgtcggtgacaccaacaccggggggcttcaac ccgggcagcatcaacaccggctggctcaacgccggcaacgccaacaccggggtggccaac gcgggcaatgtcaacaccggcgccttcgtcaccggcaacttcagcaacggcatcctgtgg cgcggcgactaccagggcctggccggcttcgccgtgggctacaccctcccgctgttcccc gcggtgggcgccgacgtcagcggcgggatcggcccgattaccgtgctgccgcccatccac atcccgcccattccggtcggcttcgccgcggtcggtggcatcggcccgatcgccatcccg gacatctctgttccatccattcacttgggcctcgaccccgccgtccatgtcggctccatc accgtcaaccccattaccgtcaggaccccgcccgtgctcgtcagttactcccaaggagcc gtcaccagcacgtccggaccaacctcagagatttgggtcaagcccagcttcttccccgga atccggatcgcgccctctagcggcgggggtgcaacgtccacgcaaggggcatactttgtg gggcccatctccatcccctccggcacggtgaccttcccgggattcaccatcccctcgac
```

-continued

```
ccgatcgacatcggcctgccggtgtcgctgaccatcccggggttcaccatcccgggcggc accctgatccccaccctcccgctgggcctcgcgttgtccaatggcatcccgcccgtcgac atcccggccatcgttctcgaccggatcttgctggacctgcacgccgacaccactatcggc ccgatcaacgtcccgatcgccgggttcggcggggcgccgggtttcgggaactcgaccacg ctgccgtcgtcgggcttcttcaacaccggagctggcggcggttcgggctttagcaacacc ggcgcgggcatgtcgggattgctcaacgcgatgtcggatccgctgctcgggtcggcgtcg ggcttcgccaacttcggcacccagctctccggcatcctcaaccgcggcgccggcatctcg ggcgtgtacaacaccggcgcgctgggtgttgtcaccgcggccgtcgtctcgggtttcggc aacgtcggccagcaactgtcgggcttgctcttcaccggcgtcgggccctaa
```

These polynucleotides include DNA, cDNA and RNA sequences which encode the polypeptide of interest. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, Biochemistry, $3^{rd}$ Edition, W.H. Freeman and Co., NY).

A nucleic acid encoding an Mtb polypeptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, NY, 1989). Polynucleotides also can be isolated by screening genomic or cDNA libraries with probes selected from the sequences of the desired polynucleotide under stringent hybridization conditions.

The polynucleotides encoding an Mtb polypeptide include a recombinant DNA which is incorporated into a vector into an autonomously replicating plasmid or virus or into the genomic DNA of a prokaryote or eukaryote, or which exists as a separate molecule (such as a cDNA) independent of other sequences. The nucleotides of the invention can be ribonucleotides, deoxyribonucleotides, or modified forms of either nucleotide. The term includes single and double forms of DNA.

In one embodiment, vectors are used for expression in yeast such as *S. cerevisiae* or *Kluyveromyces lactis*. Several promoters are known to be of use in yeast expression systems such as the constitutive promoters plasma membrane $H^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, may inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2μ) or single copy (CEN) plasmids to give an additional level of control in expression level. The plasmids can include nutritional markers (such as URA3, ADE3, HIS1, and others) for selection in yeast and antibiotic resistance (AMP) for propagation in bacteria. Plasmids for expression on *K. lactis* are known, such as pKLAC1. Thus, in one example, after amplification in bacteria, plasmids can be introduced into the corresponding yeast auxotrophs by methods similar to bacterial transformation.

The Mtb polypeptides can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in a yeast lacking the master vacuolar endopeptidase Pep4, which controls the activation of other vacuolar hydrolases. Heterologous expression in strains carrying temperature-sensitive (ts) alleles of genes can be employed if the corresponding null mutant is inviable.

Viral vectors can also be prepared encoding the Mtb polypeptides disclosed herein. A number of viral vectors have been constructed, including polyoma, SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. No.

5,091,309 and U.S. Pat. No. 5,2217,879), alphaviruses (S. Schlesinger, 1993, Trends Biotechnol. 11:18-22; I. Frolov et al., 1996, Proc. Natl. Acad. Sci. USA 93:11371-11377) and retroviruses of avian (Brandyopadhyay et al., 1984, Mol. Cell. Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell. Biol., 5:431-437; Sorge et al., 1984, Mol. Cell. Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

Viral vectors, such as poxyiral vectors, that encode an Mtb polypeptide include at least one expression control element operationally linked to the nucleic acid sequence encoding the Mtb polypeptide. The expression control elements are inserted in the viral vector to control and regulate the expression of the nucleic acid sequence. Examples of expression control elements of use in these vectors includes, but is not limited to, lac system, operator and promoter regions of phage lambda, yeast promoters and promoters derived from polyoma, adenovirus, retrovirus or SV40. Additional operational elements include, but are not limited to, leader sequence, termination codons, polyadenylation signals and any other sequences necessary for the appropriate transcription and subsequent translation of the nucleic acid sequence encoding the Mtb polypeptide in the host system. The expression vector can contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in "Current Protocols in Molecular Biology," John Wiley and Sons, New York, N.Y.) and are commercially available.

DNA sequences encoding an Mtb polypeptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

As noted above, a polynucleotide sequence encoding an Mtb polypeptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

Hosts cells can include microbial, yeast, insect and mammalian host cells. Methods of expressing DNA sequences having eukaryotic or viral sequences in prokaryotes are well known in the art. Non-limiting examples of suitable host cells include bacteria, archea, insect, fungi (for example, yeast), mycobacterium (such as *M. smegmatis*), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, Jakoby and Pastan (eds), 1979, Cell Culture. Methods in Enzymology, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although cell lines may be used, such as cells designed to provide higher expression desirable glycosylation patterns, or other features. As discussed above, techniques for the transformation of yeast cells, such as polyethylene glycol transformation, protoplast transformation and gene guns are also known in the art (see Gietz and Woods Methods in Enzymology 350: 87-96, 2002).

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding an Mtb polypeptide, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Numerous other assay protocols exist that are suitable for use with the polypeptides of the present inidisclosure. The above descriptions are intended to be exemplary only.

The disclosure is illustrated by the following non-limiting Examples.

EXAMPLES

For many infections, the repertoire of the CD8 response is shaped by the entry of antigen into the MHC-I processing pathway, binding of peptides and/or non-peptide antigens to MHC-I molecules, and recognition of these structures by T cells. Ultimately, a relatively limited subset of pathogen-specific T cells emerge. While a number of commonly recognized CD4 Mtb antigens have been described (Reed et al., *Microbes Infect* 7:922-931, 2005) (ESAT-6, CFP10, Ag85, etc.), surprisingly little is known about common Mtb antigens recognized by human $CD8^+$ T cells. The majority of CD8 epitopes that have been identified were defined by testing of Mtb peptides selected for high affinity binding to MHC Class Ia molecules (HLA-A2 in most cases (see, for example, Lalvani, *Microbes Infect* 7:922-931, 1998). In almost all of these, however, the ex vivo frequency of these T cells in Mtb-infected individuals is low or undetectable, suggesting that these specificities may not represent immunodominant responses. In contrast, in the limited cases in which T cells have been used to define epitopes contained in selected Mtb antigens, high ex vivo frequencies have been demonstrated (see Lewinsohn et al., *Am J Respir Crit Care Med* 166:843-848, 2002), suggesting, that a T cell-centered approach can identify immunodominant epitopes. Moreover, CD8 T cell responses to some Mtb antigens which represent good CD4 antigens (CFP10, ESAT-6, Ag85, and Mtb39) have been detected at high frequency in persons infected with Mtb. Therefore, a limited library of overlapping synthetic peptides representing several known CD4 Mtb antigens was used to determine the magnitude of the CD8 response to these antigens in persons with active tuberculosis (TB) and latent tuberculosis infection (LTBI) as well as uninfected subjects. Furthermore, a panel of Mtb-specific CD8+ T cell clones was utilized to define minimal epitopes recognized within these antigens and determined the contribution of these novel epitopes to the ex vivo Mtb-specific CD8 response.

Example 1

Materials and Methods

Human Subjects.

Uninfected individuals were defined as healthy individuals with a negative tuberculin skin test (TST) and no know risk factors for infection with Mtb. Individuals with LTBI were defined as healthy persons with a positive TST and no symptoms and signs of active TB. In all active TB cases, pulmonary TB was diagnosed by the TB Controller of the county and confirmed by positive sputum culture for *Mycobacterium tuberculosis*. Peripheral blood mononuclear cells (PBMC) were isolated from whole blood obtained by venipuncture or apheresis.

Media and Reagents.

Culture medium consisted of RPMI 1640 supplemented with 10% Fetal Bovine Sera (FBS; Bio Whittaker), $5 \times 10^{-5}$ M 2 ME (Sigma-Aldrich), and 2 mM glutamine (GIBCO BRL). For the growth and assay of Mtb-reactive T cell clones, RPMI 1640 was supplemented with 10% human serum. Mtb strain H37Rv was obtained from the American Type Culture Collection (Rockville, Md.) and prepared as previously described (Lewinsohn et al., *J Immunol* 165:925-930, 2000). Peptides were synthesized by Genemed Synthesis, Inc, (San Francisco, Calif.). Synthetic peptide pools consisted of 15-mers overlapping by 11 amino acids (aa) representing Mtb proteins demonstrated to be potent CD4 antigens. Peptide pools representing CFP-10 (Berthet et al., *Microbiology* 144: 3195-3203, 1998; Dillon et al., *J Clin Microbiol* 38:3285-3290, 2000), ESAT-6 (Sorenson et al., *Infect Immun* 63:1710-1717, 1995), Mtb39a (two pools, A &B, reference) (Dillon et al., *Infect Immun* 67:2941-2950, 1999), Mtb8.4 (Coler et al., *J Immunol* 161:2356-2364, 1998), Mtb 9.9 (Alderson et al., *J Exp Med* 191:551-560, 2000), (Coler et al., *J Immunol* 161: 2356-2364, 1998), Mtb 9.9 (Alderson et al., *J Exp Med* 191: 551-560, 2000), EsxG (Rosenkrands et al., *Electrophoresis* 21:3740-3756, 2002), 19 kDa antigen (Collins et al. *J Gen Microbiol* 136:1429-1436, 1990), antigen 85b (Borremans et al., *Infect Immun* 57:3123-3130, 1989) (two pools, A & B, reference) were synthesized. Peptides were resuspended in DMSO and up to 50 peptides were combined into one pool such that each peptide in the pool was at a concentration of 1 mg/ml. Peptide pools were stored at −80° C.

Cell Lines and T Cell Clones.

EBV-transformed B cell lines, LCL, were either generated using supernatants from the cell line 9B5-8 (American Type Culture Collection) or obtained from the National Marrow Donor Program (NMDP; Minneapolis, Minn.). LCL were maintained by continuous passage as previously described (Heinzel et al., *J Exp Med* 196:1473-1481, 2002). Mtb-specific T cell clones were isolated from individuals with LTBI or active tuberculosis, using Mtb-infected DCs as APCs and limiting dilution cloning methodology as previously described (Lewinsohn et al., *J Immunol* 165:925-930, 2000). Briefly, CD8+ T cells were isolated from PBMC using negative selection using CD4 antibody-coated beads and then positive selection using CD8 antibody-coated magnetic beads per the manufacturer's instructions (Miltenyi Biotec, Auburn Calif.) or via flow cytometry. In this case, CD4-PE (BD Biosciences cat #555347) negative, CD8-APC (BD Biosciences, cat#555369) positive cells (purity >99%) were sorted on a Becton Dickenson LSR II. T cells were seeded at various concentrations in the presence of a $1 \times 10^5$ irradiated autologous Mtb-infected DC, generated as described below, and rIL-2 (5 ng/ml) in cell culture media consisting of 200 μl of RPMI 1640 supplemented with 10% human sera. Wells exhibiting growth between 10-14 days, were assessed for Mtb specificity using ELISPOT and Mtb-infected DC as a source of APCs. T cells retaining Mtb specificity were further phenotyped for αβ T cell receptor expression and CD8 expression by FACS and expanded as described below. Vβ usage was determined using the IOTest Beta Mark Kit from Beckman Coulter.

Expansion of T Cell Clones.

To expand the CD8+ T cell clones, a rapid expansion protocol using anti-CD3 mAb stimulation was used as described previously (Heinzel et al., *J Exp Med* 196:1473-1481, 2002).

Generation and Infection of Peripheral Blood DCs.

Monocyte-derived DCs were prepared (Heinzel et al., supra; Romani et al., *J Exp Med* 180:83-93, 1994). To generate Mtb-infected DC, cells ($1 \times 10^6$) were cultured overnight in the presence of Mtb (multiplicity of infection [MOI]=50:1). After 18 hours, the cells were harvested and resuspended in RPMI/10% human serum.

MHC Binding Assays.

The MHC-peptide binding assay utilized measures the ability of peptide ligands to inhibit the binding of a radiolabeled peptide to purified MHC molecules, and has been described in detail elsewhere (Sidney et al., 1999. UNIT 18.3 Measurement of MHC/peptide interactions by gel filtration. In Current Protocols in Immunology. Coligan et al., eds., John Wiley & Sons, Inc., 1996). Briefly, purified MHC molecules, test peptides, and a radiolabeled probe peptide were incubated at room temperature in the presence of human B2-microglobulin and a cocktail of protease inhibitors. After a two-day incubation, binding of the radiolabeled peptide to the corresponding MHC class I molecule was determined by capturing MHC/peptide complexes on W6/32 antibody (anti-HLA A, B, and C) or B123.2 (anti-HLA B, C and some A) coated plates, and bound counts per minute (cpm) were measured using a microscintillation counter. For competition assays, the concentration of peptide yielding 50% inhibition of the binding of the radiolabeled peptide was calculated. Peptides were typically tested at six different concentrations covering a 100.000-fold dose range, and in three or more independent assays. Under the conditions utilized, where [label]<[MHC] and $IC_{50} \geq [MHC]$, the measured $IC_{50}$ values are reasonable approximations of the true Kd values.

IFN-γ ELISPOT Assay.

The IFN-γ ELISPOT assay was performed as described previously (Beckman et al., *J Immunol* 157:2795-2803, 1996). For determination of ex vivo frequencies of CD4+ or CD8+ T cells responding to Mtb infection or Mtb antigens, CD4+ or CD8+ T-cells were positively selected from PBMC using magnetic beads (Miltenyi Biotec, Auburn Calif.) as a source of responder T cells and tested in duplicate at four different cell concentrations. Autologous DC (20,000 cells/well) were used as APC and DC were either infected with Mtb or pulsed with peptide pools (5 µg/ml, final concentration of each peptide) and then added to the assay. For assays using T cell clones, T cells (1000 or 5000 cells/well) were incubated with autologous LCL (20,000 cells/well) in the presence or absence of antigen.

Data Analysis:

To determine the ex vivo frequency of antigen-specific T cells, the average number of spots per well for each duplicate was plotted against the number of responder cells per well. Linear regression analysis was used to determine the slope of the line, which represents the frequency of antigen-specific T cells. The assay is considered positive, i.e. reflecting the presence of a primed T cell response, if the binomial probability (Lewinshon et al., Microbes Infect 8:2587-2598, 2006) for the number of spots is significantly different by experimental and control assays. To determine differences in ex vivo T cell frequencies between groups, Wilcoxon/Kruskal-Wallis analysis was used.

Example 2

Defining Immunodominant Mtb-Specific CD8+ Antigens

To define immunodominant Mtb-specific CD8+ antigens, and to determine whether or not these responses result from infection with Mtb, CD8+ T cells were used from donors uninfected, with LTBI, or actively infected with Mtb. Responses were determined either directly ex vivo, or using CD8+ T cell clones obtained by limiting dilution cloning on Mtb-infected autologous DC (Lewinsohn et al., J Immunol 165:925-930, 2000). As much is known about dominant CD4+ Mtb antigens, a panel of these commonly recognized antigens was selected for further evaluation. These were: Mtb39, CFP10, and Mtb8.4, Mtb9.9, ESAT-6, Ag85b, 19 kDa, and EsxG. To avoid bias introduced by using peptides of predicted HLA-binding specificity, overlapping peptides were synthesized (15 aa, overlap 11 aa) to represent the proteins of interest (Lewinshon et al., J Immunol 166:439-446, 2001).

To accurately determine the ex vivo effector cell frequencies of CD8+ T cells, linear regression analysis was used. As shown in FIG. 1, magnetic bead purified CD8+ T cells were tested against peptide pulsed DC over a range of CD8+ T cell numbers in an IFN-γ ELISPOT assay. A positive assay was determined as described below and if positive, the antigen specific frequency was determined using linear regression.

Figure 2:
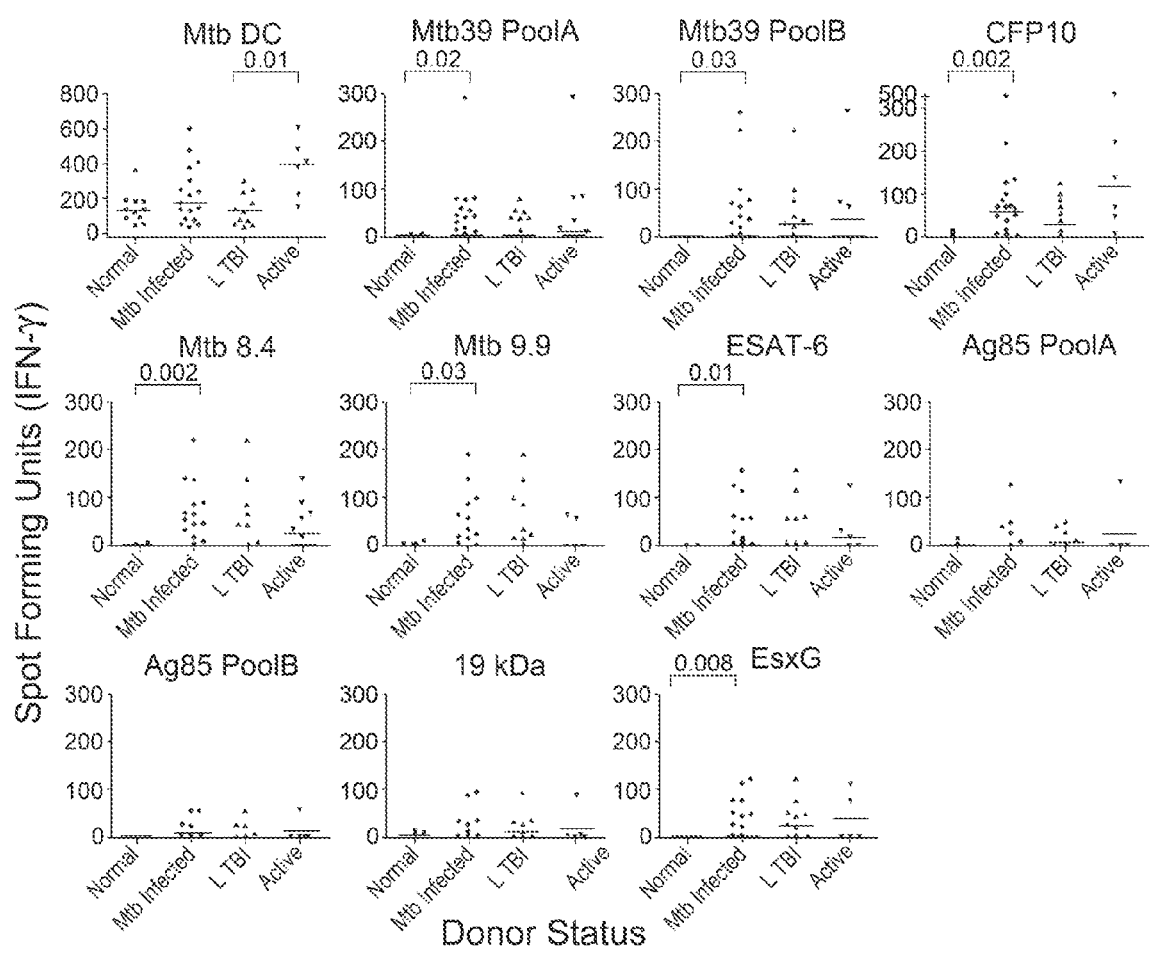
FIG. 2 is a set of graphs showing ex vivo CD8$^+$ T cell frequencies to Mtb antigens are associated with Mtb infection. As described above (see FIG. 1), to determine ex vivo CD8$^+$ T cell frequencies, autologous DC either infected with Mtb or pulsed with cognate peptide pools were incubated with CD8$^+$ T cells in an IFN-γ ELISPOT assay. Subjects without evidence for Mtb infection, those with LTBI, and those with active TB (culture confirmed pulmonary tuberculosis) were evaluated. "Mtb Infected" includes those with LTBI and active tuberculosis. P values are noted where P=<0.05 (Wilcoxon/Kruskal-Wallis).

Subjects uninfected (n=14), those with LTBI (n=20) and those with active TB (n=12) were evaluated for CD8+ responses to a panel of Mtb CD4+ T cell antigens, as well as to Mtb-infected DC. All subjects tested had robust CD8+ T cell responses to Mtb-infected DC and were of greater magnitude in individuals with active TB than in those with LTBI (p=0.01; FIG. 2, Table I). However, CD8+ T cell responses to the panel of Mtb antigens were found almost exclusively in those infected with Mtb in that statistically significant differences between uninfected and Mtb-infected individuals were noted for seven of ten antigens for both the magnitude of the response (FIG. 2) and the proportion of positive assays (Table I).

TABLE I

CD8+ T cell responses to known TB antigens.

| Antigen | Mtb Infected # positive[a]/ # tested (%) | Mtb Uninfected # positive[a]/# tested (%) | P value (2 tail fishers) |
|---|---|---|---|
| Mtb DC | 17/17 (100) | 11/11 (100) | |
| Mtb39 Pool A | 13/30 (43) | 0/14 (0) | 0.003 |
| Mtb 39 Pool B | 10/30 (33) | 0/14 (0) | 0.01 |
| CFP10 | 14/30 (47) | 1/14 (7) | 0.02 |
| Mtb 8.4 | 13/30 (43) | 0/14 (0) | 0.003 |
| Mtb 9.9 | 10/25 (40) | 1/14 (7) | 0.06 |
| ESAT 6 | 12/25 (48) | 0/14 (0) | 0.003 |
| Ag85b Pool A | 5/22 (23) | 1/14 (7) | 0.37 |
| Ag85b Pool B | 4/22 (18) | 0/14 (0) | 0.14 |
| 19 kd | 6/22 (27) | 1/12 (8) | 0.38 |
| EsxG | 9/22 (41) | 0/14 (0) | 0.006 |

[a]Positive assay defined in text.

However differences in CD8+ T cell responses between individuals with active TB and LTBI were not statistically different. While strong CD8+ T cell responses were observed against many of the antigens tested, it is equally notable that several subjects with strong Mtb directed CD8+ T cell responses did not have demonstrable responses to many of the antigens tested.

These ex vivo frequency data demonstrate the presence of high-frequency responses to a number of known Mtb antigens, but do not shed light on the restricting allele, minimal epitope, or dominance hierarchy within the gene of interest. To address this question, limiting dilution cloning of human CD8+ T cells using Mtb-infected DC was performed (see Lewinsohn et al., J Immunol 166:439-446, 2001), and panels of both classically and non-classically HLA-restricted CD8+ T cell clones were generated. Using peptide pools representing known CD4+ antigens, the antigenic specificity of the HLA-Ia restricted clones can be defined in more than half of the clones (Table II).

TABLE II

Many CD8+ T cell clones recognize known CD4+ T cell antigens

| Donor | Tb Status | HLA-Ia Clones (#)[a] | Antigen Identified (#)[b] | # Distinct Antigens (#)[c] | # Distinct Epitopes (#)[d] |
|---|---|---|---|---|---|
| D431 | Active TB | 1 | 0 | 0 | 0 |
| D432 | Active TB | 14 | 4 | 2 | 2 |
| D466 | Active TB | 11 | 10 | 1 | 2 |
| D571 | Active TB | 7 | 7 | 1 | 1 |
| D480 | Active TB | 6 | 6 | 1 | 1 |
| D481 | Active TB | 11 | 11 | 1 | 1 |
| D426 | LTBI | 1 | 0 | 0 | 0 |
| D443 | LTBI | 1 | 1 | 1 | 1 |
| D454 | LTBI | 2 | 2 | 2 | 2 |
| D504 | LTBI | 7 | 1 | 1 | 1 |
| Totals | | 61 | 42 | 10 | 11 |

[a]Number of clones derived from donor.
[b]Number of clones for which cognate antigen was identified.
[c]Total number of distinct antigens identified from the clone set.
[d]Total number of distinct epitopes identified from the clone set.

Figure 3A:
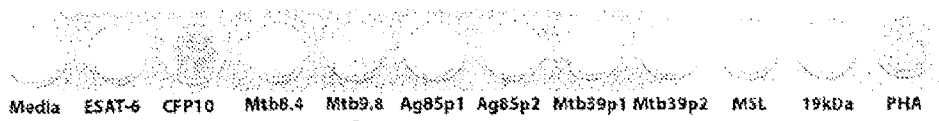
FIGS. 3a to 3d are a set of digital images showing the definition of Antigenic Specificity and HLA-Restriction (the characterization of T cell clone D466 D6). For the results shown in FIGS. 3a-3c, to Identify the antigen and minimal epitope recognized by T cell clone, D466 D6, T-cells (5000 cells/well) were incubated with autologous LCL (20,000/well) and 5 μg/ml of antigen. IFN-γ was assessed by ELISPOT after eighteen hours of co-culture. For the results presented in FIG. 3a, antigens consisted of peptide pools representing known CD4$^+$ antigens, made up of 15 amino acid (aa) peptides overlapping by 11 aa. For the results presented in FIG. 3b, antigens consisted of individual 15 aa CFP10 peptides that together constitute the peptide pool. For the results presented in FIG. 3c, antigens consisted of individual nested CFP10$_{1-15}$ peptides (10 aa, 9 aa or 8 aa), used to further map the epitope. For the results presented in FIG. 3d, the restricting allele was identified using LCL (20,000/well) expressing HLA alleles matching D466 at one or two alleles, pulsed with CFP10$_{2-10}$ (5 μg/ml) as APC. After 2 hours, cells were washed and incubated with T-cells (500 cells/well) in an IFN-γ ELISPOT assay.
Figure 3B:
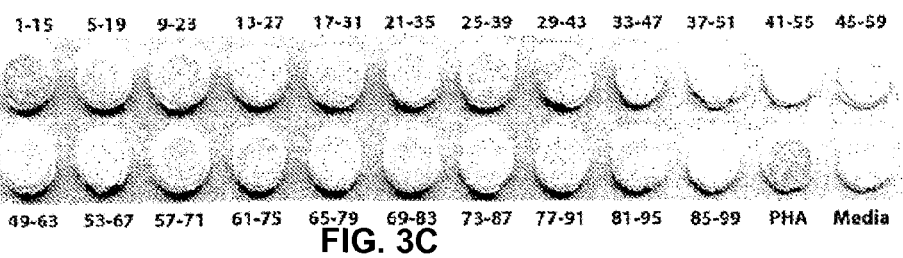
Figure 3C:
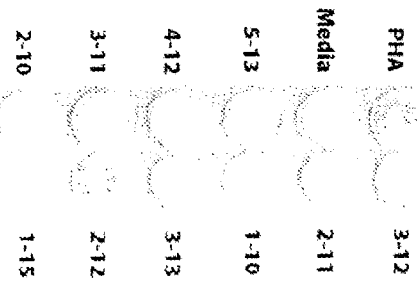
Figure 3D:
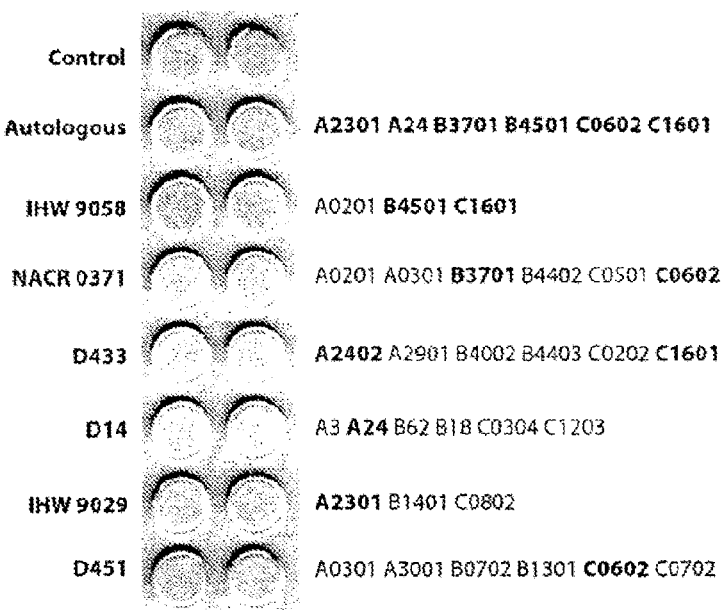
Figure 4:
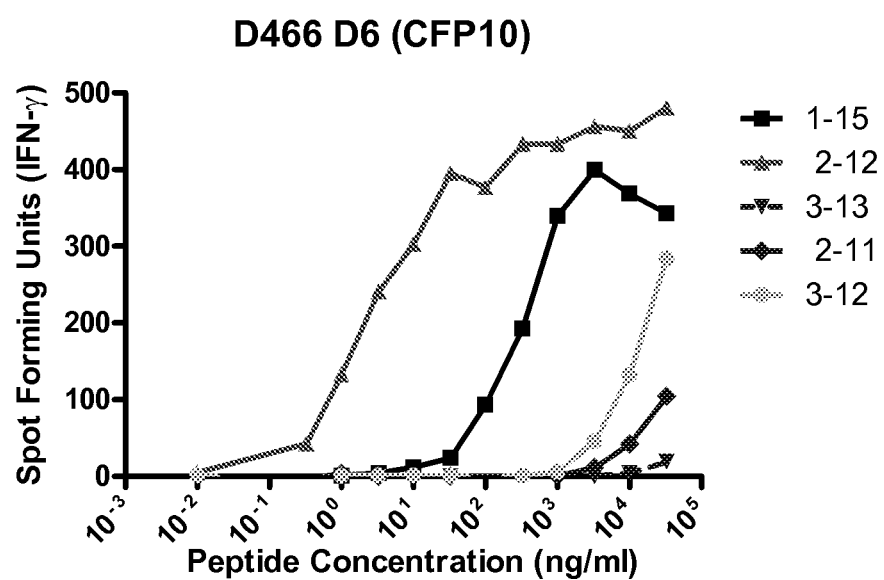
FIG. 4 is a line graph showing the confirmation of minimal epitope mapping of D466 D6. To confirm the minimal epitope, autologous LCL (20,000/well) was pulsed with peptide at the concentration indicated and co-cultured with T-cells (1000 cells/well). IFN-γ was assessed by ELISPOT after eighteen hours co-culture. Each point represents the mean of duplicate determinations.
Figure 5:
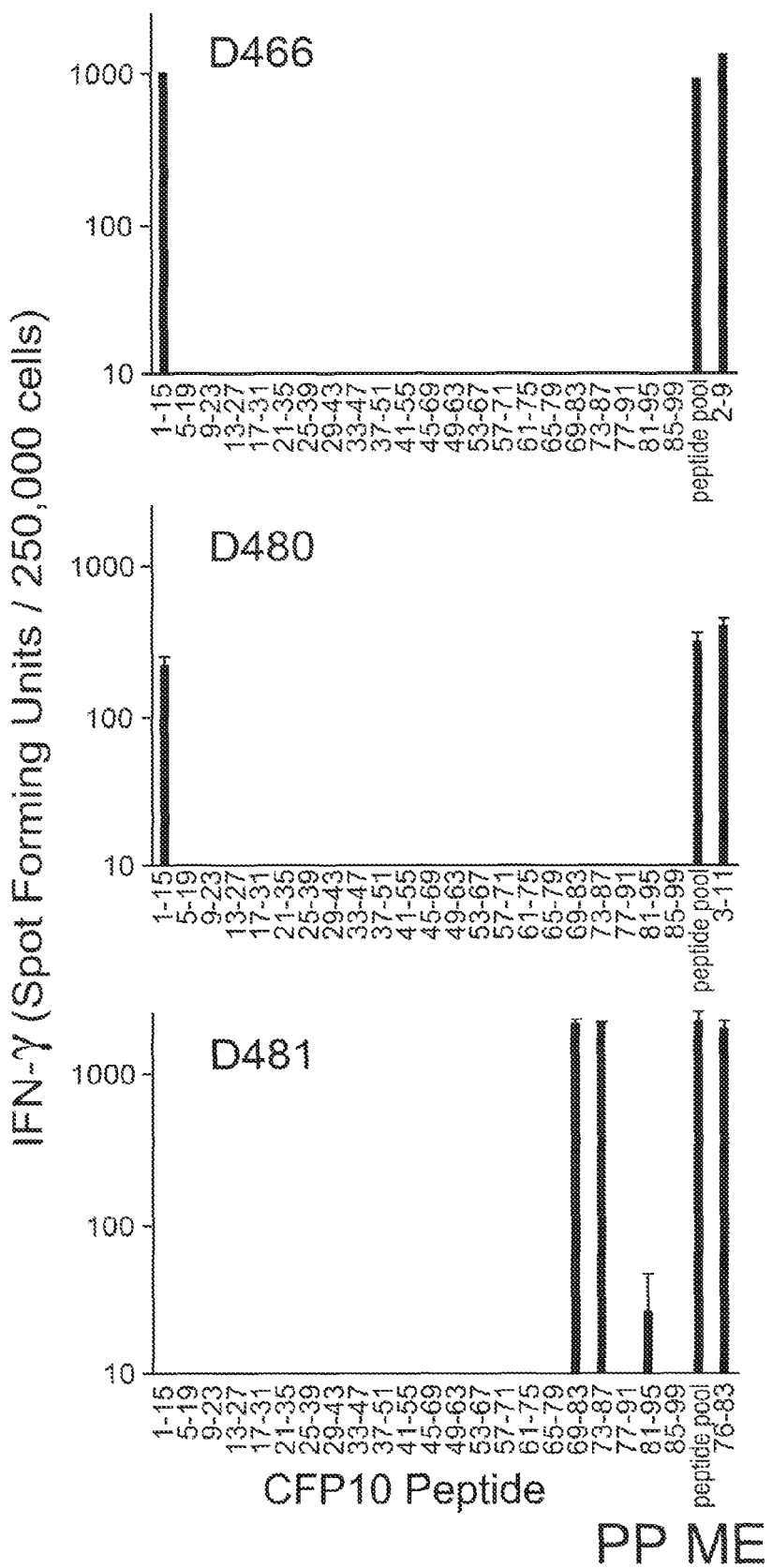
FIG. 5 is a set of bar graphs showing the profiling of immunodominance pattern for CFP10. To determine the effector cell frequencies, autologous DC (20,000/well) were pulsed either with each individual 15-mer peptide (5 μg/ml), the peptide pool (PP; 5 μg/each peptide) or the minimal epitope (ME) determined from T cell clones derived from each donor (D466:CFP10$_{2-11}$; D480:CFP10$_{3-11}$; D481: CFP10$_{75-83}$; 5 μg/ml), and tested against 250,000 magnetic bead purified CD8$^+$ T cells. IFN-γ release was assessed by ELISPOT after eighteen hours of co-culture. Each point represents the mean of duplicate determinations.
Figure 6:
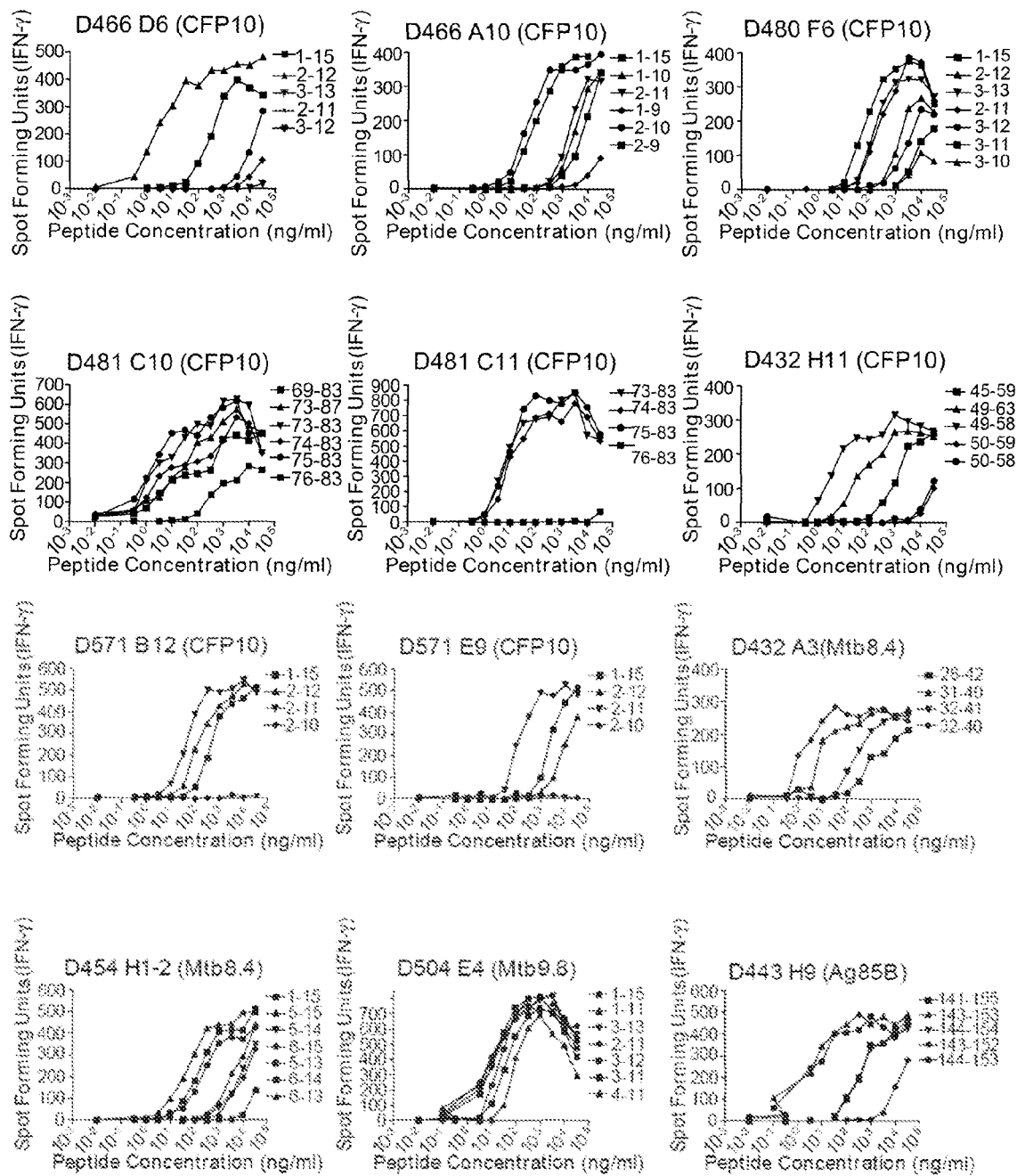
FIG. 6 is a set of graphs summarizing the minimal epitope mapping data. To determine the minimal epitope, autologous LCL (20,000/well) was pulsed with peptide at the concentration indicated and co-cultured with T-cells (1000 cells/well). IFN-γ was assessed by ELISPOT after eighteen hours co-culture. Each point represents the mean of duplicate determinations.
Figure 7:
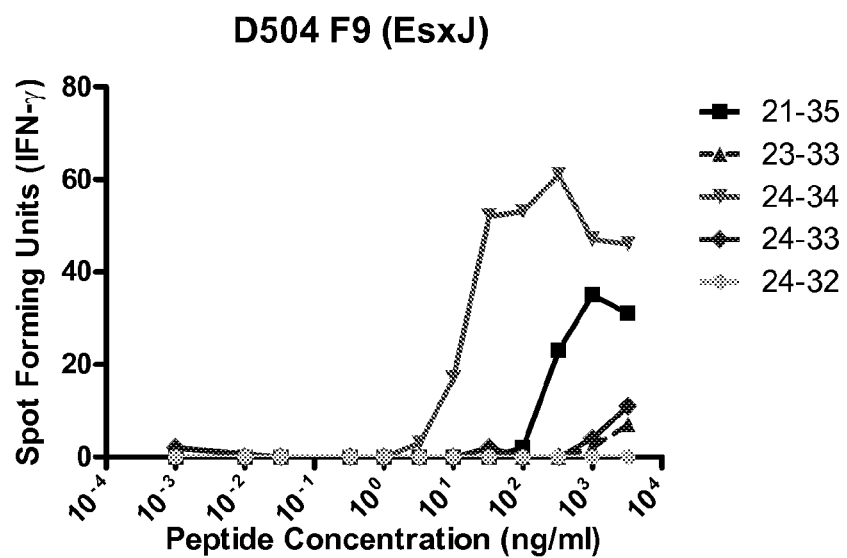
FIG. 7 is a line graph showing the mapping of Minimal Epitope for D504 Clones. To determine the minimal epitope, autologous LCL (20,000/well) was co-cultured with T-cell clones (1,000 cells/well) and the peptide at the concentration indicated. IFN-γ was assessed by ELISPOT after eighteen hours co-culture. Each point represents the mean of duplicate determinations.

This approach is demonstrated in detail for a single representative clone, D466 D6, derived from a subject with active TB. As shown in FIG. 3A, testing the clone against autologous DC pulsed with a panel of peptide pools unambiguously defined the antigenic specificity as CFP10. The clone was then tested against each of the 15-mer peptides that comprise the CFP10 pool, revealing that the epitope was contained within $CFP10_{1-15}$ (FIG. 3B). Each possible 8 aa, 9 aa, 10 aa, and 11 aa peptide was then synthesized and tested for reactivity, revealing antigenic activity between aa 2-11 (FIG. 3C). Similarly, each clone was tested against lymphoblastoid cell lines (LCL) sharing at least one HLA-type with the donor (FIG. 3D). Autologous LCL and IHW 9058 LCL, which share B4501 and C1601, present the epitope to the clone, identifying both B4501 and C1601 as possible restricting alleles. However, C1601+ D433 LCL do not present the epitope, eliminating C1601 as a candidate restricting allele. Therefore D466 D6 is restricted by HLA-B4501. As demonstrated in FIG. 4, by testing each plausible epitope over a broad range of concentrations, the minimal epitope was defined as CFP10$_{2\text{-}10}$ for D466 D6. Experimental data supporting the assignment of the minimal epitope is provided for each clone in the supplemental Figure. A summary of the antigenic specificity, minimal epitope, and HLA-restricting allele is presented in Table III. Unexpectedly, all but one of the T cell clones were restricted by HLA-B alleles. Furthermore, a minority of those observed were 9 aa in length.

tor cell frequency, as described in FIG. 1, each epitope was tested using autologous DC and magnetic bead purified CD8+ T cells derived from the donor from whom the T cell clones was isolated. A summary of the effector cell frequencies is presented in Table III. For the majority, the epitopes reflect high frequency responses, and thus could be considered a response that has been primed by exposure to Mtb. Notably, T cell clones isolated from four donors recognized CFP10. To determine if the epitopes defined reflected a substantial proportion of the total response to the antigen of interest, magnetic bead purified CD8+ T cells from three donors with sufficient available peripheral blood mononuclear cells (PBMC) were tested for reactivity to each individual 15-mer peptide, the peptide pool, and peptide representing the minimal epitope. As is demonstrated in FIG. 5, the ex vivo frequencies to the minimal epitope, 15-mer peptide(s) containing the minimal epitope, and peptide pool were remarkably concordant. These data suggested that for each donor a domi-

TABLE III

Summary of Epitopes Identified

| Clone[a] | Gene | Accession Number | HLA-Restrict Allele | Epitope Locat'n | Epitope Sequence (SEQ ID NOs: 26-38) | # SFU[b] | MHC Bind. Aff.[c] | V beta region |
|---|---|---|---|---|---|---|---|---|
| D160 1-1B[d] (0) | CFP10 | Rv3874 | B44 | 2-11 | AEMKTDAATL | 360 | 38 | |
| D160 1-6F[d] (0) | CFP10 | Rv3874 | B14 | 85-94 | RADEEQQQAL | 120 | NA | |
| D432 H12 (2) | CFP10 | Rv3874 | B3514 | 49-58 | TAAQAAVVRF | 258 | 2011[e] | 5.3 |
| D466 A10 (10) | CFP10 | Rv3874 | B4501 | 2-9 | AEMKTDAA | 2458 | 48 | IND |
| D466 D6 (1) | CFP10 | Rv3874 | B4501 | 2-12 | AEMKTDAATLA | 1993 | 6.2 | 22 |
| D481 C10 (10) | CFP10 | Rv3874 | B1502 | 75-83 | NIRQAGVQY | 1715 | 14[f] | 9 |
| D481 C11 (1) | CFP10 | Rv3874 | B1502 | 75-83 | NIRQAGVQY | 1715 | 14[f] | 13.6 |
| D480 F6 (6) | CFP10 | Rv3874 | B0801 | 3-11 | EMKTDAATL | 387 | 79 | 13.1 |
| D571 B12 (3) | CFP10 | Rv3874 | B4402 | 2-11 | AEMKTDAATL | 31 | 38 | IND |
| D571 E9 (4) | CFP10 | Rv3874 | B4402 | 2-11 | AEMKTDAATL | 31 | 38 | 14 |
| D504 E4 (1) | Mtb9.8 | Rv0287 | A0201 | 3-11 | LLDAHIPQL | <10 | 0.39 | 8 |
| D454 B10 (1) | Mtb9.8 | Rv0287 | B0801 | 53-61 | AAHARFVAA | 88 | 0.22 | IND |
| D454 H1-2 (1) | Mtb8.4 | Rv1174c | B1501 | 5-15 | AVINTTCNYGQ | 24 | 10 | 7.1 |
| D432 A3 (2) | Mtb 8.4 | Rv1174c | B3514 | 32-40 | ASPVAQSYL | 210 | 127[e] | 14 |
| D443 H9 (1) | Ag85B | Rv1886c | TBD | 144-153 | ELPQWLSANR | <10 | NA | 22 |

[a]Number of sister clones is in parentheses.
[b]# of SFU/250,000 CD8+ T cells is shown.
[c]IC50 in nm is shown.
[d]Published previously J Immunol. 2001 Jan 1; 166(1): 439-46.
[e]Measured binding affinity to B3501 is shown.
[f]Measured binding affinity to B1501 is shown.
NA = Not Available.
IND = Indeterminate
TBD = To be done.

Because each of the individual CD8+ T cell clones were derived based on growth of Mtb-infected DC, it was determined whether or not the antigen and epitopes identified reflected immunodominant epitopes ex vivo. Two independent approaches were pursued, the first to determine if the response was present at high frequency, and the second to determine what proportion of the total response to the antigen is constituted by the epitope. To determine the ex-vivo effecnance hierarchy has been clearly established, and is reflected in the original clones. Finally, as is noted in Table III, daughter clones of identical specificity were frequently identified, a result that would be predicted based on an immundominance hierarchy. TCR V beta staining was used to confirm the clonal relationship between daughter clones. Interestingly, in two cases, the identical minimal epitope and HLA-restriction was represented by two distinct clones (Table III).

Because much work on human CD8+ T cell responses to Mtb has relied upon the use of HLA-prediction algorithms, as each epitope was defined it was asked whether or not the epitopes would have been predicted by these approaches. Many of these epitopes were not ranked strongly. This might highlight the limitations of those algorithms at the time they were used. To address this question experimentally, the $IC_{50}$ for each peptide that had been synthesized in the course of definition of the minimal epitope was determined against a panel of human HLA molecules. Shown in Table III is the $IC_{50}$ for the minimal epitope with the cognate restricting allele. The data demonstrated that the T cell epitopes bound avidly to HLA, and show a high degree of concordance between the T cell epitope data and HLA-binding data.

The data demonstrated that CD8+ T cell responses are present in persons infected with Mtb at frequencies that are comparable to that seen following many common viral infections such as vaccinia, influenza, and CMV. All but one of the epitopes that were mapped were restricted by HLA-B molecules. The data suggest that by using a T cell driven approach to epitope identification, dominant epitopes can be defined in humans infected with Mtb.

Example 3

Screening of T Cell Clones Against a Genomic Peptide Library

The classically-restricted and non-classically-restricted T cell clones (see Table II above) that did not recognize one of the known Mtb antigen peptide pools (Rv3875, Rv3874, Rv1886c, Rv0287, Rv3763, Rv1174c, Rv1196, Rv1793, Rv2346c, Rv1037c, Rv3619c and Rv1198) were screened against a genomic peptide library. This peptide library represents 389 genes, representing roughly 10% of the Mtb genome. The peptides are 15 mers overlapping by 11 for each gene product. 50 nmol of each peptide was synthesized individually and then pooled into 777 pools of 50 peptides in a 96 well format (nine plates). Five blank wells and one well of an irrelevant peptide pool, SIV gag, were included on each of the nine plates. To screen the clones against the genomic peptide library, the clones are first expanded and tested against Mtb-infected DCs to ensure that each clone from this particular expansion yields a robust Mtb-specific signal in the ELISPOT assay. Then up to six T cell clones are pooled. For the screen, T cell clones (5,000 cells/well of each clone), autologous DCs (20,000 cells/well), IL-2 (0.5 ng/ml) and the peptide pools (5 ug/ml, individual peptides) were incubated overnight at 37 C in the ELISPOT assay. Only one technical replicate is done per pool because 5000 T cell clones per well with a peptide antigen produced an overwhelmingly positive response, resulting in a definitive result. Six classical clones from D504 were screened against the genomic peptide library, leading to the discovery of a new epitope. This epitope was from a family of four proteins that includes EsxJ, EsxW, EsxK and EsxP. These proteins share 98% homology and differ at only 3 amino acids. There is a fifth member of this family, EsxM (Rv1792), that was not included in the genomic peptide library.

The clones were screened against the individual fifteen-mers for these peptide pools. All six classical clones recognized EsxJ 21-35. This is a region of EsxJ that is identical to the other four members of this family. Next, 9, 10 and 11 mer peptides were made from this 15 mer and screened against each clone. The minimal epitope was determined to be EsxJ 24-34. In addition, the HLA restriction was found to be B5701.

Example 4

Additional Screening of T Cell Clones Against a Genomic Peptide Library

Eleven classical clones from D432B were screened against the genomic peptide library described above. The antigen was determined for two clones, which led to the identification of two novel epitopes, $PE\_PGRS42_{47-55}$ and $PE9_{53-67}$. The minimal epitope for one clone was determined to be $PE\_PGRS42_{47-55}$ and the HLA restriction was found to be B3514. The minimal epitope for the other clone is not yet determined, but is contained in the 15 mer $PE9_{53-67}$. The HLA restriction for this clone was found to be B3905.

TABLE IV

Detail of Novel Epitopes from Genomic Peptide Library Screens.

| Clone | Gene | Accession Number | Epitope Location | Epitope | #SFU/ 250,000 CD8+ T-cells | MHC- Restriction | MHC Binding Affinity (IC50 nm) | TCR V beta region |
|---|---|---|---|---|---|---|---|---|
| D504 F9 (6) | EsxJ* | Rv1038c | 24-34 SEQ ID NO: 2 | QTVEDE-ARRMW | 84 | B5701 | TBD | Indeterminate |
| D432 D8 (1) | PE9 | Rv1088 | 53-67 SEQ ID NO: 7 | RLFNAN-AEEYHA-LSA | TBD | B3905 | TBD | 8 |
| D432 H8 (1) | PE_PGRS42 | Rv2487c | 47-55 SEQ ID NO: 8 | VSAAIAG-LF | TBD | B3514 | TBD | 7.1 |

Number of clones recognizing epitope from each donor in parentheses./
*This is a family of proteins that have almost identical sequences. The family consists of Rv1038c, Rv1197, Rv2347, Rv3620c.

TABLE V

Summary of Completed Clone Screens.

| Donor | TB Status | # Classical available (screened) | # Non-Classical available (screened) | # positive wells in screen | # of confirmed hits | # novel epitopes | # classical clones epitope identified | # classical clones epitope NOT identified |
|---|---|---|---|---|---|---|---|---|
| 426 | PPD+ | 1 (1) | 4 (4) | 1 | 0 | 0 | 0 | 1 |
| 431 | Active | 1 (1) | 1 (1) | 1** | 0 | 0 | 0 | 1 |
| 432 | Active | 11 (11) | 14 (7) | 11 | 3 | 2 | 3 | 8 |
| 454 | PPD+ | 1* (0) | 6 (4) | 0 | 0 | 0 | 0 | 0 |
| 466 | Active | 1 (1) | 4 (4) | 1 | 0 | 0 | 0 | 1 |
| 504 | PPD+ | 6 (6) | 9 (9) | 5 | 4 | 1 | 6 | 0 |
| | | 21 (20) | 38 (29) | 18 | 7 | 3 | 9 | 11 |

*The classical clone from D454 did not recognize Mtb upon re-expansion and was not screened against library.
**The classical clones from 426 and 431 were screened together, so there was one positive well between both clones.

Example 5

Screening of Ex Vivo CD8+ T-Cells Against a Genomic Peptide Library

CD8+ T-cells from a LTBI donor, D610 (SE Asian) were screened against the genomic peptide library described above. Each plate of the genomic peptide library was screened in duplicate, for a total of 18 ELISPOT plates per screen. CD8+ T-cells were prepared from cryopreserved PBMC by CD8+ selection using magnetic bead separations. Resulting cell populations contained ≥96% CD8+ T cells. CD8+ T cells (250,000 cells/well), autologous DCs (20,000 cells/well), and IL-2 (0.5 ng/ml) were added to peptide (final 5 ug/ml, individual peptides) in the ELISPOT plates. Five media control wells are included on each plate. For each plate, the mean of these five wells was subtracted from each well of that plate to normalize between plates. Each technical replicate on each plate was then scored. A well was scored positive if the spot forming units (SFU), less the mean of the media wells, was greater than or equal to ten and the SFU was greater than or equal to twice the mean of the media. (Hudgens et al., *J. Immunol. Methods* 288: 19-34, 2004). This donor responded to the four peptide wells containing EsxJ, EsxW, EsxK and EsxP. CD8+ T-cells were then screened against each 15 mer from these peptide pools and found to respond only to EsxJ 21-35, the same region of EsxJ, EsxW, EsxK and EsxP that is described in example 3 above.

Seven additional donors were screened against the genomic peptide library. The top 10 responses are detailed in Table 7. The four peptide pools highlighted in yellow contain peptides from only one gene. These four genes contain four novel epitopes.

TABLE V

Top 10 Responses from Peptide Pool Screens of Seven Donors. Spot Forming Units are for 250,000 CD8+ T-cells.

| Peptide Pool | Donor | Average SFU | RvNumbers Represented in Wells | Functional Category |
|---|---|---|---|---|
| C09_1 | D560 | 208.2 | Rv1860(50): | cell wall and cell processes |
| C12_4 | D545 | 156.4 | Rv0468(27): Rv0456c(23): | lipid metabolism |
| A04_3 | D454 | 136 | Rv0284(17): Rv0288(11): Rv0287(22) | cell wall and cell processes |
| B10_3 | D560 | 112.3 | Rv1273c(50): | cell wall and cell processes |
| E04_4 | D560 | 78.2 | Rv0152c(40): Rv0151c(10): | PE/PPE |
| G12_8 | D560 | 77.4 | Rv3478(18): Rv3507(32): | PE/PPE |
| E07_4 | D525 | 76.8 | Rv0159c(50): | PE/PPE |
| A10_8 | D560 | 70.4 | Rv3136(47): Rv3144c(3): | PE/PPE |
| E11_8 | D560 | 66.4 | Rv3350c(50): | PE/PPE |
| E08_9 | D545 | 60.2 | Rv1404(13): Rv2711(37): | regulatory proteins |

Example 6

Use of CD8+ T Cell Test to Diagnose TB in Children

This result demonstrates the unexpected sensivity and specification of using CD8+ T cells to diagnose TB in children.

Methods

Participants and Procedures:

Participants were enrolled into two clinical study groups from separate recruitment sites in Kampala, Uganda. For the healthy exposed (HE) group, child household contacts (<15 years old) of adults were evaluated with AFB smear-positive, culture confirmed pulmonary TB enrolled in a prospective cohort study in Kampala, Uganda. Briefly, recruitment occurred after an adult family member sought care for TB. At study entry, detailed demographic and clinical information were collected on standardized forms, a standardized screening questionnaire for symptoms of active TB was administered, and a physical exam and anterior chest radiograph (CXR) were performed. All children had weight and height recorded at study enrollment. Nutritional status was determined by comparing individuals' body-mass-index (BMI) to WHO child growth standards, with severe malnutrition defined as a BMI Z-score of −3 or less. Tuberculin Skin Test (TST) was performed with the Mantoux method with 5 units of purified protein derivative (Pasteur Mérieux Connaught, Swiftwater, Pa.). The test was administered by a nurse or trained medical personnel and read within 48-72 hours of placement. A positive test was defined utilizing WHO criteria (WHO 2006), with induration greater than 5 mm considered positive for severely malnourished children and induration greater than 10 mm considered positive for the remainder of children. TST results were available for all study participants. HIV testing was performed for all children over 18 months by ELISA; children less than 18 months old had HIV testing performed only if a biological parent was found to be HIV positive. Children with symptoms concerning for active TB at enrollment or during the 6 to 24 month period of observation received a full clinical and diagnostic evaluation by a study physician, including a repeat CXR and mycobacterial smear and culture of at least one gastric aspirate sample. Specimens were processed by routine methods and underwent fluorochrome staining to detect AFB and were cultured on Loewenstein-Jensen media as well as in Middlebrook 7H9 broth. All mycobacterial cultures were monitored for growth of AFB for 8 weeks. Microbiologists were blinded to participants' TB classification and the results of TST testing. Only children that did not develop active TB after six months were included. Children with a history of prior or current TB or children who were immunosuppressed (receiving corticosteroids or with HIV) were excluded. Written informed consent was obtained.

For the Confirmed+Probable (CP) TB group, acutely ill children (≤10 years old) meeting WHO criteria for either confirmed or probable TB (table 1; WHO 1983) were enrolled. Children hospitalized with symptoms and signs of TB (suspect. TB, WHO 1983) were evaluated with full clinical assessment, CXR, TST, and HIV enzyme-linked immunoassay (ELISA) if older than 2 years or HIV Polymerase Chain Reaction (PCR) if less than 18 months. TST was performed and interpreted exactly as for the HE children. Based upon the results of this evaluation, children meeting criteria for probable TB were enrolled. Detailed demographic and clinical information was collected prospectively on standardized forms and surviving children were evaluated at a two month follow-up visit by a study physician. Exactly as for the HE children, children had weight and height recorded and nutritional status assessed. Enrolled children had mycobacterial smear and culture of one induced sputum sample. In some cases lymph node aspirates were obtained for pathology and/or mycobacterial smear and culture. Based upon two month follow-up, children received a final designation of confirmed TB, probable TB, or not TB. Children who did not have TB were excluded from the analysis. Investigators assigning TB classification were blinded to the results of ELISPOT testing. Written informed consent was obtained in the local language from each child's parent or guardian prior to study enrollment.

All children had 1-2 cc/kg (maximum 20 cc) of blood drawn at study enrollment, prior to placement of TST. Peripheral blood mononuclear cells (PBMCs) were isolated by standard methods and cryopreserved.

Media and Reagents:

Culture medium consisted of RPMI 1640 supplemented with 10% human sera, $5\times10^{-5}$ M 2 ME (Sigma-Aldrich), and 2 mM glutamine (GIBCO BRL). Peptides were synthesized by Genemed Synthesis. A single synthetic peptide pool consisting of 15 mers overlapping by 11 amino acids (aa) representing Mtb-specific proteins, CFP-10 and ESAT-6 were synthesized. Peptides were resuspended in DMSO, and 43 peptides were combined into one pool such that each peptide in the pool was at a concentration of 1 mg/ml. Peptide pools were stored at 8° C.

IFN-γ ELISPOT Assay:

An overnight IFN-γ ELISPOT assay was performed as described previously (2). Assays were performed on cryopreserved PBMC. PBMC preparation, cryopreservation, and IFN-γ ELISPOT assays were performed at the Joint Clinical Research Center (JCRC) immunology laboratory, Kampala, Uganda under the auspices of the TBRU. For determination of frequency of ESAT-6/CFP-10-specific $CD4^+$ T cells, whole PBMC were used as the source of responding T cells. For determination of frequency of ESAT-6/CFP-10-specific $CD8^+$ T cells, $CD8^+$ T cells, negatively selected from PBMCs using a combination of CD4 and CD56 magnetic beads (Miltenyi Biotec) were used as the source of responding T cells. While peptide-pulsed monocyte-derived dendritic cells (DC) have been found to be the most sensitive antigen presenting cell to enumerate $CD8^+$ T cell effectors ex vivo (3), it requires sufficient PBMC to generate DC. For these studies, the quantity of blood available precludes this approach. As a result, magnetic-bead depletion was used allowing the use of endogenous monocytes as the antigen presenting cell. In preliminary experiments, CD4 depletion resulted in a high background that could be eliminated through the simultaneous depletion of $CD56^+$ NK cells. When directly compared to using DC, this method is approximately 80% as efficient in enumerating antigen specific $CD8^+$ T cells. Flow cytometric analysis reveals a CD4 contamination rate of <2%, and CD8 purity of >85%. The remaining cells are comprised primarily of monocytes and B cells. IFN-γ ELISPOT was performed using 250,000 cells/well of PBMC ($CD4^+$ T cell assay) or CD4/CD56-depleted PBMC ($CD8^+$ T cell assay) and peptide pool as a source of antigen (final concentration of each peptide 5 μg/ml). Negative and positive controls were included in each assay and consisted of wells containing cells either without antigen or without antigen but with inclusion of phytohemagglutanin (PHA, 10 lg/ml; EMD Bioscience), respectively. All determinations were performed in duplicate. In some cases, the no antigen (media) control was performed in triplicate.

To determine the ex vivo frequency of antigen-specific T cells, the average number of spot forming units (SFU) per well for each duplicate was determined and compared to the average number of SFU in the media control. To account for well to well variability among technical replicates a standard deviation of the media control was calculated. A positive ELISPOT assay was defined as one in which the antigen-specific response was at least two standard deviations above the background control. If this criteria was met, the background was subtracted out to determine the antigen-specific response. A positive PHA response was defined as ≥30 SFU per well.

Study Design and Statistical Analysis:

A cross sectional study was performed comparing $CD4^+$ and $CD8^+$ T cell responses from baseline blood draws and compared two clinical study groups, children with CP-TB or HE children. In the first analysis, the HE study group was studied independently of the CP-TB group, to study the effect of age on the development of Mtb-specific T cell responses. For this analysis, all children ≤15 years were studied. Next, to compare the CP-TB with the HE study groups, only children from the HE group ≤10 years were selected to adjust for the inherent age differences in the cohorts as the CP-TB study group recruited to age ≤10.

ELISPOT assay data (SFU) was imported from Excel (Microsoft CORP, Redmond, Wash., USA) into a SAS data file and all analysis was performed using SAS version 9.1 (SAS Institute Inc, Cary, N.C., USA). Baseline univariate comparisons between HE and CP-TB and confirmed TB (C-TB) were performed using students t test for continuous and chi squared (or fishers exact where indicated) for categorical variables. Similarly, categorical comparisons of the frequency of positive ELISPOT assays by clinical study group were evaluated with a chi squared test. SFU above background were compared using nonparametric analysis for continuous variables (wilcoxon rank sum). Sensitivity was calculated as the number of positive assays over the total number of interpretable assays from the CP-TB group or the C-TB group alone. Specificity was calculated as the number Of negative assays over the total number of interpretable assays in the HE group.

To study the factors associated with CP-TB, several models were evaluated to study the impact of a positive ELISPOT assay on the association with clinical study group while adjusting for potential confounding covariates. In this regard, the odds of being in the CP-TB clinical study group versus the HE were modeled as explained by CD8 ELISPOT assay, CD4 ELISPOT assay, age (0-5, 5-10 years), nutritional status (BMI), and TST result. First the predictive value of the CD8 and CD4 ELISPOT alone was examined in the following models: (1) log odds (Clinical study group)=$\alpha+\beta_1$(+CD8 ELISPOT/–CD8 ELISPOT)+$\beta_2$(age)+$\beta_3$(ZBMI)+$\beta_4$(TST); (2) log odds (Clinical study group)=$\alpha+\beta_1$(+CD4 ELISPOT/–CD4 ELISPOT)+$\beta_2$(age)+$\beta_3$(ZBMI)+$\beta_4$(TST). In both models, the reference clinical study group was the HE group. The predictive value of the CD8 and CD4 ELISPOT assays was assessed in the same model. In this regard, the following model: log odds (Clinical study group)=$\alpha+\beta_1$(CD8 ELISPOT)+$\beta_2$(CD4 ELISPOT)+$\beta_3$(age)+$\beta_4$(ZBMI)+$\beta_5$(TST) was fit, where reference clinical study group is again the HE group. Backward logistic regression was then performed on all models to increase model fit.

Results

Figure 9:
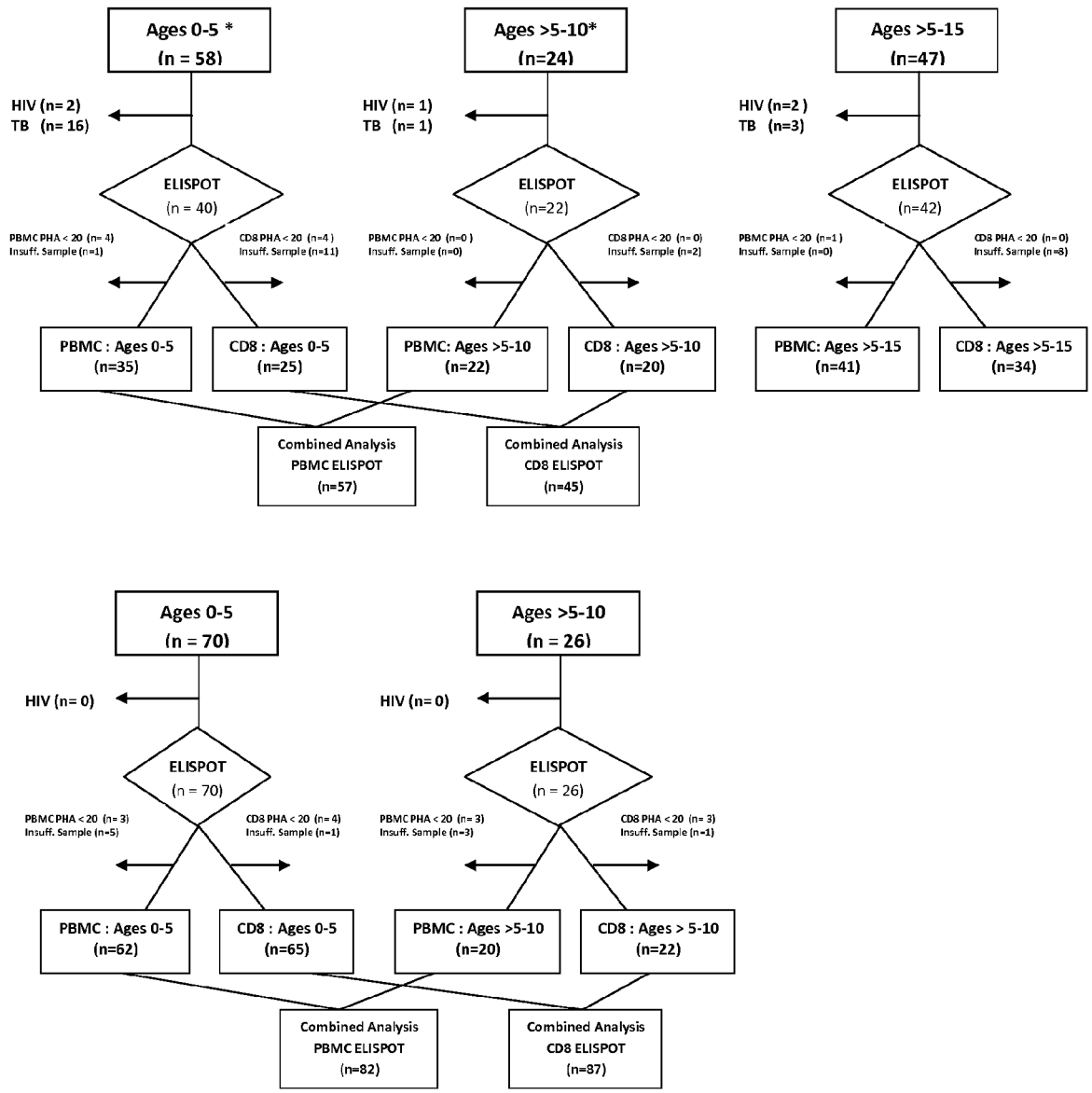
FIG. 9 is a flow diagram that depicts enrollment, subject exclusions, and ELISPOTs performed and analyzed. *refers to age groups included in the HE versus CP TB analysis.

To study the effect of age on CD4$^+$ and CD8$^+$ T cell responses in HE children, 129 child household contacts ≤15 years old (FIG. 9, top diagram) were evaluated. Exclusions included 20 children who developed TB within six months of baseline enrollment and 5 children who were found to be HIV positive. Thus, ELISPOT assays were performed on 104 household contacts ≤15 years old and 98 PBMC ELISPOT assays and 79 CD8 ELISPOT assays were included in the final analysis. To compare the CD4$^+$ and CD8$^+$ T cell responses between the HE cohort and the CP-TB cohort (≤10 years), the ELISPOT assay data was included only from HE children who were ≤10 years old. ELISPOT assays performed on 62 HE children were included in for this comparative analysis (FIG. 9, top diagram). Regarding the CP TB group, 101 HIV negative children with suspect TB (Table VI) were assessed for eligibility. Of these, 96 children with confirmed or probable TB were enrolled and CD4 and CD8 ELISPOTS were performed and 82 PBMC ELISPOTs and 87 CD8 ELISPOTS assays were interpretable and included in the final analysis, respectively (FIG. 9, bottom diagram). There was no significant difference between the number of interpretable samples among healthy TB exposed children, children with confirmed and probable TB, and children with confirmed TB.

TABLE VI

World Health Organization provisional guidelines for the diagnosis of pulmonary tuberculosis in children (WHO 1983)

a) Suspected tuberculosis

1-An ill child with a history of contact with a confirmed case of pulmonary tuberculosis
Any child 2-Not regaining normal health after measles or whooping cough
3-With loss of weight, cough and wheeze not responding to antibiotic therapy for respiratory disease
4-With painless swelling in a group of superficial nodes TABLE VI-continued World Health Organization provisional guidelines for the diagnosis of pulmonary tuberculosis in children (WHO 1983)

b) Probable tuberculosis

A suspect case and any of the following
Positive (>10 mm) induration on tuberculin testing
Suggestive appearance on chest radiograph
Suggestive histological appearance of biopsy material
Favorable response to specific antituberculous therapy
c) Confirmed tuberculosis Detection by microscopy or culture of tubercle bacilli from secretions or tissues
Identification of tubercle bacilli as *Mycobacterium tuberculosis* by culture characteristics Clinical characteristics and comparisons of all children enrolled in clinical study groups (HE (≤10 years old) and CP-TB) are shown in Table VII.

TABLE VII

Baseline characteristics of the HE and CP-TB study groups. Reported p values for continuous variables were calculated using students t test (ζ) Satterthwaite unequal variances. The p values for categorical data (TST and gender) were calculated using a chi squared method

|  | Healthy Exposed | CP-TB | p value |
| --- | --- | --- | --- |
| N | 62 | 96 |  |
| Female (%) | 29 (47) | 51 (52) | 0.4 ζ |
| Age |  |  |  |
| Mean/Median | 4.7, 4.5 | 3.6, 2.6 | 0.01 ζ |
| (IQR) | (2.5-6.0) | (1.0-6.0) |  |
| BMI |  |  |  |
| Mean/Median | 0.09, −0.12 | −0.82, −0.74 | <0.001 ζ |
| (IQR) | (−0.57 to 0.60) | (−2.1 to 0.61) |  |
| TST+ (%) | 28 (45) | 40 (42) | 0.6 ¶ |

Children with CP-TB were more malnourished (p<0.001) than the HE cohort and were slightly younger (0.01). The frequency of positive TST was equivalent in both HE and CP-TB children. Children with confirmed TB (C-TB) were more malnourished than HE children (p<0.001) and children with probable TB (P-TB, p=0.01) but did not differ in age, gender, or TST results from HE children or children with P-TB. Baseline clinical characteristics (age, gender, BMI, and TST status) of only children with interpretable ELISPOT results enrolled in the HE (≤10 years old) and CP-TB groups clinical study groups did not differ from those of all enrolled children.

Figure 10:
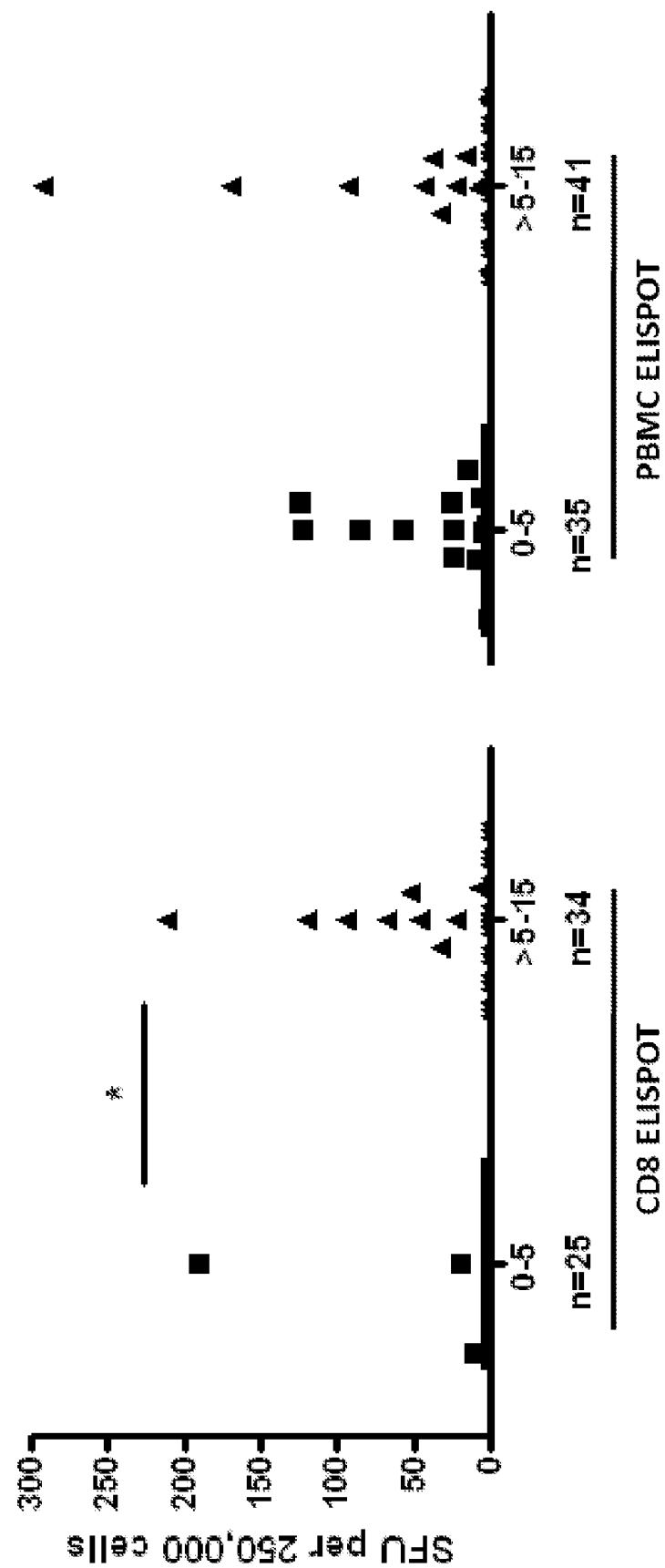
FIG. 10 is a graph showing a comparison of CD8 and CD4 ELISPOT responses across age strata for healthy exposed child contacts through age 15. Spot forming units above background are shown per 250,000 T cells. Initial enrollment numbers are shown in FIG. 9a. Cochran Armitage Test for Trend was performed: for the CD8 ELISPOT, p=0.055; for the PBMC ELISPOT, p=0.2.

First, to compare the acquisition of the Mtb-specific T cell response over time in children, the magnitude of Mtb-specific T cell responses were analyzed in the HE cohort, comparing children <5 years old to children 5≤15 years old. A robust CD4$^+$ T cell response was observed in both age groups, whereas CD8$^+$ T cell responses were decreased in children <5 years old compared to older children (p=0.055, FIG. 10). These data demonstrated that CD8$^+$ T cell responses are deficient in young children.

Figure 11A:
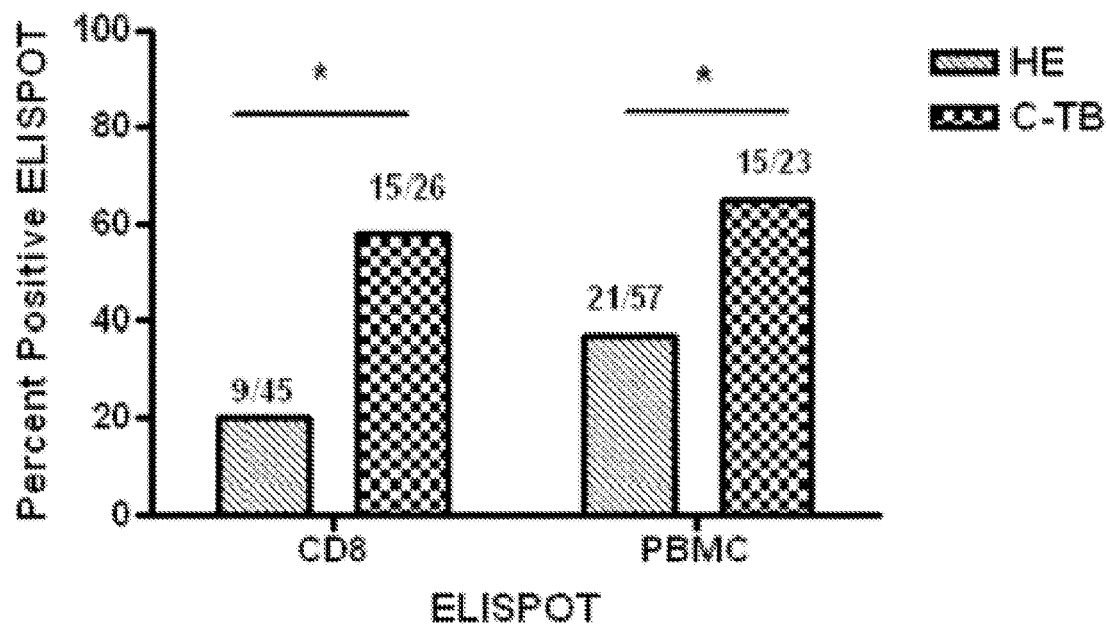
FIG. 11a is a graph showing the portion of positive ELISPOT assays in Ugandan children ≤10 stratified by clinical study group. CD8 and PBMC T cell responses are depicted for the HE and the confirmed TB (C-TB) subgroup. For the CD8 assay, children with C-TB were significantly more likely to have a positive assay (p=0.001) [20% of HE children (CI 0.09-0.34) compared with 58% of C-TB (CI 0.37-0.77)]. T his finding was also noted when comparing CP-TB with the HE. Similarly for the PBMC assay, the proportion of positive assays was greater in the C-TB clinical subgroup (p=0.02) [37% of HE children (CI 0.24-0.50) compared with 65% of C-TB (CI 0.42-0.83) had a positive assay]. Unlike for the CD8 assay, when CP-TB was compared with HE, the proportion positive did not significantly differ from the HE cohort.
Figure 11B:
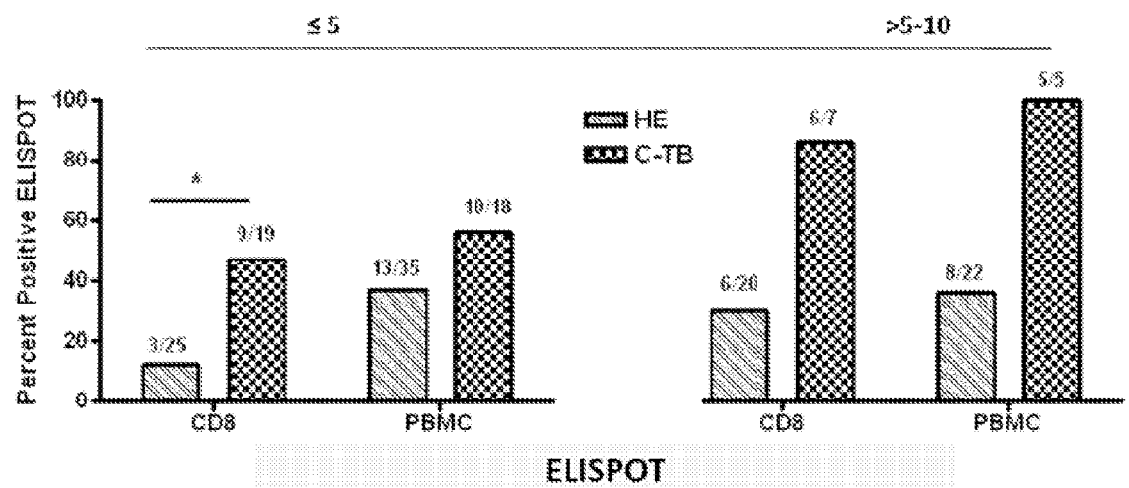
FIG. 11b is a graph of the proportion of positive ELISPOT assays in Ugandan children ≤10 stratified by clinical study group and by age. For the CD8 assay in children ≤5, children with confirmed TB were more likely to have a positive CD8 ELISPOT compared with the HE (p=0.009) [12% of the HE children (CI 0.03-0.31) compared with 47% of the C-TB (CI 0.24-0.71)]. Similarly, when CP-TB cohort was compared with the HE, CP-TB had a significantly larger proportion of positive CD8 assays. By comparison for the PBMC assay in children ≤5, a positive assay was not associated with a clinical study group [37% of the HE children (CI 0.21-0.55) whereas 56% of the C-TB (CI 0.30-0.78)] and this was true whether C-TB or CP-TB was used for comparison. For the children >5, the numbers were small thus comparative statistics was not performed. However both assays identified a high proportion of children with C-TP [for the CD8 assay in children >5, 30% of the HE (CI 0.11-0.54) compared with 86% of the C-TB (CI 0.42-0.99) had a positive assay]. By comparison for the CD4 assay in children ≥5, 36% of the HE (CI 0.17-0.59), whereas 100% of C-TB (CI 0.47-1.0) had a positive assay.

Next, Mtb-specific T cell responses were compared between HE children and children with TB. Compared to the HE cohort, the proportion of positive CD8 ELISPOT assays was greater in children with confirmed TB (C-TB cohort, p=0.001, FIG. 3a) and in all children with TB (CP-TB cohort, p=0.008). The proportion of positive CD4 (PBMC) ELISPOT assays was greater in the C-TB cohort than in HE cohort (p=0.02, FIG. 3a), but equivalent between the CP-TB and HE cohorts (p=0.14). HE, C-TB and CP-TB cohorts were then compared stratified by age. Similar to results of assays from all children, when comparing only HE children to children with TB less than 5 years old, the proportion of positive CD8 ELISPOT assays was greater in children with confirmed TB (C-TB cohort, p=0.009, FIG. 11b) and in all children with TB (CP-TB cohort). However, when considering only children <5 years old, the proportions of positive CD4 (PBMC) ELISPOT assays was equivalent between all cohorts (FIG. 11b). Among children 5≤10 years old, the proportion of positive CD8 and CD4 (PBMC) ELISPOT assays was greater in the CP-TB cohort compared to the HE cohort, but equivalent between the C-TB and HE cohorts.

Although evaluation of test performance of the CD4 and CD8 ELISPOT assays to identify TB were limited by small cohort size, an exploratory analysis of sensitivity and specificity of positive ELISPOT assays was performed, using C-TB as the gold standard TB cohort and HE cohort for calculations of sensitivity and specificity, respectively. In children ≤5 years old, the sensitivity of the CD4 and CD8 ELISPOT assays were equivalent, (56% of the C-TB (CI 0.30-0.78), and 47% of the C-TB (CI 0.24-0.71) respectively). However the CD8 ELISPOT assay was more specific than the CD4 ELISPOT assay (88% CI 0.68-0.97, and 62% CI 0.44-0.78, respectively).

In children 5>10 years old, the sensitivity and specificity of the CD4 and CD8 ELISPOT assays were similar (sensitivity, CD4 100% (CI 0.47-1.0)], CD8, 86% [(CI 0.0.42-0.99)]; specificity, CD4 63% [CI 0.40-0.82], CD8 70% [CI 0.45-0.88]). It was then asked which variables might impact and/or confound a positive or negative ELISPOT across the age strata. Logistic regression analysis was performed to model covariates associated with CP-TB and included CD8 and CD4 ELISPOT, age, nutritional status (Z score/BMI), and baseline TST status. For the first two models, the covariates for a positive CD8 and CD4 ELISPOT were modeled independently and then together in the third iteration Table VIII.

TABLE VIII

Multivariate logistic regression analysis of ELISPOT assay results*

| Covariate | β | SE β | $e^β$ ($OR_{ADJUSTED}$) | 95% CI | p value |
|---|---|---|---|---|---|
| Model 1: log odds(Clinical study group) = α + $β_1$(+CD8 ELISPOT/ −CD8 ELISPOT) + $β_2$(age) + $β_3$(ZBMI) +$β_4$(TST) | | | | | |
| CD8 ELISPOT | 1.3 | 0.44 | 3.8 | 1.5-9.7 | 0.004 |
| Age Group | 1.4 | 0.47 | 4.1 | 1.7-10.1 | 0.002 |
| ZBMI | −0.2 | 0.11 | 0.8 | 0.6-0.9 | 0.04 |
| TST status | −0.01 | 0.41 | 0.9 | 0.4-2.2 | 0.9 |
| Model 2: log odds (Clinical study group) = α + $β_1$(+CD4 ELISPOT/ −CD4 ELISPOT) + $β_2$(age) + $β_3$(ZBMI) + $β_4$(TST) | | | | | |
| CD4 ELISPOT | 0.58 | 0.37 | 1.8 | 0.8-3.7 | 0.12 |
| Age Group | 0.96 | 0.40 | 2.6 | 1.2-5.7 | 0.02 |
| ZBMI | −0.24 | 0.11 | 0.8 | 0.6-0.9 | 0.03 |
| TST status | 0.06 | 0.37 | 1.1 | 0.5-2.2 | 0.8 |
| Model 3: log odds (Clinical study group) = α + $β_1$(CD8 ELISPOT) + $β_2$(CD4 ELISPOT) + $β_3$(age) + $β_4$(ZBMI) + $β_5$(TST) | | | | | |
| CD8 ELISPOT | 1.5 | 0.55 | 4.7 | 1.6-13.8 | 0.005 |
| CD4 ELISPOT | −0.14 | 0.47 | 0.8 | 0.3-2.2 | 0.7 |
| Age Group | 1.5 | 0.47 | 4.6 | 1.8-11.7 | 0.001 |
| ZBMI | −0.18 | 0.11 | 0.8 | 0.6-1.1 | 0.1 |
| TST status | 0.05 | 0.47 | 1.1 | 0.4-2.4 | 0.8 |

*The log odds of having confirmed or probable TB was modeled according to various covariates shown in models 1-3. In model 1, the odds of having confirmed or probable TB was 3.8 times greater in children with a positive CD8 ELISPOT (Hosmer Lemeshow goodness of fit 0.07). In contrast, shown in model 2, the CD4 ELISPOT was not associated with having confirmed or probable TB (Hosmer Lemeshow goodness of fit p = 0.15). In model 3, where both covariates for CD8 and CD4 ELISPOT are included, the odds of having confirmed or probable TB was 4.7 times greater in children with a positive CD8 ELISPOT adjusted for other covariates in the model (Hosmer Lemeshow goodness of fit 0.21).

Children with a positive CD8 T cell ELISPOT had a 3.8 times greater odds of having CP-TB compared with that of children who are healthy and exposed (p=0.004) adjusted for age, BMI, and baseline TST. By comparison, children with a positive CD4 ELISPOT did not have greater odds of having CP-TB. In a model including both the CD8 and CD4 ELISPOT covariates, the presence of a positive CD8 ELISPOT was significantly associated with having CP-TB adjusted for the CD4 ELISPOT result. To increase model fit, backward logistic regression was employed. In this model, the odds of having confirmed or probable TB in someone with a positive CD8 ELISPOT was 4.6 times (CI 1.8-12.1) that of someone in the healthy exposed group adjusted for age only (p=0.002). The CD4 T cell ELISPOT did not add to the overall model fit and was eliminated in the backward iterative selection process along with BMI and the TST status (Hosmer Lemeshow goodness of fit p=0.68).

The magnitude of $CD8^+$ and $CD4^+$ T cell responses between the clinical study groups (FIG. 12). For children ≤5 years old, the magnitude of the $CD8^+$ T cell response was greater in children with TB (CP-TB, p=0.01; C-TB, p=0.009), while $CD4^+$ T cell (PBMC) responses were equivalent between clinical groups. Similarly, for children 5≤10 years old, the magnitude of $CD8^+$ and $CD4^+$ T cell responses were equivalent between the HE, CP-TB, and C-TB cohorts.

Example 6

Diagnosis of Extra-Pulmonary TB

Figure 8:
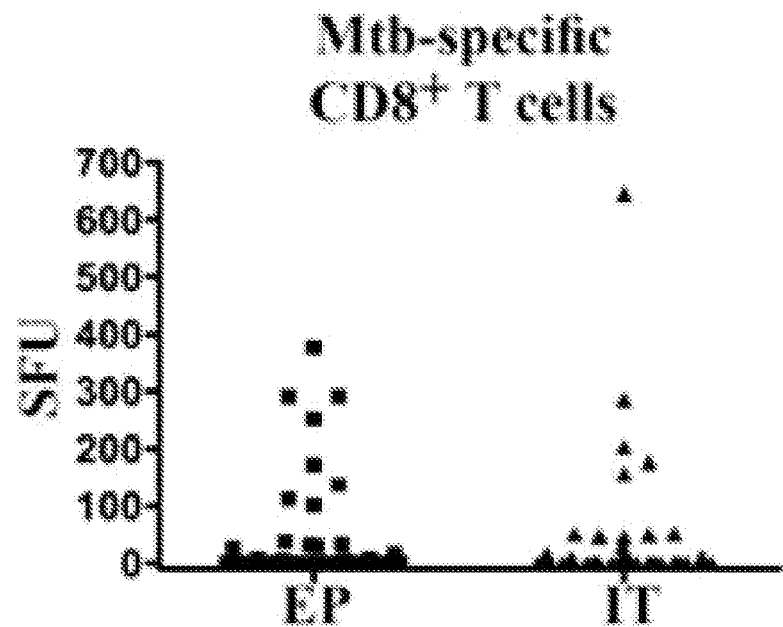
FIG. 8 is a graph showing Mtb-specific CD8+ T cell response in Ugandan children with extra-pulmonary (EP) TB as compared to intrathoracic (IT) TB. Mtb-specific CD8+ T cell response were measured using an interferon (IFN)-γ specific ELISPOT and ESAT-6 and CFP-10 peptides as a source of antigen, in Ugandan children of 10 years of age or less. The children had either EP (n=35) or IT TB (n=43). TB cohort was comprised mainly of scofula (30/35 [86%]). Results are shown in spot forming units (SFU) per 250,000 CD4/CD56 depleted peripheral blood mononuclear cells (PBMC). Determinations were performed in duplicate and positive responses were defined as those that were 2 standard deviations above the media control.

Diagnosis of extra-pulmonary TB is particularly challenging. The CD8+ T cell responses to ESAT-6 and CFP-10 were studied in Ugandan children with extra-pulmonary TB. In children with extra-pulmonary TB, 51% of CD8 ELISPOT assays were positive. Also, the magnitude of the $CD8^+$ T cell response in children with extra-pulmonary TB was comparable to that in children with intrathoracic TB (FIG. 8). Thus, a CD8 T cell based test can be used to diagnose for extra-pulmonary TB.

Example 7

Large Scale Confirmatory Clinical Trial

A. Study Participants

Hospitalized children <5 years of age are enrolled in the clinical trial. Older children and HIV infected children are excluded from study. The study design is to compare cohorts of children with (n=80 probable+confirmed TB; n=~20 confirmed TB) with children with lower respiratory tract infection that is not TB (LRTInotTB) (n=50). The initial assignment of intrathoracic TB will be made using WHO guidelines for provisional diagnosis of TB in children and children with probable intrathoracic TB will be enrolled. A summary of these guidelines are shown in Table 1. Specifically, results of clinical history, TST, and CXR are used to make a provisional diagnosis of probable TB. Additional inclusion criteria include TB therapy for less than one month. At two months following enrollment, clinical follow-up including response to anti-TB treatment and exclusion of alternate diagnoses, as well as Mtb culture results are used to make a final assignment of confirmed TB, probable TB, or not TB. Children who have confirmed or probable TB assigned at 2 month follow up will be retained in the total intrathoracic TB group. Children who do not have TB at two months will be excluded from the analysis. Because diagnosis can be confirmed by culture in <40% of TB cases, Mtb culture confirmation is not required for study inclusion. However, for data analysis, the subset of the intrathoracic TB cohort with confirmed TB (culture-confirmed intrathoracic TB) represents a primary comparison with the LRTInotTB cohort. The LRTInotTB cohort group is defined as children with LRTI defined by abnormal CXR and compatible symptoms and signs of pneumonia. In addition, this cohort must NOT have suspect TB as defined in the Table World Health Organization guidelines for the diagnosis of pulmonary tuberculosis in children Suspected tuberculosis:

1) An ill child with a history of contact with a confirmed case of pulmonary tuberculosis Any child:

2) Not regaining normal health after measles or whooping cough
3) With loss of weight, cough and wheeze not responding to antibiotic therapy for respiratory disease
4) With painless swelling in a group of superficial nodes Probable tuberculosis:
A suspect case and any of the following 1) Positive (>10 mm) induration on tuberculin testing
2) Suggestive appearance on chest radiograph
3) Suggestive histological appearance of biopsy material
4) Favorable response to specific antituberculous therapy Confirmed tuberculosis:

1) Detection by microscopy or culture of tubercle bacilli from secretions or tissues.
2) Identification of tubercle bacilli as *Mycobacterium tuberculosis* by culture characteristics The LRTInotTB cohort undergoes the same clinical and laboratory investigation as the intrathoracic TB cohort. Like the cohort, clinical follow-up at 2 months is used to make a final assignment of LRTInotTB. If the Mtb cultures are unexpectedly positive in any of these children, then these children are excluded from the analysis of LRTInotTB group.

For the proposed study, children are identified who are <5 years old who have symptoms and signs of LRTI. A history and physical are performed, and a CXR is obtained, and HIV screening results are reviewed. Children <18 months old with positive HIV ELISA results require an HIV PCR test to confirm infection. All children with negative HIV serology, and children <18 months old with positive HIV ELISA but negative HIV PCR can be included in the study. Children with positive HIV serology, including those children <18 months without available HIV PCR testing or with positive HIV PCR testing are excluded from study. HIV uninfected children <5 years who meet criteria for intrathoracic TB or LRTInotTB as defined above are enrolled. All subjects undergo TST placement and sputum induction for AFB smear and culture. TST is performed using purified protein derivative (PPD, 5 TU, Tubersol; Connaught Laboratories, Limited, Toronto, Canada) and the Mantoux method. Sputum induction for AFB smear and culture are performed. Subjects have blood drawn at the time of enrollment, and >25×10$^6$ PBMC are isolated to complete the study of all five antigen combinations. At two months, subjects are recalled for a follow-up study visit. At this visit the subject's interim history and laboratory results are reviewed. At this point, a final assignment to the study cohort (intrathoracic TB and LRTInotTB) is made.

B. Data Management for Demographic, Clinical, and Immunologic Data.

This studies uses the CWRU TBRU data management infrastructure or another similar data management program. For example, TELEform™ V5 Elite software (Cardiff Software, San Marcos Calif.) can be used which provides automated data entry from remote sites. Briefly, data collection forms are developed and formatted to interface with the TELEform™ software by data managers in Uganda. After a patient encounter, one copy of the data form is placed in the clinical chart and the other form is sent to the on-site data center where it is scanned into multi-page TIF (tagged image file format) image files. These files are compressed and stored. The TIF data files are then read into the TELEform™ program which aligns the form and records the data according to a predefined electronic template and then transfers the data into in a database management system. Once in the electronic database, the data are edited and cleaned using standard programs to flag missing data and out-of-range values. Formal queries were generated from the data center and on-site data managers resolve the query, amend the database, and record the changes. The electronic data is backed-up, for example on a daily basis.

Demographic and clinical characteristics relevant to this study include those pertaining to age, gender, disease description, HIV serostatus, BCG vaccination status, weight for age, and height for age, TST results, and Mtb culture results. In addition, for all enrolled children nutritional assessment is performed and, z scores for weight for age and height will be calculated. Finally, each subject is assigned a unique identifying number for use in the database.

C. Mtb Antigen CD8$^+$ T Cells Present in Children with Intrathoracic TB and LTBInotTB CD8$^+$ T cell responses are measured using an IFN-γ ELISPOT assay and CD4 and CD56 depleted PBMC as a source of antigen presenting cells (APC) and responding CD8$^+$ T cells. Specifically, CD8 ELISPOT assays are performed on cryopreserved PBMC. While peptide-pulsed DC are the most sensitive and specific means of eliciting CD8$^+$ T cell responses ex vivo, it requires sufficient PBMC to generate DC and highly purified CD8$^+$ T cells. For these studies, the quantity of blood available and the capacity to perform longer term cultures (DC) is limited. An alternative approach is to deplete CD4$^+$ T cells and use autologous monocytes as the APC. In preliminary experiments, CD4 depletion of PBMC resulted in high background that could be eliminated through the depletion of CD56$^+$ NK cells. When directly compared to using DC, this method is approximately 80% as efficient in enumerating antigen specific CD8$^+$ T cells. Consequently, to measure CD8$^+$ T cell responses, PBMC magnetic bead depleted of CD4 CD56 cells (250,000 cells/well) are used in an IFN-γ ELISPOT assay. Synthetic peptide pools (15-mers overlapping by 11 amino acids) representing the two antigen combinations are used as a source of antigen. The two-antigen combinations are represented by 43, 50, 72, 72, and 72 peptides for combinations CFP10/ESAT6, CFP10/EsxJ, CFP10/PPE51, CFP 10/CFPF, CFP10/PPE15. As a result, CD8$^+$ T cell responses to five CD8 antigen combinations are defined using as little as 10 million cryopreserved PBMC, requiring 1-5 ml of whole blood. Of note, smaller blood volumes are required for younger children, because infants' blood yield as many as 10 million PBMC per 1 ml of whole blood, while blood from older children and adults yields 1-2 million PBMC per 1 ml. An assay is considered positive if the SFU in experimental wells minus the control (media) wells is greater than 2 times the standard deviation of the control wells. The magnitude of the response is then expressed as SFU/250,000 cells. As a control for the efficacy of magnetic bead depletion, by cell surface staining for CD4 and analysis with flow cytometry, the percentage of contaminating $CD4^+$ T cells is determined. Any ELISPOT assay is considered to be invalid if the percentage of $CD4^+$ T cells exceeds 5%.

D. Are Mtb Antigen $CD4^+$ T Cells Present in Children with Intrathoracic TB and LTBInotTB? How does the Frequency of a Positive Assay and Magnitude of a Positive Response Compare Between Cohorts?

For comparison with $CD8^+$ T cell responses, a $CD4^+$ ELISPOT is performed using PBMC depleted of $CD8^+$ T cells as the source of responding $CD4^+$ T cells and remainder cells as APC as a measure of the Mtb antigen-specific $CD4^+$ T cell response. This is an assay very similar to the T-spot®.TB which uses PBMC, ESAT6/CFP10 peptides, and an IFN-γ ELISPOT assay. IFN-γ ELISPOT is performed using cryopreserved PBMC magnetic bead-depleted of CD8 cells (250,000 cells/well) as a source of both $CD4^+$ T cells and monocytes/APC. The same synthetic peptide pools used for the CD8 assays is used as a source of antigen. $CD4^+$ T cell response to five antigen combinations can be defined using as little as 3 million cryopreserved PBMC. An assay is considered positive if the SFU in experimental wells minus the control (media) wells is greater than 2 times the standard deviation of the control wells. The magnitude of the response is then expressed as SFU/250,000 cells. As a control for the efficacy of magnetic bead depletion, by cell surface staining for CD8 and analysis with flow cytometry, the percentage of contaminating $CD8^+$ T cells is determined. Any ELISPOT assay is considered to be invalid if the percentage of $CD8^+$ T cells exceeds 5%.

E. TST Results Positive in Children with Intrathoracic TB and LTBInotTB

For comparison with $CD8^+$ T cell responses, a TST is performed using standard methodologies as described above. Using WHO criteria, a positive TST is defined as induration ≥5 mm for severely malnourished children (Z score >−3) and induration ≥10 mm for the remainder of the children.

F. Statistical Considerations: sensitivity and specificity of two-antigen combinations and to select two combinations that will be used for the three-Mtb antigen combination study (SA 2).

The primary endpoints are $CD8^+$ T cell responses, $CD4^+$ T cell responses, and TST results. $CD8^+$ T cell responses and $CD4^+$ T cell responses are measured by IFN-γ producing T cells using the ELISPOT assays. The primary endpoint is a continuous response defined as the background adjusted ELISPOT counts. The background adjusted ELISPOT counts is defined according to the previously established criteria by our laboratory (CD8 antigen discovery program). TST results are analyzed only as a binary endpoint.

For the primary endpoint, the Receiver Operating Characteristic (ROC) curve method is applied and the area under the ROC curve (AUC) is estimated as a measure of diagnostic accuracy. For each antigen combination it is tested whether AUC is significantly greater than 50%, i.e., if there is an evidence of any diagnostic utility. The optimum-cut off point is determined for the background adjusted ELISPOT counts as to provide higher sensitivity while maintaining comparable specificity. The ROC analysis are performed for the following primary comparisons: culture-confirmed intrathoracic TB vs. LRTInotTB and total intrathoracic TB (probable+confirmed TB) vs. LRTInotTB. In addition, LRTInotTB with LTBI is defined as those subjects in the LRTInotTB cohort with a positive TST. Then the ROC analysis is performed for the following secondary comparisons: culture-confirmed intrathoracic TB vs. LRTInotTB with LTBI, and total intrathoracic TB (probable+confirmed TB) vs. LRTInotTB with LTBI). A logistic regression model is performed with the disease status as the outcome and the antigen response results as covariates (and any other potential confounders). The antigen responses can be evaluated both as binary and continuous covariates. The referent combination and add other combination are included one at a time to evaluate whether they have significantly improved the prediction. In addition, a stepwise procedure can be performed to select the optimal set of independent antigen combinations that predict the disease outcome. The results of these analyses are weighed against the primary criteria.

A sample size of 80 total intrathoracic TB (probable+confirmed TB) and 50 LRTInotTB allows detection of 15% improvement in AUC (50% to 65%) with 84% power and 5% significance level. The sample size of 20 culture-confirmed intrathoracic TB and 50 LRTInotTB allows detection of 20% improvement in AUC (50% to 70%) with 77% power and 5% significance level. The improvement of 15-20% is consistent with the preliminary data presented above.

Results:

The combination of antigens identified herein (ESAT6/CFP10), has similar results in the intrathoracic TB group with approximately 50% positive assays for $CD8^+$ T cells, $CD4^+$ T cells, and TST. $CD8^+$ T cells responses are not detected to these antigens in the LRTInotTB cohort. As the other four antigen combinations contain a second immunodominant CD8 antigen in addition to CFP10, an increased frequency of $CD8^+$ T cell assays is observed in the intrathoracic TB group to the other CFP10/Mtb antigen combinations compared to CFP10/ESAT-6. $CD8^+$ T cell responses are not detected to any of the antigen combinations tested in the LRTInotTB group. $CD4^+$ T cell assays to all antigen combinations, and TST's are positive in approximately 30% of this group. Similar or greater proportions of positive $CD8^+$ and $CD4^+$ T cell responses in culture-confirmed intrathoracic TB compared to the entire intrathoracic TB cohort.

Example 8

Animal Models

In tuberculosis research, the mouse model has been used extensively to model various aspects of the disease. Mice can be infected by a variety of routes, including intravenous, intraperitoneal and tracheal. One route is aerosolization of the organism for respiratory infection. The mice are exposed to the aerosol in a chamber (wither whole body or nose only infection). The dose of invention can be varied by manipulating the concentration of Mtb in the nebulizer or time of exposure. A low dose infection, such as about 50 colony forming units (CFU) via aerosol results in a slow and steady increase in bacterial numbers in the lungs, generally reaching a peak in four weeks, which coincides with the peak number off cells in the lungs. The initial period is considered the acute stage of infection. Following infection, there is a dissemination of bacteria to the mediastinal lymph nodes. T cell priming is generally detectable between two and three weeks. After about four weeks the bacterial numbers stabilize, and there is a slow progressive pathologic response. This system is of use for modeling active infection.

The ability of a composition of interest to prevent infection in an animal model can be evaluated using the methods described herein. The effectiveness of the composition of interst can be monitored by measuring the T cell response, such as the number of CD8+ or CD4+ T cells responding to an Mtb polypeptide in a biological sample. For these assays T cells with one are contacted with at least one *Mycobacterium* polypeptides, and an antigen presenting cell presenting the one or more *Mycobacterium* polypeptides. The *Mycobacterium* polypeptides include the amino acid sequence set forth as (a) one of the amino acid sequences set forth as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12; or (b) at least nine to twenty consecutive amino acids of at least one of the amino acid sequences set forth as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 7, SEQ ID NO: 8, SEQ ID NO: 9, SEQ ID NO: 10, SEQ ID NO: 11 or SEQ ID NO: 12, wherein the nine to twenty consecutive amino acids specifically bind major histocompatibility complex (MHC) class I. It is determined if the determining if the T cells specifically recognize the *Mycobacterium* polypeptide. An increase in the number of T cells that specifically recognize the Mtb polypeptide indicates that the composition is effective.

Exemplary animal models are described below (see also Repique et al., Infec. Immun. 70: 3318-3323, 2002, incorporated herein by reference for an additional protocol):

A. Short Term Mouse Model:

C57BL/6 mice are vaccinated with a composition according to the appropriate protocol and then rested for 4 to 6 weeks. Immunized mice are infected with a low dose aerosol 50-100 CFU) of virulent *M. tuberculosis* and protection is evaluated by assessing the number of viable bacilli 30 days post challenge.

Viable counts are performed on the lung and spleen of mice by homogenizing the organs and plating serial 10-fold dilutions on 7H11 agar plates. Plates are incubated for up to 21 days and the number of colony forming units per organ determined.

BCG vaccinated mice have approximately 1 Log 10 protection in their lung and spleen when compared to PBS-treated mice.

A biological sample is obtained prior to the administration of the composition of interest and after administration of the composition of interest. Alternatively, biological samples are obtained from vehicle treated animals and from animals treated with the composition of interst. An increase in the number of T cells that bind an Mtb polypeptide as disclosed herein indicates the composition is effective.

B. Short Term Guinea Pig Model

Out-bred Hartley guinea pigs are vaccinated with a composition including one or more Mtb polypeptide, or a polynucleotide encoding these one or more polypeptides and then rested for 8 to 10 weeks. Immunized guinea pigs are infected with a low dose aerosol (10-30 CFU) of virulent *M. tuberculosis* and protection is evaluated by assessing the number of viable bacilli 30 days post challenge.

Viable counts are performed on the lung and spleen of guinea pigs by homogenizing the organs and plating serial 10-fold dilutions on 7H11 agar plates. Plates are incubated for up to 21 days and the number of colony forming units per organ determined. Lung and spleen segments are also taken for histological analyses.

BCG vaccinated guinea pigs have approximately 2-3 $Log_{10}$ protection in their lung and spleen when compared to PBS-treated guinea pigs. In addition, BCG vaccinated guinea pigs have well defined granulomas when compared to unvaccinated animals.

A biological sample is obtained prior to the administration of the composition of interest and after administration of the composition of interest. Alternatively, biological samples are obtained from vehicle treated animals and from animals treated with the composition of interst. An increase in the number of T cells that bind an Mtb polypeptide as disclosed herein indicates the composition is effective.

C. Long Term Guinea Pig Model

The guinea pig model is similar to the mouse model, but the experiments are open-ended survival type and can last for as long as 2 years. Guinea pigs develop 'classical' granulomas similar to humans with active tuberculosis (TB), and as lung tissue necrosis progresses, they begin to lose weight and die of TB similar to humans. The number of colony forming units in the lungs and spleen can be assessed. Histological examination can also be performed to determine the degree of lung involvement and tissue destruction. After low-dose aerosol exposure in the guinea pig the number of organisms increases progressively during the first three weeks and then plateaus into a chronic state. During the later stages of infection there is increased bacterial load in the lung and this is associated with a worsening pathological condition. Without treatment, there is a concomitant rise in both CD4 and CD8 T cells in the lungs of infected guinea pigs.

Out-bred Hartley guinea pigs are vaccinated with the experimental vaccine according to the appropriate protocol and then rested for 8 to 10 weeks. Immunized guinea pigs are then infected with a low dose aerosol (10-30 CFU) of virulent *M. tuberculosis*. Guinea pigs are weighed weekly and monitored daily for signs of disease (such as increased respiration and failure to thrive). Unvaccinated guinea pigs succumb to infection from 20 to 25 weeks post challenge, while BCG vaccinated guinea pigs survive for 50 to 55 weeks post challenge.

At necropsy, the lung and spleen are assessed for the number of CFU and the extent of pathology. The relative protection of the experimental composition is compared to BCG vaccinated animals.

A biological sample is obtained prior to the administration of the composition of interest and after administration of the composition of interest. Alternatively, biological samples are obtained from vehicle treated animals and from animals treated with the composition of interst. An increase in the number of T cells that bind an Mtb polypeptide as disclosed herein indicates the composition is effective.

It will be apparent that the precise details of the methods or compositions described may be varied or modified without departing from the spirit of the described invention. We claim all such modifications and variations that fall within the scope and spirit of the claims below.

The invention claimed is:

1. A method for detecting *Mycobacterium tuberculosis* disease in a human child, comprising
isolating CD8+ T cells from a biological sample from a human child suspected of having tuberculosis disease;
contacting the CD8+ T cells with one or more *Mycobacterium* polypeptides; and
determining if the CD8+ T cells specifically recognize the one or more *Mycobacterium* polypeptides,
wherein the presence of CD8+ T cells that specifically recognize the one or more *Mycobacterium* polypeptides detects *Mycobacterium tuberculosis* in the child and identifies the child as having tuberculosis disease.

2. The method of claim 1, wherein the child is less than five years of age.

3. The method of claim 1, wherein the child is an infant.

4. The method of claim 1, wherein the child is suspected of having pulmonary tuberculosis disease.

5. The method of claim 1, wherein the child is suspected of having a disease caused by an extra-pulmonary infection with *Mycobacterium tuberculosis*.

6. The method of claim 5, wherein the disease caused by the extra-pulmonary infection comprises lymphadenitis, pleural tuberculosis, bone and joint tuberculosis, central nervous system tuberculosis, abdominal tuberculosis, miliary tuberculosis, or tuberculous pericarditis.

7. The method of claim 5, wherein the child is prepubescent.

8. The method of claim 1, wherein determining if the CD8+ T cells specifically recognize the one or more *Mycobacterium* polypeptides comprises measuring the expression of a cytokine.

9. The method of claim 8, wherein the cytokine is interferon-γ (IFN-γ).

10. The method of claim 9, wherein measuring expression of IFN-γ is determined using an antibody that specifically binds IFN-γ.

11. The method of claim 1, wherein the one or more *Mycobacterium* polypeptides comprises the amino acid sequence set forth as
(a) the amino acid sequence set forth as SEQ ID NO: 61; or
(b) at least nine to twenty consecutive amino acids of the amino acid sequence set forth as SEQ ID NO: 61, wherein the nine to twenty consecutive amino acids specifically bind major histocompatibility complex (MHC) class I.

12. The method of claim 11, wherein the one or more *Mycobacterium* polypeptides comprises the amino acid sequence set forth as SEQ ID NO: 61.

13. The method of claim 11, wherein the one or more *Mycobacterium* polypeptides consists of nine to twenty consecutive amino acids that specifically bind major histocompatibility complex (MHC) class I of the amino acid sequence set forth as SEQ ID NO: 61.

14. The method of claim 1, wherein the biological sample is blood, isolated peripheral blood mononuclear cells, isolated mononuclear cells, sputum, a lung biopsy, a lymph node biopsy, saliva, cerebral spinal fluid or isolated CD3+T cells.

15. The method of claim 1, wherein the CD8+ T cells are cultured in vitro with the *Mycobacterium* polypeptide.

16. The method of claim 1, further comprising detecting a delayed type hypersensitivity reaction to *Mycobacterium tuberculosis*.

17. The method of claim 1, further comprising detecting the presence of a *Mycobacterium* polypeptide or a polynucleotide encoding a *Mycobacterium* polypeptide in a sample from the subject, wherein the *Mycobacterium* polypeptide comprises the amino acid sequence set forth as SEQ ID NO: 61.

18. The method of claim 17, comprising detecting the presence of the *Mycobacterium* polypeptide.

19. The method of claim 18, wherein detecting the presence of the *Mycobacterium* polypeptide comprises using an antibody that specifically binds the amino acid sequence set forth as SEQ ID NO: 61.

20. The method of claim 17, comprising detecting the presence of the *Mycobacterium* polynucleotide.

21. The method of claim 20, wherein detecting the presence of the polynucleotide comprises using a polymerase chain reaction.

22. A method of detecting T cells expressing CD8 that specifically bind a *Mycobacterium* polypeptide in a subject, wherein the subject is a child, the method comprising
   (A) contacting peripheral blood mononuclear cells isolated from the subject with a reagent comprising
      (1) a *Mycobacterium* polypeptide comprising at least nine to twenty consecutive amino acids of the amino acid sequence set forth as SEQ ID NO: 61, wherein the nine to twenty consecutive amino acids specifically bind major histocompatibility complex (MHC) class I;
      (2) HLA heavy chain polypeptide and B2-microglobulin; and
      (3) streptavidin, wherein the reagent is labeled or unlabeled; and
   (B) detecting the presence of the reagent bound to the peripheral blood mononuclear cells, thereby detecting T cells expressing CD8 that specifically bind the *Mycobacterium* polypeptide.

23. The method of claim 11, wherein the one or more *Mycobacterium* polypeptides comprises the amino acid sequence set forth as one of SEQ ID NOs: 62-83.

24. The method of claim 22, wherein the *Mycobacterium* polypeptide comprises the amino acid sequence set forth as SEQ ID NO: 61.

25. The method of claim 24, wherein the *Mycobacterium* polypeptide consists of one of the amino acid sequences set forth as SEQ ID NOs: 62-83.

26. The method of claim 1, wherein said isolating comprises depleting CD4+ T cells from the biological sample.

* * * * *

SEQUENCE LISTING

<160> NUMBER OF SEQ ID NOS: 86

<210> SEQ ID NO 1
<211> LENGTH: 97
<212> TYPE: PRT
<213> ORGANISM: Mycobacterium tuberculosis
<220> FEATURE:
<221> NAME/KEY: X
<222> LOCATION: (2)..(58)
<223> OTHER INFORMATION: X is A or T
<220> FEATURE:
<221> NAME/KEY: X
<222> LOCATION: (59)..(59)
<223> OTHER INFORMATION: X is any amino acid

<400> SEQUENCE: 1

Met Xaa Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Xaa Xaa Met Asn Gln Ala Phe
    50                  55                  60

Arg Asn Ile Val Asn Met Leu His Gly Val Arg Asp Gly Leu Val Arg
65                  70                  75                  80

Asp Ala Asn Asn Tyr Glu Gln Gln Glu Gln Ala Ser Gln Gln Ile Leu
                85                  90                  95

Ser

<210> SEQ ID NO 2
<211> LENGTH: 97
<212> TYPE: PRT
<213> ORGANISM: Mycobacterium tuberculosis

<400> SEQUENCE: 2

Met Ala Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Thr Gln Met Asn Gln Ala Phe
    50                  55                  60

Arg Asn Ile Val Asn Met Leu His Gly Val Arg Asp Gly Leu Val Arg
65                  70                  75                  80

Asp Ala Asn Asn Tyr Glu Gln Gln Glu Gln Ala Ser Gln Gln Ile Leu
                85                  90                  95

Ser

<210> SEQ ID NO 3
<211> LENGTH: 98
<212> TYPE: PRT
<213> ORGANISM: Mycobacterium tuberculosis

<400> SEQUENCE: 3

Met Ala Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg

```
                    20                  25                  30
Met Trp Ala Ser Ala Gln Asn Ile Ser Gly Ala Gly Trp Ser Gly Met
            35                  40                  45
Ala Glu Ala Thr Ser Leu Asp Thr Met Ala Gln Met Asn Gln Ala Phe
        50                  55                  60
Arg Asn Ile Val Asn Met Leu His Gly Val Arg Asp Gly Leu Val Arg
65                  70                  75                  80
Asp Ala Asn Asn Tyr Glu Gln Gln Glu Gln Ala Ser Gln Gln Ile Leu
                85                  90                  95
Ser Ser

<210> SEQ ID NO 4
<211> LENGTH: 97
<212> TYPE: PRT
<213> ORGANISM: Mycobacterium tuberculosis

<400> SEQUENCE: 4

Met Ala Ser Arg Phe Met Thr Asp Pro His Ala Met Arg Asp Met Ala
1               5                   10                  15
Gly Arg Phe Glu Val His Ala Gln Thr Val Glu Asp Glu Ala Arg Arg
                20                  25                  30
Met Trp Ala Ser Ala Gln Asn Ile Ser Gly Ala Gly Trp Ser Gly Met
            35                  40                  45
Ala Glu Ala Thr Ser Leu Asp Thr Met Thr Met Asn Gln Ala Phe Arg
        50                  55                  60
Asn Ile Val Asn Met Leu His Gly Val Arg Asp Gly Leu Val Arg Asp
65                  70                  75                  80
Ala Asn Asn Tyr Glu Gln Gln Glu Gln Ala Ser Gln Gln Ile Leu Ser
                85                  90                  95
Ser

<210> SEQ ID NO 5
<211> LENGTH: 98
<212> TYPE: PRT
<213> ORGANISM: Mycobacterium tuberculosis

<400> SEQUENCE: 5

Met Ala Thr Arg Phe Met Thr Asp Pro His Ala Met Arg Asp Met Ala
1               5                   10                  15
Gly Arg Phe Glu Val His Ala Gln Thr Val Glu Asp Glu Ala Arg Arg
                20                  25                  30
Met Trp Ala Ser Ala Gln Asn Ile Ser Gly Ala Gly Trp Ser Gly Met
            35                  40                  45
Ala Glu Ala Thr Ser Leu Asp Thr Met Ala Gln Met Asn Gln Ala Phe
        50                  55                  60
Arg Asn Ile Val Asn Met Leu His Gly Val Arg Asp Gly Leu Val Arg
65                  70                  75                  80
Asp Ala Asn Asn Tyr Glu Gln Gln Glu Gln Ala Ser Gln Gln Ile Leu
                85                  90                  95
Ser Ser

<210> SEQ ID NO 6
<211> LENGTH: 98
<212> TYPE: PRT
<213> ORGANISM: Mycobacterium tuberculosis

<400> SEQUENCE: 6
```

Met Thr Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Thr Gln Met Asn Gln Ala Phe
    50                  55                  60

Arg Asn Ile Val Asn Met Leu His Gly Val Arg Asp Gly Leu Val Arg
65                  70                  75                  80

Asp Ala Asn Asn Tyr Glu Gln Gln Glu Gln Ala Ser Gln Ile Leu
                85                  90                  95

Ser Ser

<210> SEQ ID NO 7
<211> LENGTH: 144
<212> TYPE: PRT
<213> ORGANISM: Mycobacterium tuberculosis

<400> SEQUENCE: 7

Met Ser Tyr Met Ile Ala Thr Pro Ala Ala Leu Thr Ala Ala Ala Thr
1               5                   10                  15

Asp Ile Asp Gly Ile Gly Ser Ala Val Ser Val Ala Asn Ala Ala
            20                  25                  30

Val Ala Ala Thr Thr Gly Val Leu Ala Ala Gly Gly Asp Glu Val Leu
        35                  40                  45

Ala Ala Ile Ala Arg Leu Phe Asn Ala Asn Ala Glu Glu Tyr His Ala
    50                  55                  60

Leu Ser Ala Gln Val Ala Ala Phe Gln Thr Leu Phe Val Arg Thr Leu
65                  70                  75                  80

Thr Gly Gly Cys Gly Val Phe Arg Arg Arg Gly Arg Gln Cys Val
            85                  90                  95

Thr Ala Ala Glu His Arg Ala Ala Gly Ala Gly Arg Arg Gln Arg Arg
        100                 105                 110

Arg Arg Ser Gly Asp Gly Gln Trp Arg Leu Arg Gln Arg His Phe
    115                 120                 125

Gly Cys Gly Gly Gln Pro Glu Phe Arg Gln His Ser Glu His Arg Arg
    130                 135                 140

<210> SEQ ID NO 8
<211> LENGTH: 694
<212> TYPE: PRT
<213> ORGANISM: Mycobacterium tuberculosis

<400> SEQUENCE: 8

Val Ser Leu Val Ile Ala Thr Pro Gln Leu Leu Ala Thr Ala Ala Leu
1               5                   10                  15

Asp Leu Ala Ser Ile Gly Ser Gln Val Ser Ala Ala Asn Ala Ala Ala
            20                  25                  30

Ala Met Pro Thr Thr Glu Val Val Ala Ala Ala Asp Glu Val Ser
        35                  40                  45

Ala Ala Ile Ala Gly Leu Phe Gly Ala His Ala Arg Gln Tyr Gln Ala
    50                  55                  60

Leu Ser Val Gln Val Ala Ala Phe His Glu Gln Phe Val Gln Ala Leu
65                  70                  75                  80

Thr Ala Ala Ala Gly Arg Tyr Ala Ser Thr Glu Ala Ala Val Glu Arg
                85                  90                  95

```
Ser Leu Leu Gly Ala Val Asn Ala Pro Thr Glu Ala Leu Leu Gly Arg
                100                 105                 110

Pro Leu Ile Gly Asn Gly Ala Asp Gly Thr Ala Pro Gly Gln Pro Gly
            115                 120                 125

Ala Ala Gly Gly Leu Leu Phe Gly Asn Gly Gly Asn Gly Ala Ala Gly
        130                 135                 140

Gly Phe Gly Gln Thr Gly Gly Ser Gly Gly Ala Ala Gly Leu Ile Gly
145                 150                 155                 160

Asn Gly Gly Asn Gly Gly Ala Gly Gly Thr Gly Ala Ala Gly Gly Ala
                165                 170                 175

Gly Gly Asn Gly Gly Trp Leu Trp Gly Asn Gly Asn Gly Gly Val
                180                 185                 190

Gly Gly Thr Ser Val Ala Ala Gly Ile Gly Gly Ala Gly Gly Asn Gly
                195                 200                 205

Gly Asn Ala Gly Leu Phe Gly His Gly Gly Ala Gly Gly Thr Gly Gly
            210                 215                 220

Ala Gly Leu Ala Gly Ala Asn Gly Val Asn Pro Thr Pro Gly Pro Ala
225                 230                 235                 240

Ala Ser Thr Gly Asp Ser Pro Ala Asp Val Ser Gly Ile Gly Asp Gln
                245                 250                 255

Thr Gly Gly Asp Gly Gly Thr Gly Gly His Gly Thr Ala Gly Thr Pro
                260                 265                 270

Thr Gly Gly Thr Gly Gly Asp Gly Ala Thr Ala Thr Ala Gly Ser Gly
                275                 280                 285

Lys Ala Thr Gly Gly Ala Gly Gly Asp Gly Gly Thr Ala Ala Ala Gly
                290                 295                 300

Gly Gly Gly Gly Asn Gly Gly Asp Gly Gly Val Ala Gln Gly Asp Ile
305                 310                 315                 320

Ala Ser Ala Phe Gly Gly Asp Gly Gly Asn Gly Ser Asp Gly Val Ala
                325                 330                 335

Ala Gly Ser Gly Gly Gly Ser Gly Gly Ala Gly Gly Ala Phe Val
                340                 345                 350

His Ile Ala Thr Ala Thr Ser Thr Gly Gly Ser Gly Gly Phe Gly Gly
                355                 360                 365

Asn Gly Ala Ala Ser Ala Ala Ser Gly Ala Asp Gly Gly Ala Gly Gly
                370                 375                 380

Ala Gly Gly Asn Gly Gly Ala Gly Gly Leu Leu Phe Gly Asp Gly Gly
385                 390                 395                 400

Asn Gly Gly Ala Gly Gly Ala Gly Ile Gly Gly Asp Gly Ala Thr
                405                 410                 415

Gly Gly Pro Gly Gly Ser Gly Gly Asn Ala Gly Ile Ala Arg Phe Asp
                420                 425                 430

Ser Pro Asp Pro Glu Ala Glu Pro Asp Val Val Gly Lys Gly Gly
                435                 440                 445

Asp Gly Gly Lys Gly Gly Ser Gly Leu Gly Val Gly Gly Ala Gly Gly
            450                 455                 460

Thr Gly Gly Ala Gly Gly Asn Gly Gly Ala Gly Gly Leu Leu Phe Gly
465                 470                 475                 480

Asn Gly Gly Asn Gly Gly Asn Ala Gly Ala Gly Gly Asp Gly Gly Ala
                485                 490                 495

Gly Val Ala Gly Gly Val Gly Gly Asn Gly Gly Gly Gly Thr Ala
                500                 505                 510

Thr Phe His Glu Asp Pro Val Ala Gly Val Trp Ala Val Gly Gly Val
```

```
                515                 520                 525
Gly Gly Asp Gly Gly Ser Gly Ser Ser Leu Gly Val Gly Gly Val
        530                 535                 540
Gly Gly Ala Gly Gly Val Gly Gly Lys Gly Gly Ala Ser Gly Met Leu
545                 550                 555                 560
Ile Gly Asn Gly Gly Asn Gly Ser Gly Gly Val Gly Gly Ala Gly
                565                 570                 575
Gly Val Gly Gly Ala Gly Gly Asp Gly Gly Asn Gly Ser Gly Gly
                580                 585                 590
Asn Ala Ser Thr Phe Gly Asp Glu Asn Ser Ile Gly Gly Ala Gly Gly
                595                 600                 605
Thr Gly Gly Asn Gly Gly Asn Gly Ala Asn Gly Gly Asn Gly Gly Ala
                610                 615                 620
Gly Gly Ile Ala Gly Gly Ala Gly Gly Ser Gly Gly Phe Leu Ser Gly
625                 630                 635                 640
Ala Ala Gly Val Ser Gly Ala Asp Gly Ile Gly Gly Ala Gly Gly Ala
                645                 650                 655
Gly Gly Ala Gly Gly Ala Gly Gly Ser Gly Gly Glu Ala Gly Ala Gly
                660                 665                 670
Gly Leu Thr Asn Gly Pro Gly Ser Pro Gly Val Ser Gly Thr Glu Gly
                675                 680                 685
Met Ala Gly Ala Pro Gly
        690

<210> SEQ ID NO 9
<211> LENGTH: 325
<212> TYPE: PRT
<213> ORGANISM: Mycobacterium tuberculosis

<400> SEQUENCE: 9

Met His Gln Val Asp Pro Asn Leu Thr Arg Arg Lys Gly Arg Leu Ala
1               5                   10                  15
Ala Leu Ala Ile Ala Ala Met Ala Ser Ala Ser Leu Val Thr Val Ala
                20                  25                  30
Val Pro Ala Thr Ala Asn Ala Asp Pro Glu Pro Ala Pro Pro Val Pro
            35                  40                  45
Thr Thr Ala Ala Ser Pro Pro Ser Thr Ala Ala Ala Pro Pro Ala Pro
        50                  55                  60
Ala Thr Pro Val Ala Pro Pro Pro Ala Ala Ala Asn Thr Pro Asn
65                  70                  75                  80
Ala Gln Pro Gly Asp Pro Asn Ala Ala Pro Pro Pro Ala Asp Pro Asn
                85                  90                  95
Ala Pro Pro Pro Pro Val Ile Ala Pro Asn Ala Pro Gln Pro Val Arg
                100                 105                 110
Ile Asp Asn Pro Val Gly Gly Phe Ser Phe Ala Leu Pro Ala Gly Trp
                115                 120                 125
Val Glu Ser Asp Ala Ala His Phe Asp Tyr Gly Ser Ala Leu Leu Ser
            130                 135                 140
Lys Thr Thr Gly Asp Pro Pro Phe Pro Gly Gln Pro Pro Pro Val Ala
145                 150                 155                 160
Asn Asp Thr Arg Ile Val Leu Gly Arg Leu Asp Gln Lys Leu Tyr Ala
                165                 170                 175
Ser Ala Glu Ala Thr Asp Ser Lys Ala Ala Ala Arg Leu Gly Ser Asp
                180                 185                 190
Met Gly Glu Phe Tyr Met Pro Tyr Pro Gly Thr Arg Ile Asn Gln Glu
```

```
                195                 200                 205
Thr Val Ser Leu Asp Ala Asn Gly Val Ser Gly Ser Ala Ser Tyr Tyr
    210                 215                 220

Glu Val Lys Phe Ser Asp Pro Ser Lys Pro Asn Gly Gln Ile Trp Thr
225                 230                 235                 240

Gly Val Ile Gly Ser Pro Ala Ala Asn Ala Pro Asp Ala Gly Pro Pro
                245                 250                 255

Gln Arg Trp Phe Val Val Trp Leu Gly Thr Ala Asn Asn Pro Val Asp
                260                 265                 270

Lys Gly Ala Ala Lys Ala Leu Ala Glu Ser Ile Arg Pro Leu Val Ala
                275                 280                 285

Pro Pro Pro Ala Pro Ala Pro Ala Pro Ala Glu Pro Ala Pro Ala Pro
                290                 295                 300

Ala Pro Ala Gly Glu Val Ala Pro Thr Pro Thr Thr Pro Thr Pro Gln
305                 310                 315                 320

Arg Thr Leu Pro Ala
                325

<210> SEQ ID NO 10
<211> LENGTH: 582
<212> TYPE: PRT
<213> ORGANISM: Mycobacterium tuberculosis

<400> SEQUENCE: 10

Met Leu Leu Ala Leu Leu Arg Gln His Ile Arg Pro Tyr Arg Arg Leu
1               5                   10                  15

Val Ala Met Leu Met Met Leu Gln Leu Val Ser Thr Leu Ala Ser Leu
                20                  25                  30

Tyr Leu Pro Thr Val Asn Ala Ala Ile Val Asp Asp Gly Val Ala Lys
            35                  40                  45

Gly Asp Thr Ala Thr Ile Val Arg Leu Gly Ala Val Met Leu Gly Val
    50                  55                  60

Thr Gly Leu Gln Val Leu Cys Ala Ile Gly Ala Val Tyr Leu Gly Ser
65                  70                  75                  80

Arg Thr Gly Ala Gly Phe Gly Arg Asp Leu Arg Ser Ala Met Phe Glu
                85                  90                  95

His Ile Ile Thr Phe Ser Glu Arg Glu Thr Ala Arg Phe Gly Ala Pro
            100                 105                 110

Thr Leu Leu Thr Arg Ser Thr Asn Asp Val Arg Gln Ile Leu Phe Leu
        115                 120                 125

Val Gln Met Thr Ala Thr Val Leu Val Thr Ala Pro Ile Met Cys Val
    130                 135                 140

Gly Gly Ile Ile Met Ala Ile His Gln Glu Ala Ala Leu Thr Trp Leu
145                 150                 155                 160

Leu Leu Val Ser Val Pro Ile Leu Ala Val Ala Asn Tyr Trp Ile Ile
                165                 170                 175

Ser His Met Leu Pro Leu Phe Arg Arg Met Gln Ser Leu Ile Asp Gly
            180                 185                 190

Ile Asn Arg Val Met Arg Asp Gln Leu Ser Gly Val Arg Val Val Arg
        195                 200                 205

Ala Phe Thr Arg Glu Gly Tyr Glu Arg Asp Lys Phe Ala Gln Ala Asn
    210                 215                 220

Thr Ala Leu Ser Asn Ala Ala Leu Ser Ala Gly Asn Trp Gln Ala Leu
225                 230                 235                 240

Met Leu Pro Val Thr Thr Leu Thr Ile Asn Ala Ser Ser Val Ala Leu
```

```
                    245                 250                 255
Ile Trp Phe Gly Gly Leu Arg Ile Asp Ser Gly Gln Met Gln Val Gly
            260                 265                 270

Ser Leu Ile Ala Phe Leu Ser Tyr Phe Ala Gln Ile Leu Met Ala Val
        275                 280                 285

Leu Met Ala Thr Met Thr Leu Ala Val Leu Pro Arg Ala Ser Val Cys
    290                 295                 300

Ala Glu Arg Ile Thr Glu Val Leu Ser Thr Pro Ala Ala Leu Gly Asn
305                 310                 315                 320

Pro Asp Asn Pro Lys Phe Pro Thr Asp Gly Val Thr Gly Val Val Arg
                325                 330                 335

Leu Ala Gly Ala Thr Phe Thr Tyr Pro Gly Ala Asp Cys Pro Val Leu
            340                 345                 350

Gln Asp Ile Ser Leu Thr Ala Arg Pro Gly Thr Thr Ala Ile Val
        355                 360                 365

Gly Ser Thr Gly Ser Gly Lys Ser Thr Leu Val Ser Leu Ile Cys Arg
    370                 375                 380

Leu Tyr Asp Val Thr Ala Gly Ala Val Leu Val Asp Gly Ile Asp Val
385                 390                 395                 400

Arg Glu Tyr His Thr Glu Arg Leu Trp Ser Ala Ile Gly Leu Val Pro
                405                 410                 415

Gln Arg Ser Tyr Leu Phe Ser Gly Thr Val Ala Asp Asn Leu Arg Tyr
            420                 425                 430

Gly Gly Gly Pro Asp Gln Val Val Thr Glu Gln Glu Met Trp Glu Ala
    435                 440                 445

Leu Arg Val Ala Ala Ala Asp Gly Phe Val Gln Thr Asp Gly Leu Gln
    450                 455                 460

Thr Arg Val Ala Gln Gly Gly Val Asn Phe Ser Gly Gly Gln Arg Gln
465                 470                 475                 480

Arg Leu Ala Ile Ala Arg Ala Val Ile Arg Pro Ala Ile Tyr Val
                485                 490                 495

Phe Asp Asp Ala Phe Ser Ala Leu Asp Val His Thr Asp Ala Lys Val
            500                 505                 510

His Ala Ser Leu Arg Gln Val Ser Gly Asp Ala Thr Ile Ile Val Val
        515                 520                 525

Thr Gln Arg Ile Ser Asn Ala Ala Gln Ala Asp Gln Val Ile Val Val
    530                 535                 540

Asp Asn Gly Lys Ile Val Gly Thr Gly Thr His Glu Thr Leu Leu Ala
545                 550                 555                 560

Asp Cys Pro Thr Tyr Ala Glu Phe Ala Ala Ser Gln Ser Leu Ser Ala
                565                 570                 575

Thr Val Gly Gly Val Gly
            580
```

<210> SEQ ID NO 11
<211> LENGTH: 468
<212> TYPE: PRT
<213> ORGANISM: Mycobacterium tuberculosis

<400> SEQUENCE: 11

```
Met Ser Tyr Val Ile Ala Ala Pro Glu Met Leu Ala Thr Ala Ala
1               5                   10                  15

Asp Val Asp Gly Ile Gly Ser Ala Ile Arg Ala Ala Ser Ala Ser Ala
                20                  25                  30

Ala Gly Pro Thr Thr Gly Leu Leu Ala Ala Ala Ala Asp Glu Val Ser
```

```
                  35                  40                  45
Ser Ala Ala Ala Ala Leu Phe Ser Glu Tyr Ala Arg Glu Cys Gln Glu
 50                  55                  60
Val Leu Lys Gln Ala Ala Ala Phe His Gly Glu Phe Thr Arg Ala Leu
 65                  70                  75                  80
Ala Ala Ala Gly Ala Ala Tyr Ala Gln Ala Glu Ala Ser Asn Thr Ala
                 85                  90                  95
Ala Met Ser Gly Thr Ala Gly Ser Gly Ala Leu Gly Ser Val Gly
                100                 105                 110
Met Leu Ser Gly Asn Pro Leu Thr Ala Leu Met Met Gly Gly Thr Gly
                115                 120                 125
Glu Pro Ile Leu Ser Asp Arg Val Leu Ala Ile Ile Asp Ser Ala Tyr
    130                 135                 140
Ile Arg Pro Ile Phe Gly Pro Asn Asn Pro Val Ala Gln Tyr Thr Pro
145                 150                 155                 160
Glu Gln Trp Trp Pro Phe Ile Gly Asn Leu Ser Leu Asp Gln Ser Ile
                165                 170                 175
Ala Gln Gly Val Thr Leu Leu Asn Asn Gly Ile Asn Ala Glu Leu Gln
                180                 185                 190
Asn Gly His Asp Val Val Phe Gly Tyr Ser Gln Ser Ala Ala Val
        195                 200                 205
Ala Thr Asn Glu Ile Arg Ala Leu Met Ala Leu Pro Pro Gly Gln Ala
    210                 215                 220
Pro Asp Pro Ser Arg Leu Ala Phe Thr Leu Ile Gly Asn Ile Asn Asn
225                 230                 235                 240
Pro Asn Gly Gly Val Leu Glu Arg Tyr Val Gly Leu Tyr Leu Pro Phe
                245                 250                 255
Leu Asp Met Ser Phe Asn Gly Ala Thr Pro Pro Asp Ser Pro Tyr Gln
                260                 265                 270
Thr Tyr Met Tyr Thr Gly Gln Tyr Asp Gly Tyr Ala His Asn Pro Gln
                275                 280                 285
Tyr Pro Leu Asn Ile Leu Ser Asp Leu Asn Ala Phe Met Gly Ile Arg
    290                 295                 300
Trp Val His Asn Ala Tyr Pro Phe Thr Ala Ala Glu Val Ala Asn Ala
305                 310                 315                 320
Val Pro Leu Pro Thr Ser Pro Gly Tyr Thr Gly Asn Thr His Tyr Tyr
                325                 330                 335
Met Phe Leu Thr Gln Asp Leu Pro Leu Leu Gln Pro Ile Arg Ala Ile
                340                 345                 350
Pro Phe Val Gly Thr Pro Ile Ala Glu Leu Ile Gln Pro Asp Leu Arg
                355                 360                 365
Val Leu Val Asp Leu Gly Tyr Gly Tyr Gly Tyr Ala Asp Val Pro Thr
    370                 375                 380
Pro Ala Ser Leu Phe Ala Pro Ile Asn Pro Ile Ala Val Ala Ser Ala
385                 390                 395                 400
Leu Ala Thr Gly Thr Val Gln Gly Pro Gln Ala Ala Leu Val Ser Ile
                405                 410                 415
Gly Leu Leu Pro Gln Ser Ala Leu Pro Asn Thr Tyr Pro Tyr Leu Pro
                420                 425                 430
Ser Ala Asn Pro Gly Leu Met Phe Asn Phe Gly Gln Ser Ser Val Thr
        435                 440                 445
Glu Leu Ser Val Leu Ser Gly Ala Leu Gly Ser Val Ala Arg Leu Ile
    450                 455                 460
```

```
Pro Pro Ile Ala
465

<210> SEQ ID NO 12
<211> LENGTH: 3716
<212> TYPE: PRT
<213> ORGANISM: Mycobacterium tuberculosis

<400> SEQUENCE: 12

Met Glu Phe Pro Val Leu Pro Pro Glu Ile Asn Ser Val Leu Met Tyr
1               5                   10                  15

Ser Gly Ala Gly Ser Ser Pro Leu Leu Ala Ala Ala Ala Ala Trp Asp
            20                  25                  30

Gly Leu Ala Glu Glu Leu Gly Ser Ala Ala Val Ser Phe Gly Gln Val
        35                  40                  45

Thr Ser Gly Leu Thr Ala Gly Val Trp Gln Gly Ala Ala Ala Ala Ala
    50                  55                  60

Met Ala Ala Ala Ala Pro Tyr Ala Gly Trp Leu Gly Ser Val Ala
65                  70                  75                  80

Ala Ala Ala Glu Ala Val Ala Gly Gln Ala Arg Val Val Gly Val
                85                  90                  95

Phe Glu Ala Ala Leu Ala Ala Thr Val Asp Pro Ala Leu Val Ala Ala
            100                 105                 110

Asn Arg Ala Arg Leu Val Ala Leu Ala Val Ser Asn Leu Leu Gly Gln
            115                 120                 125

Asn Thr Pro Ala Ile Ala Ala Glu Ala Glu Tyr Glu Leu Met Trp
    130                 135                 140

Ala Ala Asp Val Ala Ala Met Ala Gly Tyr His Ser Gly Ala Ser Ala
145                 150                 155                 160

Ala Ala Ala Ala Leu Pro Ala Phe Ser Pro Pro Ala Gln Ala Leu Gly
                165                 170                 175

Gly Gly Val Gly Ala Phe Leu Thr Ala Leu Phe Ala Ser Pro Ala Lys
            180                 185                 190

Ala Leu Ser Leu Asn Ala Gly Leu Gly Asn Val Gly Asn Tyr Asn Val
            195                 200                 205

Gly Leu Gly Asn Val Gly Val Phe Asn Leu Gly Ala Gly Asn Val Gly
        210                 215                 220

Gly Gln Asn Leu Gly Phe Gly Asn Ala Gly Thr Asn Val Gly Phe
225                 230                 235                 240

Gly Asn Leu Gly Asn Gly Asn Val Gly Phe Gly Asn Ser Gly Leu Gly
                245                 250                 255

Ala Gly Leu Ala Gly Leu Gly Asn Ile Gly Leu Gly Asn Ala Gly Ser
            260                 265                 270

Ser Asn Tyr Gly Phe Ala Asn Leu Gly Val Gly Asn Ile Gly Phe Gly
        275                 280                 285

Asn Thr Gly Thr Asn Asn Val Gly Val Gly Leu Thr Gly Asn His Leu
    290                 295                 300

Thr Gly Ile Gly Gly Leu Asn Ser Gly Thr Gly Asn Ile Gly Leu Phe
305                 310                 315                 320

Asn Ser Gly Thr Gly Asn Val Gly Phe Phe Asn Ser Gly Thr Gly Asn
                325                 330                 335

Phe Gly Val Phe Asn Ser Gly Asn Tyr Asn Thr Gly Val Gly Asn Ala
            340                 345                 350

Gly Thr Ala Ser Thr Gly Leu Phe Asn Ala Gly Asn Phe Asn Thr Gly
        355                 360                 365
```

```
Val Val Asn Val Gly Ser Tyr Asn Thr Gly Ser Phe Asn Ala Gly Asp
    370                 375                 380

Thr Asn Thr Gly Gly Phe Asn Pro Gly Gly Val Asn Thr Gly Trp Leu
385                 390                 395                 400

Asn Thr Gly Asn Thr Asn Thr Gly Ile Ala Asn Ser Gly Asn Val Asn
                405                 410                 415

Thr Gly Ala Phe Ile Ser Gly Asn Phe Asn Asn Gly Val Leu Trp Val
            420                 425                 430

Gly Asp Tyr Gln Gly Leu Phe Gly Val Ser Ala Gly Ser Ser Ile Pro
        435                 440                 445

Ala Ile Pro Ile Gly Leu Val Leu Asn Gly Asp Ile Gly Pro Ile Thr
    450                 455                 460

Ile Gln Pro Ile Pro Ile Leu Pro Thr Ile Pro Leu Ser Ile His Gln
465                 470                 475                 480

Thr Val Asn Leu Gly Pro Leu Val Val Pro Asp Ile Val Ile Pro Ala
                485                 490                 495

Phe Gly Gly Gly Ile Gly Ile Pro Ile Asn Ile Gly Pro Leu Thr Ile
            500                 505                 510

Thr Pro Ile Thr Leu Phe Ala Gln Gln Thr Phe Val Asn Gln Leu Pro
        515                 520                 525

Phe Pro Thr Phe Ser Leu Gly Lys Ile Thr Ile Pro Gln Ile Gln Thr
    530                 535                 540

Phe Asp Ser Asn Gly Gln Leu Val Ser Phe Ile Gly Pro Ile Val Ile
545                 550                 555                 560

Asp Thr Thr Ile Pro Gly Pro Thr Asn Pro Gln Ile Asp Leu Thr Ile
                565                 570                 575

Arg Trp Asp Thr Pro Pro Ile Thr Leu Phe Pro Asn Gly Ile Ser Ala
            580                 585                 590

Pro Asp Asn Pro Leu Gly Leu Leu Val Ser Val Ser Ile Ser Asn Pro
        595                 600                 605

Gly Phe Thr Ile Pro Gly Phe Ser Val Pro Ala Gln Pro Leu Pro Leu
    610                 615                 620

Ser Ile Asp Ile Glu Gly Gln Ile Asp Gly Phe Ser Thr Pro Pro Ile
625                 630                 635                 640

Thr Ile Asp Arg Ile Pro Leu Thr Val Gly Gly Val Thr Ile Gly
                645                 650                 655

Pro Ile Thr Ile Gln Gly Leu His Ile Pro Ala Ala Pro Gly Val Gly
            660                 665                 670

Asn Thr Thr Thr Ala Pro Ser Ser Gly Phe Phe Asn Ser Gly Ala Gly
        675                 680                 685

Gly Val Ser Gly Phe Gly Asn Val Gly Ala Gly Ser Ser Gly Trp Trp
    690                 695                 700

Asn Gln Ala Pro Ser Ala Leu Leu Gly Ala Gly Ser Gly Val Gly Asn
705                 710                 715                 720

Val Gly Thr Leu Gly Ser Gly Val Leu Asn Leu Gly Ser Gly Ile Ser
                725                 730                 735

Gly Phe Tyr Asn Thr Ser Val Leu Pro Phe Gly Thr Pro Ala Ala Val
            740                 745                 750

Ser Gly Ile Gly Asn Leu Gly Gln Gln Leu Ser Gly Val Ser Ala Ala
        755                 760                 765

Gly Thr Thr Leu Arg Ser Met Leu Ala Gly Asn Leu Gly Leu Ala Asn
    770                 775                 780

Val Gly Asn Phe Asn Thr Gly Phe Gly Asn Val Gly Asp Val Asn Leu
785                 790                 795                 800
```

-continued

Gly Ala Ala Asn Ile Gly Gly His Asn Leu Gly Leu Gly Asn Val Gly
                805                 810                 815

Asp Gly Asn Leu Gly Leu Gly Asn Ile Gly His Gly Asn Leu Gly Phe
                820                 825                 830

Ala Asn Leu Gly Leu Thr Ala Gly Ala Gly Val Gly Asn Val Gly
            835                 840                 845

Phe Gly Asn Ala Gly Ile Asn Asn Tyr Gly Leu Ala Asn Met Gly Val
850                 855                 860

Gly Asn Ile Gly Phe Ala Asn Thr Gly Thr Gly Asn Ile Gly Ile Gly
865                 870                 875                 880

Leu Val Gly Asp His Arg Thr Gly Ile Gly Gly Leu Asn Ser Gly Ile
                885                 890                 895

Gly Asn Ile Gly Leu Phe Asn Ser Gly Thr Gly Asn Val Gly Phe Phe
                900                 905                 910

Asn Ser Gly Thr Gly Asn Phe Gly Ile Gly Asn Ser Gly Arg Phe Asn
            915                 920                 925

Thr Gly Ile Gly Asn Ser Gly Thr Ala Ser Thr Gly Leu Phe Asn Ala
        930                 935                 940

Gly Ser Phe Ser Thr Gly Ile Ala Asn Thr Gly Asp Tyr Asn Thr Gly
945                 950                 955                 960

Ser Phe Asn Ala Gly Asp Thr Asn Thr Gly Gly Phe Asn Pro Gly Gly
                965                 970                 975

Ile Asn Thr Gly Trp Phe Asn Thr Gly His Ala Asn Thr Gly Leu Ala
            980                 985                 990

Asn Ala Gly Thr Phe Gly Thr Gly Ala Phe Met Thr Gly Asp Tyr Ser
        995                 1000                1005

Asn Gly Leu Leu Trp Arg Gly Gly Tyr Glu Gly Leu Val Gly Val
    1010                1015                1020

Arg Val Gly Pro Thr Ile Ser Gln Phe Pro Val Thr Val His Ala
    1025                1030                1035

Ile Gly Gly Val Gly Pro Leu His Val Ala Pro Val Pro Val Pro
    1040                1045                1050

Ala Val His Val Glu Ile Thr Asp Ala Thr Val Gly Leu Gly Pro
    1055                1060                1065

Phe Thr Val Pro Pro Ile Ser Ile Pro Ser Leu Pro Ile Ala Ser
    1070                1075                1080

Ile Thr Gly Ser Val Asp Leu Ala Ala Asn Thr Ile Ser Pro Ile
    1085                1090                1095

Arg Ala Leu Asp Pro Leu Ala Gly Ser Ile Gly Leu Phe Leu Glu
    1100                1105                1110

Pro Phe Arg Leu Ser Asp Pro Phe Ile Thr Ile Asp Ala Phe Gln
    1115                1120                1125

Val Val Ala Gly Val Leu Phe Leu Glu Asn Ile Ile Val Pro Gly
    1130                1135                1140

Leu Thr Val Ser Gly Gln Ile Leu Val Thr Pro Thr Pro Ile Pro
    1145                1150                1155

Leu Thr Leu Asn Leu Asp Thr Thr Pro Trp Thr Leu Phe Pro Asn
    1160                1165                1170

Gly Phe Thr Ile Pro Ala Gln Thr Pro Val Thr Val Gly Met Glu
    1175                1180                1185

Val Ala Asn Asp Gly Phe Phe Phe Pro Gly Gly Leu Thr Phe
    1190                1195                1200

Pro Arg Ala Ser Ala Gly Val Thr Gly Leu Ser Val Gly Leu Asp

-continued

```
            1205                1210                1215

Ala Phe Thr Leu Leu Pro Asp Gly Phe Thr Leu Asp Thr Val Pro
    1220                1225                1230

Ala Thr Phe Asp Gly Thr Ile Leu Ile Gly Asp Ile Pro Ile Pro
    1235                1240                1245

Ile Ile Asp Val Pro Ala Val Pro Gly Phe Gly Asn Thr Thr Thr
    1250                1255                1260

Ala Pro Ser Ser Gly Phe Phe Asn Thr Gly Gly Gly Gly Gly Ser
    1265                1270                1275

Gly Phe Ala Asn Val Gly Ala Gly Thr Ser Gly Trp Trp Asn Gln
    1280                1285                1290

Gly His Asp Val Leu Ala Gly Ala Gly Ser Gly Val Ala Asn Ala
    1295                1300                1305

Gly Thr Leu Ser Ser Gly Val Leu Asn Val Ser Gly Ile Ser
    1310                1315                1320

Gly Trp Tyr Asn Thr Ser Thr Leu Gly Ala Gly Thr Pro Ala Val
    1325                1330                1335

Val Ser Gly Ile Gly Asn Leu Gly Gln Gln Leu Ser Gly Phe Leu
    1340                1345                1350

Ala Asn Gly Thr Val Leu Asn Arg Ser Pro Ile Val Asn Ile Gly
    1355                1360                1365

Trp Ala Asp Val Gly Ala Phe Asn Thr Gly Leu Gly Asn Val Gly
    1370                1375                1380

Asp Leu Asn Trp Gly Ala Ala Asn Ile Gly Ala Gln Asn Leu Gly
    1385                1390                1395

Leu Gly Asn Leu Gly Ser Gly Asn Val Gly Phe Gly Asn Ile Gly
    1400                1405                1410

Ala Gly Asn Val Gly Phe Ala Asn Ser Gly Pro Ala Val Gly Leu
    1415                1420                1425

Ala Gly Leu Gly Asn Val Gly Leu Ser Asn Ala Gly Ser Asn Asn
    1430                1435                1440

Trp Gly Leu Ala Asn Leu Gly Val Gly Asn Ile Gly Leu Ala Asn
    1445                1450                1455

Thr Gly Thr Gly Asn Ile Gly Ile Gly Leu Val Gly Asp Tyr Gln
    1460                1465                1470

Thr Gly Ile Gly Gly Leu Asn Ser Gly Ser Gly Asn Ile Gly Leu
    1475                1480                1485

Phe Asn Ser Gly Thr Gly Asn Val Gly Phe Phe Asn Thr Gly Thr
    1490                1495                1500

Gly Asn Phe Gly Leu Phe Asn Ser Gly Ser Phe Asn Thr Gly Ile
    1505                1510                1515

Gly Asn Ser Gly Thr Gly Ser Thr Gly Leu Phe Asn Ala Gly Asn
    1520                1525                1530

Phe Asn Thr Gly Ile Ala Asn Pro Gly Ser Tyr Asn Thr Gly Ser
    1535                1540                1545

Phe Asn Val Gly Asp Thr Asn Thr Gly Gly Phe Asn Pro Gly Asp
    1550                1555                1560

Ile Asn Thr Gly Trp Phe Asn Thr Gly Ile Met Asn Thr Gly Thr
    1565                1570                1575

Arg Asn Thr Gly Ala Leu Met Ser Gly Thr Asp Ser Asn Gly Met
    1580                1585                1590

Leu Trp Arg Gly Asp His Glu Gly Leu Phe Gly Leu Ser Tyr Gly
    1595                1600                1605
```

```
Ile Thr Ile Pro Gln Phe Pro Ile Arg Ile Thr Thr Thr Gly Gly
1610                1615                1620

Ile Gly Pro Ile Val Ile Pro Asp Thr Thr Ile Leu Pro Pro Leu
1625                1630                1635

His Leu Gln Ile Thr Gly Asp Ala Asp Tyr Ser Phe Thr Val Pro
1640                1645                1650

Asp Ile Pro Ile Pro Ala Ile His Ile Gly Ile Asn Gly Val Val
1655                1660                1665

Thr Val Gly Phe Thr Ala Pro Glu Ala Thr Leu Leu Ser Ala Leu
1670                1675                1680

Lys Asn Asn Gly Ser Phe Ile Ser Phe Gly Pro Ile Thr Leu Ser
1685                1690                1695

Asn Ile Asp Ile Pro Pro Met Asp Phe Thr Leu Gly Leu Pro Val
1700                1705                1710

Leu Gly Pro Ile Thr Gly Gln Leu Gly Pro Ile His Leu Glu Pro
1715                1720                1725

Ile Val Val Ala Gly Ile Gly Val Pro Leu Glu Ile Glu Pro Ile
1730                1735                1740

Pro Leu Asp Ala Ile Ser Leu Ser Glu Ser Ile Pro Ile Arg Ile
1745                1750                1755

Pro Val Asp Ile Pro Ala Ser Val Ile Asp Gly Ile Ser Met Ser
1760                1765                1770

Glu Val Val Pro Ile Asp Ala Ser Val Asp Ile Pro Ala Val Thr
1775                1780                1785

Ile Thr Gly Thr Thr Ile Ser Ala Ile Pro Leu Gly Phe Asp Ile
1790                1795                1800

Arg Thr Ser Ala Gly Pro Leu Asn Ile Pro Ile Ile Asp Ile Pro
1805                1810                1815

Ala Ala Pro Gly Phe Gly Asn Ser Thr Gln Met Pro Ser Ser Gly
1820                1825                1830

Phe Phe Asn Thr Gly Ala Gly Gly Gly Ser Gly Ile Gly Asn Leu
1835                1840                1845

Gly Ala Gly Val Ser Gly Leu Leu Asn Gln Ala Gly Ala Gly Ser
1850                1855                1860

Leu Val Gly Thr Leu Ser Gly Leu Gly Asn Ala Gly Thr Leu Ala
1865                1870                1875

Ser Gly Val Leu Asn Ser Gly Thr Ala Ile Ser Gly Leu Phe Asn
1880                1885                1890

Val Ser Thr Leu Asp Ala Thr Thr Pro Ala Val Ile Ser Gly Phe
1895                1900                1905

Ser Asn Leu Gly Asp His Met Ser Gly Val Ser Ile Asp Gly Leu
1910                1915                1920

Ile Ala Ile Leu Thr Phe Pro Pro Ala Glu Ser Val Phe Asp Gln
1925                1930                1935

Ile Ile Asp Ala Ala Ile Ala Glu Leu Gln His Leu Asp Ile Gly
1940                1945                1950

Asn Ala Leu Ala Leu Gly Asn Val Gly Gly Val Asn Leu Gly Leu
1955                1960                1965

Ala Asn Val Gly Glu Phe Asn Leu Gly Ala Gly Asn Val Gly Asn
1970                1975                1980

Ile Asn Val Gly Ala Gly Asn Leu Gly Gly Ser Asn Leu Gly Leu
1985                1990                1995

Gly Asn Val Gly Thr Gly Asn Leu Gly Phe Gly Asn Ile Gly Ala
2000                2005                2010
```

-continued

```
Gly Asn Phe Gly Phe Gly Asn Ala Gly Leu Thr Ala Gly Ala Gly
        2015                2020                2025

Gly Leu Gly Asn Val Gly Leu Gly Asn Ala Gly Ser Gly Ser Trp
        2030                2035                2040

Gly Leu Ala Asn Val Gly Val Gly Asn Ile Gly Leu Ala Asn Thr
        2045                2050                2055

Gly Thr Gly Asn Ile Gly Ile Gly Leu Thr Gly Asp Tyr Arg Thr
        2060                2065                2070

Gly Ile Gly Gly Leu Asn Ser Gly Thr Gly Asn Leu Gly Leu Phe
        2075                2080                2085

Asn Ser Gly Thr Gly Asn Ile Gly Phe Phe Asn Thr Gly Thr Gly
        2090                2095                2100

Asn Phe Gly Leu Phe Asn Ser Gly Ser Tyr Ser Thr Gly Val Gly
        2105                2110                2115

Asn Ala Gly Thr Ala Ser Thr Gly Leu Phe Asn Ala Gly Asn Phe
        2120                2125                2130

Asn Thr Gly Leu Ala Asn Ala Gly Ser Tyr Asn Thr Gly Ser Leu
        2135                2140                2145

Asn Val Gly Ser Phe Asn Thr Gly Gly Val Asn Pro Gly Thr Val
        2150                2155                2160

Asn Thr Gly Trp Phe Asn Thr Gly His Thr Asn Thr Gly Leu Phe
        2165                2170                2175

Asn Thr Gly Asn Val Asn Thr Gly Ala Phe Asn Ser Gly Ser Phe
        2180                2185                2190

Asn Asn Gly Ala Leu Trp Thr Gly Asp Tyr His Gly Leu Val Gly
        2195                2200                2205

Phe Ser Phe Ser Ile Asp Ile Ala Gly Ser Thr Leu Leu Asp Leu
        2210                2215                2220

Asn Glu Thr Leu Asn Leu Gly Pro Ile His Ile Glu Gln Ile Asp
        2225                2230                2235

Ile Pro Gly Met Ser Leu Phe Asp Val His Glu Ile Val Glu Ile
        2240                2245                2250

Gly Pro Phe Thr Ile Pro Gln Val Asp Val Pro Ala Ile Pro Leu
        2255                2260                2265

Glu Ile His Glu Ser Ile His Met Asp Pro Ile Val Leu Val Pro
        2270                2275                2280

Ala Thr Thr Ile Pro Ala Gln Thr Arg Thr Ile Pro Leu Asp Ile
        2285                2290                2295

Pro Ala Ser Pro Gly Ser Thr Met Thr Leu Pro Leu Ile Ser Met
        2300                2305                2310

Arg Phe Glu Gly Glu Asp Trp Ile Leu Gly Ser Thr Ala Ala Ile
        2315                2320                2325

Pro Asn Phe Gly Asp Pro Phe Pro Ala Pro Thr Gln Gly Ile Thr
        2330                2335                2340

Ile His Thr Gly Pro Gly Pro Gly Thr Thr Gly Glu Leu Lys Ile
        2345                2350                2355

Ser Ile Pro Gly Phe Glu Ile Pro Gln Ile Ala Thr Thr Arg Phe
        2360                2365                2370

Leu Leu Asp Val Asn Ile Ser Gly Gly Leu Pro Ala Phe Thr Leu
        2375                2380                2385

Phe Ala Gly Gly Leu Thr Ile Pro Thr Asn Ala Ile Pro Leu Thr
        2390                2395                2400

Ile Asp Ala Ser Gly Ala Leu Asp Pro Ile Thr Ile Phe Pro Gly
```

-continued

```
                2405                2410                2415

Gly Tyr Thr Ile Asp Pro Leu Pro Leu His Leu Ala Leu Asn Leu
    2420                2425                2430

Thr Val Pro Asp Ser Ser Ile Pro Ile Ile Asp Val Pro Pro Thr
    2435                2440                2445

Pro Gly Phe Gly Asn Thr Thr Ala Thr Pro Ser Ser Gly Phe Phe
    2450                2455                2460

Asn Ser Gly Ala Gly Gly Val Ser Gly Phe Gly Asn Val Gly Ser
    2465                2470                2475

Asn Leu Ser Gly Trp Trp Asn Gln Ala Ala Ser Ala Leu Ala Gly
    2480                2485                2490

Ser Gly Ser Gly Val Leu Asn Val Gly Thr Leu Gly Ser Gly Val
    2495                2500                2505

Leu Asn Val Gly Ser Gly Val Ser Gly Ile Tyr Asn Thr Ser Val
    2510                2515                2520

Leu Pro Leu Gly Thr Pro Ala Val Leu Ser Gly Leu Gly Asn Val
    2525                2530                2535

Gly His Gln Leu Ser Gly Val Ser Ala Ala Gly Thr Ala Leu Asn
    2540                2545                2550

Gln Ile Pro Ile Leu Asn Ile Gly Leu Ala Asp Val Gly Asn Phe
    2555                2560                2565

Asn Val Gly Phe Gly Asn Val Gly Asp Val Asn Leu Gly Ala Ala
    2570                2575                2580

Asn Leu Gly Ala Gln Asn Leu Gly Leu Gly Asn Val Gly Thr Gly
    2585                2590                2595

Asn Leu Gly Phe Ala Asn Val Gly His Gly Asn Ile Gly Phe Gly
    2600                2605                2610

Asn Ser Gly Leu Thr Ala Gly Ala Ala Gly Leu Gly Asn Thr Gly
    2615                2620                2625

Phe Gly Asn Ala Gly Ser Ala Asn Tyr Gly Phe Ala Asn Gln Gly
    2630                2635                2640

Val Arg Asn Ile Gly Leu Ala Asn Thr Gly Thr Gly Asn Ile Gly
    2645                2650                2655

Ile Gly Leu Val Gly Asp Asn Leu Thr Gly Ile Gly Gly Leu Asn
    2660                2665                2670

Ser Gly Ala Gly Asn Ile Gly Leu Phe Asn Ser Gly Thr Gly Asn
    2675                2680                2685

Ile Gly Phe Phe Asn Ser Gly Thr Gly Asn Phe Gly Ile Gly Asn
    2690                2695                2700

Ser Gly Ser Phe Asn Thr Gly Ile Gly Asn Ser Gly Thr Gly Ser
    2705                2710                2715

Thr Gly Leu Phe Asn Ala Gly Ser Phe Asn Thr Gly Val Ala Asn
    2720                2725                2730

Ala Gly Ser Tyr Asn Thr Gly Ser Phe Asn Ala Gly Asp Thr Asn
    2735                2740                2745

Thr Gly Gly Phe Asn Pro Gly Thr Ile Asn Thr Gly Trp Phe Asn
    2750                2755                2760

Thr Gly His Thr Asn Thr Gly Ile Ala Asn Ser Gly Asn Val Gly
    2765                2770                2775

Thr Gly Ala Phe Met Ser Gly Asn Phe Ser Asn Gly Leu Leu Trp
    2780                2785                2790

Arg Gly Asp His Glu Gly Leu Phe Ser Leu Phe Tyr Ser Leu Asp
    2795                2800                2805
```

```
Val Pro Arg Ile Thr Ile Val Asp Ala His Leu Asp Gly Gly Phe
    2810                2815                2820

Gly Pro Val Val Leu Pro Pro Ile Pro Val Pro Ala Val Asn Ala
    2825                2830                2835

His Leu Thr Gly Asn Val Ala Met Gly Ala Phe Thr Ile Pro Gln
    2840                2845                2850

Ile Asp Ile Pro Ala Leu Thr Pro Asn Ile Thr Gly Ser Ala Ala
    2855                2860                2865

Phe Arg Ile Val Val Gly Ser Val Arg Ile Pro Pro Val Ser Val
    2870                2875                2880

Ile Val Glu Gln Ile Ile Asn Ala Ser Val Gly Ala Glu Met Arg
    2885                2890                2895

Ile Asp Pro Phe Glu Met Trp Thr Gln Gly Thr Asn Gly Leu Gly
    2900                2905                2910

Ile Thr Phe Tyr Ser Phe Gly Ser Ala Asp Gly Ser Pro Tyr Ala
    2915                2920                2925

Thr Gly Pro Leu Val Phe Gly Ala Gly Thr Ser Asp Gly Ser His
    2930                2935                2940

Leu Thr Ile Ser Ala Ser Ser Gly Ala Phe Thr Thr Pro Gln Leu
    2945                2950                2955

Glu Thr Gly Pro Ile Thr Leu Gly Phe Gln Val Pro Gly Ser Val
    2960                2965                2970

Asn Ala Ile Thr Leu Phe Pro Gly Gly Leu Thr Phe Pro Ala Thr
    2975                2980                2985

Ser Leu Leu Asn Leu Asp Val Thr Ala Gly Ala Gly Gly Val Asp
    2990                2995                3000

Ile Pro Ala Ile Thr Trp Pro Glu Ile Ala Ala Ser Ala Asp Gly
    3005                3010                3015

Ser Val Tyr Val Leu Ala Ser Ser Ile Pro Leu Ile Asn Ile Pro
    3020                3025                3030

Pro Thr Pro Gly Ile Gly Asn Ser Thr Ile Thr Pro Ser Ser Gly
    3035                3040                3045

Phe Phe Asn Ala Gly Ala Gly Gly Gly Ser Gly Phe Gly Asn Phe
    3050                3055                3060

Gly Ala Gly Thr Ser Gly Trp Trp Asn Gln Ala His Thr Ala Leu
    3065                3070                3075

Ala Gly Ala Gly Ser Gly Phe Ala Asn Val Gly Thr Leu His Ser
    3080                3085                3090

Gly Val Leu Asn Leu Gly Ser Gly Val Ser Gly Ile Tyr Asn Thr
    3095                3100                3105

Ser Thr Leu Gly Val Gly Thr Pro Ala Leu Val Ser Gly Leu Gly
    3110                3115                3120

Asn Val Gly His Gln Leu Ser Gly Leu Leu Ser Gly Gly Ser Ala
    3125                3130                3135

Val Asn Pro Val Thr Val Leu Asn Ile Gly Leu Ala Asn Val Gly
    3140                3145                3150

Ser His Asn Ala Gly Phe Gly Asn Val Gly Glu Val Asn Leu Gly
    3155                3160                3165

Ala Ala Asn Leu Gly Ala His Asn Leu Gly Phe Gly Asn Ile Gly
    3170                3175                3180

Ala Gly Asn Leu Gly Phe Gly Asn Ile Gly His Gly Asn Val Gly
    3185                3190                3195

Val Gly Asn Ser Gly Leu Thr Ala Gly Val Pro Gly Leu Gly Asn
    3200                3205                3210
```

Val Gly Leu Gly Asn Ala Gly Gly Asn Asn Trp Gly Leu Ala Asn
3215                3220                3225

Val Gly Val Gly Asn Ile Gly Leu Ala Asn Thr Gly Thr Gly Asn
3230                3235                3240

Ile Gly Ile Gly Leu Thr Gly Asp Tyr Gln Thr Gly Ile Gly Gly
3245                3250                3255

Leu Asn Ser Gly Ala Gly Asn Leu Gly Leu Phe Asn Ser Gly Ala
3260                3265                3270

Gly Asn Val Gly Phe Phe Asn Thr Gly Thr Gly Asn Phe Gly Leu
3275                3280                3285

Phe Asn Ser Gly Ser Phe Asn Thr Gly Val Gly Asn Ser Gly Thr
3290                3295                3300

Gly Ser Thr Gly Leu Phe Asn Ala Gly Ser Phe Asn Thr Gly Val
3305                3310                3315

Ala Asn Ala Gly Ser Tyr Asn Thr Gly Ser Phe Asn Val Gly Asp
3320                3325                3330

Thr Asn Thr Gly Gly Phe Asn Pro Gly Ser Ile Asn Thr Gly Trp
3335                3340                3345

Leu Asn Ala Gly Asn Ala Asn Thr Gly Val Ala Asn Ala Gly Asn
3350                3355                3360

Val Asn Thr Gly Ala Phe Val Thr Gly Asn Phe Ser Asn Gly Ile
3365                3370                3375

Leu Trp Arg Gly Asp Tyr Gln Gly Leu Ala Gly Phe Ala Val Gly
3380                3385                3390

Tyr Thr Leu Pro Leu Phe Pro Ala Val Gly Ala Asp Val Ser Gly
3395                3400                3405

Gly Ile Gly Pro Ile Thr Val Leu Pro Pro Ile His Ile Pro Pro
3410                3415                3420

Ile Pro Val Gly Phe Ala Ala Val Gly Gly Ile Gly Pro Ile Ala
3425                3430                3435

Ile Pro Asp Ile Ser Val Pro Ser Ile His Leu Gly Leu Asp Pro
3440                3445                3450

Ala Val His Val Gly Ser Ile Thr Val Asn Pro Ile Thr Val Arg
3455                3460                3465

Thr Pro Pro Val Leu Val Ser Tyr Ser Gln Gly Ala Val Thr Ser
3470                3475                3480

Thr Ser Gly Pro Thr Ser Glu Ile Trp Val Lys Pro Ser Phe Phe
3485                3490                3495

Pro Gly Ile Arg Ile Ala Pro Ser Ser Gly Gly Ala Thr Ser
3500                3505                3510

Thr Gln Gly Ala Tyr Phe Val Gly Pro Ile Ser Ile Pro Ser Gly
3515                3520                3525

Thr Val Thr Phe Pro Gly Thr Ile Pro Leu Asp Pro Ile Asp
3530                3535                3540

Ile Gly Leu Pro Val Ser Leu Thr Ile Pro Gly Phe Thr Ile Pro
3545                3550                3555

Gly Gly Thr Leu Ile Pro Thr Leu Pro Leu Gly Leu Ala Leu Ser
3560                3565                3570

Asn Gly Ile Pro Pro Val Asp Ile Pro Ala Ile Val Leu Asp Arg
3575                3580                3585

Ile Leu Leu Asp Leu His Ala Asp Thr Thr Ile Gly Pro Ile Asn
3590                3595                3600

Val Pro Ile Ala Gly Phe Gly Gly Ala Pro Gly Phe Gly Asn Ser

|      |      | 3605 |      |      | 3610 |      |      | 3615 |      |      |      |

Thr Thr Leu Pro Ser Ser Gly Phe Phe Asn Thr Gly Ala Gly Gly
    3620            3625            3630

Gly Ser Gly Phe Ser Asn Thr Gly Ala Gly Met Ser Gly Leu Leu
    3635            3640            3645

Asn Ala Met Ser Asp Pro Leu Leu Gly Ser Ala Ser Gly Phe Ala
    3650            3655            3660

Asn Phe Gly Thr Gln Leu Ser Gly Ile Leu Asn Arg Gly Ala Gly
    3665            3670            3675

Ile Ser Gly Val Tyr Asn Thr Gly Ala Leu Gly Val Val Thr Ala
    3680            3685            3690

Ala Val Val Ser Gly Phe Gly Asn Val Gly Gln Gln Leu Ser Gly
    3695            3700            3705

Leu Leu Phe Thr Gly Val Gly Pro
    3710            3715

<210> SEQ ID NO 13
<211> LENGTH: 11
<212> TYPE: PRT
<213> ORGANISM: Mycobacterium tuberculosis

<400> SEQUENCE: 13

Gln Thr Val Glu Asp Glu Ala Arg Arg Met Trp
1               5                   10

<210> SEQ ID NO 14
<211> LENGTH: 9
<212> TYPE: PRT
<213> ORGANISM: Mycobacterium tuberculosis

<400> SEQUENCE: 14

Val Ser Ala Ala Ile Ala Gly Leu Phe
1               5

<210> SEQ ID NO 15
<211> LENGTH: 297
<212> TYPE: DNA
<213> ORGANISM: Mycobacterium tuberculosis

<400> SEQUENCE: 15
atggcctcgc gttttatgac ggatccgcac gcgatgcggg acatggcggg ccgttttgag      60
gtgcacgccc agacggtgga ggacgaggct cgccggatgt gggcgtccgc gcaaaacatc     120
tcgggcgcgg gctggagtgg catggccgag gcgacctcgc tagacaccat gacccagatg     180
aatcaggcgt tcgcaacat cgtgaacatg ctgcacgggg tgcgtgacgg gctggttcgc     240
gacgccaaca actacgaaca gcaagagcag gcctcccagc agatcctcag cagctga       297

<210> SEQ ID NO 16
<211> LENGTH: 297
<212> TYPE: DNA
<213> ORGANISM: Mycobacterium tuberculosis

<400> SEQUENCE: 16
atggcctcac gttttatgac ggatccgcac gcgatgcggg acatggcggg ccgttttgag      60
gtgcacgccc agacggtgga ggacgaggct cgccggatgt gggcgtccgc gcaaaacatt     120
tccggtgcgg gctggagtgg catggccgag gcgacctcgc tagacaccat ggcccagatg     180
aatcaggcgt tcgcaacatc gtgaacatg ctgcacgggg tgcgtgacgg gctggttcgc     240
gacgccaaca actacgagca gcaagagcag gcctcccagc agatcctcag cagctaa       297

<210> SEQ ID NO 17
<211> LENGTH: 297
<212> TYPE: DNA
<213> ORGANISM: Mycobacterium tuberculosis

<400> SEQUENCE: 17

| | | | | | |
|---|---|---|---|---|---|
| atggcctcac | gttttatgac | ggatccgcat | gcgatgcggg | acatggcggg | ccgttttgag | 60 |
| gtgcacgccc | agacggtgga | ggacgaggct | cgccggatgt | gggcgtccgc | gcaaaacatt | 120 |
| tccggtgcgg | gctggagtgg | catggccgag | gcgacctcgc | tagacaccat | gacctagatg | 180 |
| aatcaggcgt | ttcgcaacat | cgtgaacatg | ctgcacgggg | tgcgtgacgg | gctggttcgc | 240 |
| gacgccaaca | actacgaaca | gcaagagcag | gcctcccagc | agatcctgag | cagctag | 297 |

<210> SEQ ID NO 18
<211> LENGTH: 297
<212> TYPE: DNA
<213> ORGANISM: Mycobacterium tuberculosis

<400> SEQUENCE: 18

| | | | | | |
|---|---|---|---|---|---|
| atggcaacac | gttttatgac | ggatccgcac | gcgatgcggg | acatggcggg | ccgttttgag | 60 |
| gtgcacgccc | agacggtgga | ggacgaggct | cgccggatgt | gggcgtccgc | gcaaaacatc | 120 |
| tcgggcgcgg | gctggagtgg | catggccgag | gcgacctcgc | tagacaccat | ggcccagatg | 180 |
| aatcaggcgt | ttcgcaacat | cgtgaacatg | ctgcacgggg | tgcgtgacgg | gctggttcgc | 240 |
| gacgccaaca | actacgagca | gcaagagcag | gcctcccagc | agatcctcag | cagctaa | 297 |

<210> SEQ ID NO 19
<211> LENGTH: 297
<212> TYPE: DNA
<213> ORGANISM: Mycobacterium tuberculosis

<400> SEQUENCE: 19

| | | | | | |
|---|---|---|---|---|---|
| atgacctcgc | gttttatgac | ggatccgcac | gcgatgcggg | acatggcggg | ccgttttgag | 60 |
| gtgcacgccc | agacggtgga | ggacgaggct | cgccggatgt | gggcgtccgc | gcaaaacatt | 120 |
| tccggcgcgg | gctggagtgg | catggccgag | gcgacctcgc | tagacaccat | gacccagatg | 180 |
| aatcaggcgt | ttcgcaacat | cgtgaacatg | ctgcacgggg | tgcgtgacgg | gctggttcgc | 240 |
| gacgccaaca | actacgaaca | gcaagagcag | gcctcccagc | agatcctcag | cagctga | 297 |

<210> SEQ ID NO 20
<211> LENGTH: 435
<212> TYPE: DNA
<213> ORGANISM: Mycobacterium tuberculosis

<400> SEQUENCE: 20

| | | | | | |
|---|---|---|---|---|---|
| atgtcataca | tgattgccac | accagcggcg | ttgacggcgg | cggcaacgga | tatcgacggg | 60 |
| attggctcgg | cggttagcgt | tgcgaacgcc | gcggcggtcg | ccgcgacaac | cggagtgctg | 120 |
| gccgccggtg | gcgatgaagt | gttggcggcc | atcgctaggc | tgttcaacgc | aaacgccgag | 180 |
| gaatatcacg | ccctcagcgc | gcaggtgcg | gcgtttcaaa | ccctgtttgt | gcgcaccttg | 240 |
| actgggggt | gcggagtctt | tcgccggcgc | cgaggccgcc | aatgcgtcac | agctgcagag | 300 |
| catcgcgcg | caggtgcggg | gcgccgtcaa | cgccgtcgcc | ggtcaggtga | cgggcaatgg | 360 |
| cggctccggc | aacagcggca | cttcggctgc | ggcggccaac | ccgaattccg | acaacacagc | 420 |
| gagcatcgcc | gatag | | | | | 435 |

<210> SEQ ID NO 21
<211> LENGTH: 2085
<212> TYPE: DNA
<213> ORGANISM: Mycobacterium tuberculosis

<400> SEQUENCE: 21

```
gtgtcgttgg tgatcgcgac gccgcagctg ctggcaactg cggctttgga tttagcgagt      60
attggttcgc aggtgagcgc ggctaatgcg gccgcggcga tgccgacgac ggaagtggtg     120
gctgcggctg ccgatgaagt gtcggcggcg attgcggggt tgttcggggc ccatgctcgg     180
cagtatcagg cgctcagcgt acaggtggca gcgtttcacg agcagtttgt gcaggcgttg     240
actgcggccg cgggtcggta tgccagcact gaggccgctg ttgagcggag tctgctgggt     300
gcggtgaatg cgcccaccga ggcgcttttg gggcgcccgt tgatcggaaa cggcgccgac     360
gggacggcac ccgggcagcc tggcgcggcc ggcgggttgc tgtttggcaa cggtggcaac     420
ggcgcggctg cgggttcgg tcaaaccggc ggcagcggag gcgcggccgg gttgatcggc      480
aacggcggca acggcgggc cggtggtacc ggcgcggccg gcggtgccgg tgggaacggg     540
gggtggttgt ggggcaacgg cggcaacggc ggtgtcggcg caccagcgt ggccgcaggc      600
atcggggtg cgggcggtaa cggcggcaac gccgggctgt cggccatgg cggcgccggt       660
ggtaccggcg gcgccggcct cgccggggca acgggtca atcccacgcc cggccccgcg       720
gccagcaccg gggacagccc ggcagatgtg tccggcatcg gtgatcaaac cggcggcgac     780
ggcggcacgg gcggccatgg cactgccggc acgccgaccg gtggcaccgg cggcgacggt     840
gccaccgcga cggcaggctc gggcaaggcc accggcggtg ccgtggtga cggcggtacc      900
gccgctgccg gtggcggcgg cggcaacggc ggcgacggcg agtcgcgca gggcgacatt      960
gcgagcgcct ttggcggtga tggtggcaac gggtccgacg tgtagccgc cggcagtggg     1020
ggtggtagcg gcggcgccgg aggcggcgct ttcgtacaca tcgccactgc cacctctacc    1080
ggtggtagcg gcggttttcgg tggtaacggg gctgccagtg ccgcctccgg cgccgacggt    1140
ggcgcagggg gagctggcgg caatggtggc gccggcgggt tgctattcgg tgatggcggc    1200
aacggtggcg ccggtggcgc gggtggtatc ggtggtgacg gcgccacggg ggggcccggg    1260
ggaagcggcg gcaacgctgg catcgcgagg tttgacagcc cagaccccga ggcagaaccc    1320
gatgtggtcg gcgcaagg tggtgatggc ggcaagggcg gcagcggcct tggcgtcggc     1380
ggcgccggcg ggaccggcgg cgcgggcggc aacggcggcg ccggcgggtt gttgttcggc    1440
aacggcggca acggcggcaa cgccggggcc ggcggggatg gcggcgccgg cgttgccggt    1500
ggggttggcg gtaacggcgg cggtggtggc accgcgacgt tcacgaaga cccggtcgct    1560
ggtgtctggg cggtcggtgg cgtaggtggt gatggtggct ccggcggcag ctcgcttggt    1620
gtcgcgggg tgggcggagc cggtggcgtg ggtggcaagg gtggcgccag cggcatgttg    1680
atcggcaacg gcggcaacgg tggcagcggc ggagtcggtg gggccggtgg agtcggcggg    1740
gctggcggtg acgcggcaa cggcggctcc ggtggcaacg ccagtacttt tggcgatgag    1800
aactccatcg gcggggccgg cgggacgggc ggcaacgggg gcaacggcgc aaacggcggt    1860
aacggtggcg ctggcggtat tgccggcggt gcgggtgggt ccggagggtt cctcagcggt    1920
gccgcaggag tcagcggcgc tgacggtatc ggtggcgcgg gcggcgcagg cggtgccggt    1980
ggcgcgggcg gtagcggcgg tgaggcaggc gcgggggcc tcaccaacgg ccccgggtcc    2040
cctggcgttt ccggcaccga aggcatggcc ggcgcgcccg gctag                    2085
```

<210> SEQ ID NO 22
<211> LENGTH: 978

```
<212> TYPE: DNA
<213> ORGANISM: Mycobacterium tuberculosis

<400> SEQUENCE: 22
atgcatcagg tggaccccaa cttgacacgt cgcaagggac gattggcggc actggctatc    60
gcggcgatgg ccagcgccag cctggtgacc gttgcggtgc ccgcgaccgc caacgccgat   120
ccggagccag cgccccggt acccacaacg gccgcctcgc cgccgtcgac cgctgcagcg    180
ccacccgcac cggcgacacc tgttgccccc ccaccaccgg ccgccgccaa cacgccgaat   240
gcccagccgg cgatcccaa cgcagcacct ccgccggccg acccgaacgc accgccgcca    300
cctgtcattg ccccaaacgc accccaacct gtccggatcg acaacccggt tggaggattc   360
agcttcgcgc tgcctgctgg ctgggtggag tctgacgccg cccacttcga ctacggttca   420
gcactcctca gcaaaaccac cggggacccg ccatttcccg acagccgcc gccggtggcc    480
aatgacaccc gtatcgtgct cggccggcta gaccaaaagc tttacgccag cgccgaagcc   540
accgactcca aggccgcggc ccggttgggc tcggacatgg tgagttcta tatgccctac    600
ccgggcaccc ggatcaacca ggaaaccgtc tcgctcgacg ccaacggggt gtctggaagc   660
gcgtcgtatt acgaagtcaa gttcagcgat ccgagtaagc cgaacggcca gatctggacg   720
ggcgtaatcg gctcgcccgc ggcgaacgca ccggacgccg ggcccctca gcgctggttt    780
gtggtatggc tcgggaccgc caacaacccg gtggacaagg gcgcggccaa ggcgctggcc   840
gaatcgatcc ggcctttggt cgcccgccg ccggcgccgg caccggctcc tgcagagccc    900
gctccggcgc cggcgccggc cggggaagtc gctcctaccc cgacgacacc gacaccgcag    960
cggaccttac cggcctga                                                978

<210> SEQ ID NO 23
<211> LENGTH: 1749
<212> TYPE: DNA
<213> ORGANISM: Mycobacterium tuberculosis

<400> SEQUENCE: 23
atgctcctgg ccctgctgcg ccagcacatc cgaccgtacc gccggctggt cgcgatgctg    60
atgatgctgc agctggtcag caccctggct tcgctatacc tcccgacggt caacgccgca   120
atcgtcgacg acggcgtcgc caagggcgac accgccacca tcgtacggct gggtgcggtg   180
atgcttgggg tgaccggatt gcaggtgctg tgcgcgatcg gggcggtcta tctgggctcc   240
cggaccgggg cgggtttcgg ccgtgacctg cgctcggcaa tgttcgaaca catcatcacc   300
ttctcggaac gcgagaccgc ccgattcggc gctccgacgt tgttgacccg cagcaccaac   360
gacgtccggc agatcctgtt cctggtccag atgaccgcca ccgtgctggt caccgcaccg   420
atcatgtgcg tcggcggaat catcatggcc atccaccagg aggccgcgct gacatggctg   480
ctgctggtca gcgttccgat tctggccgta gcaaactact ggatcatctc ccacatgctg   540
ccgctcttcc gccgcatgca gagcctgatc gacggcatca accgggtgat gcgcgatcag   600
ctgtccgggg tgcgagtggt ccgcgccttc acccgcgaag ctatgaacg cgacaagttc   660
gcgcaggcca atacggcgct gtcgaatgcc gcactgagcg ccggcaactg gcaagcactg   720
atgctgccgg tgaccacgct gaccatcaac gcatccagcg tcgcactgat ctggttcggt   780
gggctacgca tcgacagcgg ccagatgcag gtcggctccc tgatcgcctt cctgtcctac   840
ttcgcccaga tcctgatggc ggtgttgatg gcgaccatga cgctggccgt gctgccacga   900
gcgtcggtct gcgccgaacg catcaccgag gtgctttcca cgcccgccgc actcggtaac   960
cccgacaatc ccaagttccc gacggacggg gtcacgggcg tagtgcgctt ggctggcgca  1020
```

| | | |
|---|---|---|
| accttrtacct | atcctggcgc cgactgcccg gtgctgcagg acatttcgtt gactgcgcgg | 1080 |
| cccggtacca | ccaccgcgat cgtcggcagt accggttcgg gcaagtcgac actggtgtcg | 1140 |
| ttgatctgcc | ggctctacga cgtcaccgct ggcgcggtct tggttgacgg tatcgacgtc | 1200 |
| cgcgagtacc | acaccgagcg gctctggtca gcgatcgggc tggtgcccca gcgcagctac | 1260 |
| ctcttctccg | gaaccgtcgc ggacaacctg cgctacggcg ggggcccaga ccaggtagtc | 1320 |
| accgagcagg | agatgtggga ggcgctgcgg gtcgccgcgg ccgacggctt tgtacaaaca | 1380 |
| gacgggctgc | agacgcgtgt cgcccaaggt ggtgtcaact tctccggcgg gcagcgccaa | 1440 |
| cggctggcga | tagcccgagc ggtcatccga cgtccggcca tctatgtgtt cgacgacgcg | 1500 |
| ttctccgcac | ttgacgtgca caccgacgcc aaagtccacg catcgctgcg acaggtatct | 1560 |
| ggtgatgcaa | ccatcattgt tgttacacaa cggatttcga atgccgctca ggccgaccag | 1620 |
| gtcatcgttg | tcgataacgg taagatcgtc ggcacgggca cccacgaaac gctgctggcc | 1680 |
| gattgcccca | cctatgccga attcgccgcc tcacaatcgc tgagcgccac ggtcgggggt | 1740 |
| gtagggtga | | 1749 |

<210> SEQ ID NO 24
<211> LENGTH: 1407
<212> TYPE: DNA
<213> ORGANISM: Mycobacterium tuberculosis

<400> SEQUENCE: 24

| | | |
|---|---|---|
| atgtcctacg | tcatcgcggc cccggagatg ttggcaacga cggccgcgga cgtggacggg | 60 |
| atcggttcgg | cgatacgagc ggccagcgcg tccgctgcgg gtccaacgac cggactgctg | 120 |
| gccgcggccg | ccgatgaggt gtcgtcggcc gctgcagcgc tgttcagcga atacgcgcgc | 180 |
| gaatgtcaag | aggtcctaaa gcaggctgcg gcgttccatg gcgagttcac ccgggcgctg | 240 |
| gctgccgccg | gggccgccta tgcccaggct gaagccagca acaccgctgc tatgtcgggc | 300 |
| accgccgggt | ccagcggcgc cctcggttct gtcgggatgc tgtcaggcaa cccgctaacc | 360 |
| gcgttgatga | tgggcggcac cggggaaccg atccttagtg accgcgtctt ggcgatcatt | 420 |
| gacagcgcat | acattcggcc catttttcggg cccaacaacc cggtcgccca gtacacgccc | 480 |
| gagcagtggg | ggccgtttat cgggaacctg tcactggacc aatccatcgc ccagggtgtc | 540 |
| acgctgctga | caacggcat caacgcggaa ctacaaaatg gcatgacgt cgtcgttttc | 600 |
| ggctactcgc | aaagcgccgc ggtagcgacc aatgaaatac gcgctcttat ggcgttacca | 660 |
| ccgggccaag | ccccagatcc aagccggctg gctttcacgt tgatcggtaa tatcaataac | 720 |
| cccaacggcg | gcgtcctcga gcgttacgtg ggcctttacc tcccgttctt ggatatgtcg | 780 |
| ttcaacggtg | cgactccacc ggattccccc taccagacct acatgtacac cggccaatac | 840 |
| gacggctacg | cccacaaccc gcagtacccg ctcaatatct tgtcggacct caacgccttc | 900 |
| atgggcatca | gatgggtgca caacgcgtac cccttcaccg cggccgaggt tgccaatgcc | 960 |
| gtgccgttgc | ccacgtctcc gggctacacc ggcaacaccc attactacat gtttctgacc | 1020 |
| caggacctgc | cgctgttgca gccgattcgc gccatcccct tcgtagggac cccaatagcc | 1080 |
| gagctgattc | agcccgacct acgggtgcta gtcgacttgg gctatggcta cggctacgcc | 1140 |
| gacgtaccca | ccccggccag cctgttcgcg ccaatcaacc cgatcgccgt ggcctcggcc | 1200 |
| ctggcgaccg | ggaccgtgca aggcccccaa gccgccctag taagcatcgg attgttaccg | 1260 |
| cagtccgcgc | tacccaatac gtatccgtat cttccgtcgg cgaatccggg cctgatgttc | 1320 |
| aacttcggtc | aatccagtgt gacggagttg tcggtgctca gtggcgccct cgggtccgta | 1380 | gcgagattga ttccaccgat cgcgtga 1407

<210> SEQ ID NO 25
<211> LENGTH: 11151
<212> TYPE: DNA
<213> ORGANISM: Mycobacterium tuberculosis

<400> SEQUENCE: 25

| | |
|---|---|
| atggagtttc cggtgttgcc accggaaatc aactccgtgc tgatgtattc gggtgcgggg | 60 |
| tcgagcccgt tgctggcggc ggccgcggcg tgggatgggc tggctgagga gttggggtcg | 120 |
| gcggcggtgt cgtttgggca ggtgacgtcg ggcctgacgg cggggggtgtg gcagggtgcg | 180 |
| gcggcggcgg cgatggcggc cgcggcggcg ccgtatgcgg ggtggttggg ttcggtggcg | 240 |
| gccgcggccg aggcggtggc cgggcaggcg cgggtggtgg tgggggtctt tgaggcggcg | 300 |
| ttggcggcga cggtggatcc ggcgctggtg gcggccaacc gggcgcggct ggtggcgttg | 360 |
| gcggtgtcga atctgttggg gcagaacacg ccggcgatcg cggccgccga ggccgagtac | 420 |
| gagctgatgt gggccgccga tgtggcggcg atggccggct accattccgg cgcgtcggct | 480 |
| gctgccgcgc cgttgccggc gttcagccca ccggcgcagg cgctgggggg aggtgtcggc | 540 |
| gcgttcctta ccgccctgtt cgccagccct gcgaaggcgc tgagcctgaa tgcgggtttg | 600 |
| ggcaatgtcg gcaattacaa cgtcggggtg gcaatgtcg gggtgttcaa cctgggcgcg | 660 |
| ggcaatgtgg gtgggcagaa tctgggtttc gggaatgccg gtggcaccaa tgtcgggttc | 720 |
| ggcaacctcg gtaacgggaa tgtcgggttc ggcaactccg gtctgggggc gggcctggcc | 780 |
| ggcttgggca atatcgggtt gggcaatgcg ggcagcagca actatggttt cgcaaacctg | 840 |
| ggtgtgggca acatcggttt cggcaacacc ggcaccaaca acgtcggcgt cgggctcacc | 900 |
| ggcaaccacc tgacgggtat cggggggcctg aattcgggca ccgggaatat cgggttgttc | 960 |
| aactccggca ccgggaatgt ggggttcttc aattcgggga ccgggaactt cggggtgttc | 1020 |
| aactcgggta attacaacac cggtgtcggt aatgcgggga cggccagcac ggggttgttc | 1080 |
| aatgccggca atttcaacac cggcgtggtg aacgtgggca gttacaacac cggcagtttc | 1140 |
| aacgccggcg acaccaacac cggtggcttc aaccccggcg tgtgaacac cggctggctg | 1200 |
| aacaccggca acaccaacac cggcatcgcc aactcgggca acgtcaacac cggcgcgttc | 1260 |
| atctcgggca acttcaacaa cggcgtgctg tgggtgggtg actaccaggg cctgttcggc | 1320 |
| gtctccgccg gctcgtcgat ccccgcaatt cccatcggcc tggtgctcaa cggcgacatc | 1380 |
| ggcccgatca ccatccagcc catcccgatc ctgcccacca tcccgctcag cattcaccaa | 1440 |
| accgtcaact tgggcccgct ggtggttccc gacatcgtga tccccgcctt cggcggcggt | 1500 |
| atcggcatac ccatcaacat cggcccgctg accatcacac ccatcaccct gtttgcccaa | 1560 |
| cagacatttg tcaaccaatt gcccttcc accttcagtt tagggaaaat cacaattcca | 1620 |
| caaatccaaa cctttgattc taacggtcag cttgtcagct ttatcggccc tatcgttatc | 1680 |
| gacaccacca ttcccggacc caccaatcca cagattgatt taacgatcag atgggatacc | 1740 |
| cctccgatca cgctgttccc gaatggcatc agtgctcccg ataatccttt ggggttgctg | 1800 |
| gtgagtgtgt cgatcagtaa cccgggcttt accatcccgg gatttagtgt tcccgcgcag | 1860 |
| ccgttgccgt tgtcgatcga tatcgagggc cagatcgacg ggttcagcac cccgccgatc | 1920 |
| acgatcgatc gcatccccct gaccgtgggg ggcggggtca cgatcggccc catcacgatc | 1980 |
| cagggccttc atatcccggc ggcgccggga gtggggaaca ccaccacggc cccgtcgtcg | 2040 |
| ggattcttca actccggtgc gggtgggggtg tcgggtttcg gcaacgtcgg cgcgggcagc | 2100 |

```
tcgggctggt ggaaccaggc gccgagcgcg ctgttggggg ccggttcggg tgttggcaac    2160
gtgggcaccc tgggctcggg tgtgctcaac ctgggctcag ggatctcggg gttctacaac    2220
accagcgtgt tgcctttcgg gacaccggcg gcggtgtcgg gcatcggcaa cctgggccag    2280
cagctgtcgg gggtgtcggc ggcgggaacc acgctgcgct cgatgctcgc cggcaacctc    2340
gggttggcca atgtgggcaa cttcaacacc gggttcggaa atgtcgggga cgtcaacctg    2400
ggtgcggcca acatcggtgg gcacaacctg ggcctgggca atgtcgggga cggcaacctg    2460
gggttgggca acatcggcca tggcaacctg gggtttgcca acttgggcct gaccgccggc    2520
gcggcggggg tgggcaatgt tggttttggc aatgccggca tcaacaacta tggcttggcg    2580
aacatgggtg tgggcaatat tgggtttgcc aacaccggca cgggcaacat cgggatcggg    2640
ctggtcgggg accatcggac cgggatcggg ggcttgaact ccggcatcgg caatatcggg    2700
ttgttcaact ccggcaccgg caacgtcggg ttcttcaatt ccgggaccgg caacttcggc    2760
atcgggaact ccggccgctt caacaccggg atcggtaata gcgaacggc cagcaccggg    2820 ctcttcaatg ccggcagctt cagcaccggc atcgccaaca ctggtgacta caacacgggc    2880
agcttcaacg ccggcgacac caacaccggt ggcttcaacc cgggcggcat caacaccggc    2940
tggttcaaca ccgggcatgc caacaccggg ttggccaacg cgggcacctt cggcaccggc    3000
gccttcatga cgggcgacta cagcaacggc ctgttgtggc gggcggcta cgagggcctg    3060 gtcggcgtcc gcgtcgggcc cacgatctcc caattcccgg tcaccgtgca cgcgatcggc    3120
ggggtgggcc cgctgcatgt ggcgcccgtc ccggtacccg ccgtgcacgt cgagatcacc    3180
gacgccaccg tcggcctggg tccgttcacc gtcccaccga tcagcattcc ctcacttccc    3240
atcgccagca tcaccggaag cgtggacctg gccgcaaaca ccatctcgcc gattcgcgct    3300
cttgacccgc tcgccggttc gatagggctt tttctcgagc cgttccgcct cagtgaccca    3360
tttatcacca ttgatgcgtt ccaagttgtt gccggtgtct tgttcctaga gaacatcatt    3420
gtgcccggcc tcacggttag cggtcagata ttggtcaccc cgacaccaat tcccctaacc    3480
ctcaacttgg acaccacccc gtggacgctt ttcccgaatg gtttcaccat tcccgcgcaa    3540 accccgtga cggtgggtat ggaggtcgcc aacgacgggt tcaccttctt cccgggtggg    3600
ctgacctttc cgcgggcctc cgccggggtc accggactgt ccgtgggggct ggacgcgttc    3660 acgctgttgc ccgacgggtt caccctcgac accgtgccgg cgaccttcga cggcaccatc    3720
ctcatcggcg atatcccgat cccgatcatc gatgtgccgg cggtgccggg gttcggcaac    3780
accaccacgg ccccatcgtc gggggttcttc aacaccggcg gcggcggtgg atcggggttc    3840
gccaacgtcg gcgcgggcac gtcgggctgg tggaaccagg ggcacgacgt gttagcaggg    3900
gcgggctcgg gagttgccaa tgccggcacg ctgagctcgg gcgtgctgaa cgtcggctcg    3960
gggatctccg ggtggtacaa caccagcacc ctgggagcgg gcaccccggc ggtggtctcg    4020
ggcatcggca acctcggcca gcagctgtcg gggttcttgg caaatgggac cgtgctcaac    4080
cggagcccca ttgtcaatat cgggtgggcc gatgtgggcg cgttcaacac cgggttgggc    4140
aatgtggggg acctcaactg gggtgcgcc aacatcggcg cgcagaacct gggcctgggc    4200
aatctcggca gcgggaacgt cgggttcggc aacatcggtg ccggcaacgt cgggttcgcc    4260
aactcgggtc cggcggtggg cctggccggc ctgggcaacg tggggttgag caatgccggc    4320
agcaacaact gggggctggc caacctgggt gtgggcaaca tcgggttggc caacaccggc    4380
acgggcaaca tcgggatcgg gctggtcggc gactaccaga ccggcatcgg cggcctcaac    4440
tcgggtagtg gcaatatcgg attgttcaat tccggcaccg gcaatgtcgg gttcttcaac    4500
```

```
accggcaccg gcaacttcgg actgttcaac tccggtagtt tcaacaccgg catcggtaat   4560
agcggaaccg gcagtactgg gctcttcaat gccggcaatt tcaacaccgg catcgccaac   4620
cccgggtcgt acaacacggg cagcttcaat gtcggtgata ccaacaccgg tggtttcaac   4680
ccgggcgaca tcaacaccgg ctggttcaac accggcatta tgaatacggg cacccgcaac   4740
accggcgccc tcatgtcggg gaccgacagc aacggcatgc tgtggcgcgg cgaccacgag   4800
ggcctgttcg gcctgtccta tggcatcacg atcccgcaat tcccgatccg catcaccacg   4860
actggcggta tcggccccat cgtcatcccg gacaccacga tccttccgcc gctgcacctg   4920
cagatcaccg gcgacgcgga ctacagcttc accgtgcccg acatccccat ccccgccatc   4980
cacatcggca tcaatggcgt cgtcaccgtc ggcttcaccg ccccggaagc caccctgctg   5040
tccgccctga agaataacgg tagcttcatc agcttcggcc ccatcacgct ctcgaatatc   5100
gatattccgc ccatggattt cacgttaggc ctgcccgttc ttggtcctat cacgggccaa   5160
ctcggaccaa ttcatcttga gccaatcgtg gtggccggga tcggtgtgcc cctggagatc   5220
gagcccatcc ccctggatgc gatttcgttg agtgagtcga ttcctatccg catacctgtt   5280
gatattccgg cctcggtcat cgatgggatt tcaatgtcgg aagtggtgcc gatcgatgcg   5340
tccgtggaca tcccggcggt cacgatcaca ggcaccacca tttccgcgat cccgctgggc   5400
ttcgacattc gcaccagtgc cggacccctc aacatcccga tcatcgacat cccggcggcg   5460
ccgggcttcg ggaactcgac ccagatgccg tcgtcggggt tcttcaacac cggtgccggc   5520
ggcggatcgg gcatcggcaa cttgggtgcg ggcgtgtcgg gcctgctcaa ccaggccggc   5580
gcggggtcac tggtggggac actctcgggg ctgggcaatg ccggcaccct ggcctcgggt   5640
gtgctgaact ccggcaccgc catctccggg ctgttcaacg tgagcacgct ggacgccacc   5700
accccggcgg tgatctcggg gttcagcaac ctcggcgacc atatgtcggg ggtgtccatc   5760
gatggcctga tcgcgatcct caccttccca cctgccgagt ccgtgttcga tcagatcatc   5820
gacgcggcca tcgccgagct gcagcacctc gacatcggca acgctttggc cttgggcaat   5880
gtcgcggggt gaacctcgg tttggctaac gtcggtgagt tcaacctggg tgcgggcaac   5940
gtcggcaaca tcaacgtcgg cgccggcaac ctcggcggca gcaacttggg gttgggcaac   6000
gtcgggaccg gcaacctcgg gttcggcaac atcggtgccg gcaatttcgg attcggcaac   6060
gcgggcctga ccgcgggcgc ggggggcctg ggcaatgtgg ggttgggtaa cgccggcagc   6120
ggcagctggg ggttggccaa cgtgggtgtg ggcaatatcg ggttggccaa caccggcacc   6180
ggcaacatcg ggatcgggct gaccggggac tatcggaccg ggatcggcgg cctgaactcg   6240
ggcaccggga acctcggtt gttcaactcg ggcaccggca acatcgggtt cttcaacacc   6300
gggaccggga acttcgggct gttcaactcg ggcagttaca gcaccggtgt ggggaatgcg   6360
ggcacggcca gcaccggtt gttcaacgcg gggaacttca acaccggtct ggccaatgcc   6420
ggctcctaca acaccggcag cctcaacgtg ggcagcttca acaccggcgg cgtcaacccg   6480
ggcaccgtca acaccggctg gttcaacacc ggccacacca acaccggcct gttcaacacc   6540
ggcaacgtca acaccggcgc gttcaactcc ggcagcttca caacggggc gctgtggacc   6600 ggtgactacc acgggctggt cggcttctcc ttcagcatcg acatcgccgg cagcaccctg   6660
ctggacctca acgaaaccct caacctgggc cccatccaca tcgagcagat cgacatcccc   6720
ggcatgtcgc tgttcgacgt ccacgaaatc gtcgagatcg gacccttcac catcccgcag   6780
gtcgatgttc ccgcgatacc gctagagatc cacgaatcga tccacatgga tcccatcgtc   6840
ctggtgcccg ccaccacaat tcccgcacag acgagaacca ttccgctgga catccccgcc   6900
```

| | |
|---|---|
| tcacccgggt caaccatgac gcttccgctc atcagcatgc gcttcgaagg cgaggactgg | 6960 |
| atcctcgggt cgaccgcggc gattcccaat ttcggagacc ccttcccggc gcccacccag | 7020 |
| ggcatcacca ttcacaccgg ccctggcccc ggaacgaccg gcgagctcaa gatatctatt | 7080 |
| ccggggtttcg agattccgca aatcgctacc acgagattcc tgttggacgt gaacatcagc | 7140 |
| ggtggtctgc cggccttcac cttgttcgcg ggtggcctga cgatccccac gaacgccatc | 7200 |
| ccgttaacga tcgatgcgtc cggcgcgctg gatccgatca cgattttccc gggtgggtac | 7260 |
| acgatcgacc cgctgccgct gcacctggcg ctgaatctca ccgtgcccga cagcagcatc | 7320 |
| ccgatcatcg atgtcccgcc gacgccaggg ttcggcaaca ccacggcgac cccgtcgtcg | 7380 |
| gggttcttca actccggcgc cggtggggtg tcggggttcg gaaacgtcgg gtcgaacctg | 7440 |
| tcgggctggt ggaaccaggc ggcgagcgcg ctggcgggt cgggatcggg ggtgttgaat | 7500 |
| gtcggcacgc tgggctcggg tgtgctcaac gtcggctcgg gtgtctcggg gatctacaac | 7560 |
| accagcgtgt tgccgctcgg gacgccgcg gtgctgtcgg gcctcggcaa cgtcggccat | 7620 |
| cagctgtcgg gcgtgtctgc ggccgggacc gcgttgaacc agatccccat cctcaacatc | 7680 |
| gggttggcgg atgtgggcaa cttcaacgtc gggttcggca acgtcgggga cgttaacctg | 7740 |
| ggcgcggcca acctcggtgc gcaaaacctg gggctgggca acgtcggcac cggcaacctc | 7800 |
| ggcttcgcca acgtcggcca cggcaatatc ggtttcggca attcgggtct gaccgccggc | 7860 |
| gcggccggcc tgggcaacac ggggttcggc aatgccggca gcgccaacta tggtttcgcc | 7920 |
| aaccagggcg tgcgcaacat cgggttggcc aacaccggca ccggcaacat cgggatcggg | 7980 |
| ctggtggggg acaacctcac cggcatcggg ggcctgaact ccgtgccgg caatatcggc | 8040 |
| ttgttcaact ccggcaccgg caacatcggg ttcttcaact ccgggaccgg caacttcggc | 8100 |
| atcggtaact cgggcagctt caacaccggc atcggcaata gcggaacggg cagcactggg | 8160 |
| ctcttcaatg ccggcagctt caacaccggc gtggccaacg ccggcagcta caacaccggc | 8220 |
| agcttcaatg ccggcgacac caacaccggg gggttcaacc cgggcaccat caacaccggc | 8280 |
| tggttcaaca ccggccacac caataccggc atcgccaact cgggcaacgt cggcaccggc | 8340 |
| gcgttcatgt cgggcaactt cagcaacggc ctgttgtggc ggggtgatca cgagggcctg | 8400 |
| ttcagcctgt tctacagcct cgacgtgccc cggatcacca tcgtggacgc ccacctcgac | 8460 |
| ggcggcttcg gacccgtggt cctcccgccc atcccggtgc cggccgttaa tgcgcacctg | 8520 |
| accggaaacg tcgcgatggg cgcattcacc attccgcaga tcgacatccc cgcactcacc | 8580 |
| ccaaacatca ccggaagcgc cgccttccgc atcgttgtgg ggtccgtgcg cattccgccg | 8640 |
| gtgagtgtca ttgtggagca aataatcaac gcctcggttg gggcggagat gaggatagat | 8700 |
| cccttcgaaa tgtggactca aggcactaat ggccttggta taaccttcta ttcattcgga | 8760 |
| tcggccgacg ttcgcccta cgccaccggc ccactcgttt tcggcgccgg cacgagcgac | 8820 |
| ggaagccatc tcaccatttc cgcgtccagc ggggcgttta ccactccgca gctcgaaact | 8880 |
| ggcccgatca cgttgggctt ccaggtgccc ggcagcgtca acgcgatcac cctcttcccc | 8940 |
| ggtggtttga cgttcccggc gacctcgctg ctgaacctgg acgtgaccgc cggcgccggc | 9000 |
| ggcgtggaca tcccgccat cacctggccc gagatcgcgg cgagcgccga cggctcggtg | 9060 |
| tatgtcctcg ccagcagcat cccgctgatc aacatcccgc ccaccccggg cattgggaac | 9120 |
| agcaccatca ccccgtcgtc gggcttcttc aacgccggcg cgggcggggg atcgggcttc | 9180 |
| ggcaacttcg gcgcgggcac ctcgggctgg tggaaccagg cgcacaccgc gctggcgggg | 9240 |
| gcgggctcgg gttttgccaa cgttggcacg ctgcattccg gtgtgctcaa cctgggctcg | 9300 |

```
ggtgtctcgg ggatctacaa caccagcacg ctggggtgg ggaccccggc gctggtctca    9360
ggcctgggca acgtcggcca ccaactgtcg gggctgcttt ccggcgggtc cgcggtgaac    9420
ccggtgaccg ttctgaatat cgggttggcc aacgtcggca gccacaacgc cggtttcggc    9480
aatgtcgggg aggtcaacct gggcgcggcc aacctcggcg cgcacaacct gggcttcgga    9540
aatatcggcg ccggcaacct ggggttcggc aatattggcc acggcaatgt cggagtcggc    9600
aactcgggtc tgaccgcggg cgtgccgggc ctgggcaatg tggggttggg caatgccggc    9660
ggcaacaact gggggttggc caacgtgggc gtgggcaata tcgggttggc caacaccggc    9720
accggcaaca ttgggatcgg gctgaccggc gactaccaga ccggcatcgg cggcctaaat    9780
tccggtgccg gcaacctggg gttgttcaac tccggcgccg gcaacgtcgg gttcttcaac    9840
accgggaccg gcaacttcgg gttgttcaac tccggcagct tcaacaccgg cgtcggcaat    9900
agcggaacgg gcagcactgg gctcttcaat gccggcagtt tcaacaccgg tgtggccaac    9960 gccgcagct acaacacggg cagcttcaat gtcggtgaca ccaacaccgg gggcttcaac   10020
ccgggcagca tcaacaccgg ctggctcaac gccggcaacg ccaacaccgg ggtggccaac   10080
gcgggcaatg tcaacaccgg cgccttcgtc accggcaact tcagcaacgg catcctgtgg   10140
cgcggcgact accagggcct ggccggcttc gccgtgggct acaccctccc gctgttcccc   10200
gcggtgggcg ccgacgtcag cggcgggatc ggcccgatta ccgtgctgcc gcccatccac   10260
atcccgccca ttccggtcgg cttcgccgcg gtcggtggca tcggcccgat cgccatcccg   10320
gacatctctg ttccatccat tcacttgggc ctcgaccccg ccgtccatgt cggctccatc   10380
accgtcaacc ccattaccgt caggaccccg cccgtgctcg tcagttactc ccaaggagcc   10440
gtcaccagca cgtccggacc aacctcagag atttgggtca agcccagctt cttccccgga   10500
atccggatcg cgccctctag cggcgggggt gcaacgtcca cgcaaggggc atactttgtg   10560
gggcccatct ccatccccte cggcacggtg accttcccgg gattcaccat cccctcgac    10620 ccgatcgaca tcggcctgcc ggtgtcgctg accatcccgg ggttcaccat cccgggcggc   10680
accctgatcc ccaccctccc gctgggcctc gcgttgtcca atggcatccc gcccgtcgac   10740
atcccggcca tcgttctcga ccggatcttg ctggacctgc acgccgacac cactatcggc   10800
ccgatcaacg tcccgatcgc cgggttcggc ggggcgccgg gtttcgggaa ctcgaccacg   10860
ctgccgtcgt cgggcttctt caacaccgga gctggcggcg gttcgggctt tagcaacacc   10920
ggcgcgggca tgtcgggatt gctcaacgcg atgtcggatc cgctgctcgg gtcggcgtcg   10980
ggcttcgcca acttcggcac ccagctctcc ggcatcctca accgcggcgc cggcatctcg   11040
ggcgtgtaca acaccggcgc gctgggtgtt gtcaccgcgg ccgtcgtctc gggtttcggc   11100
aacgtcggcc agcaactgtc gggcttgctc ttcaccggcg tcgggccta a             11151
```

<210> SEQ ID NO 26
<211> LENGTH: 10
<212> TYPE: PRT
<213> ORGANISM: Mycobacterium tuberculosis

<400> SEQUENCE: 26

Ala Glu Met Lys Thr Asp Ala Ala Thr Leu
1               5                   10

<210> SEQ ID NO 27
<211> LENGTH: 10
<212> TYPE: PRT
<213> ORGANISM: Mycobacterium tuberculosis

```
<400> SEQUENCE: 27

Arg Ala Asp Glu Glu Gln Gln Gln Ala Leu
1               5                   10

<210> SEQ ID NO 28
<211> LENGTH: 10
<212> TYPE: PRT
<213> ORGANISM: Mycobacterium tuberculosis

<400> SEQUENCE: 28

Thr Ala Ala Gln Ala Ala Val Val Arg Phe
1               5                   10

<210> SEQ ID NO 29
<211> LENGTH: 8
<212> TYPE: PRT
<213> ORGANISM: Mycobacterium tuberculosis

<400> SEQUENCE: 29

Ala Glu Met Lys Thr Asp Ala Ala
1               5

<210> SEQ ID NO 30
<211> LENGTH: 11
<212> TYPE: PRT
<213> ORGANISM: Mycobacterium tuberculosis

<400> SEQUENCE: 30

Ala Glu Met Lys Thr Asp Ala Ala Thr Leu Ala
1               5                   10

<210> SEQ ID NO 31
<211> LENGTH: 9
<212> TYPE: PRT
<213> ORGANISM: Mycobacterium tuberculosis

<400> SEQUENCE: 31

Asn Ile Arg Gln Ala Gly Val Gln Tyr
1               5

<210> SEQ ID NO 32
<211> LENGTH: 9
<212> TYPE: PRT
<213> ORGANISM: Mycobacterium tuberculosis

<400> SEQUENCE: 32

Asn Ile Arg Gln Ala Gly Val Gln Tyr
1               5

<210> SEQ ID NO 33
<211> LENGTH: 9
<212> TYPE: PRT
<213> ORGANISM: Mycobacterium tuberculosis

<400> SEQUENCE: 33

Glu Met Lys Thr Asp Ala Ala Thr Leu
1               5

<210> SEQ ID NO 34
<211> LENGTH: 10
<212> TYPE: PRT
<213> ORGANISM: Mycobacterium tuberculosis

<400> SEQUENCE: 34

Ala Glu Met Lys Thr Asp Ala Ala Thr Leu
```

```
<210> SEQ ID NO 35
<211> LENGTH: 10
<212> TYPE: PRT
<213> ORGANISM: Mycobacterium tuberculosis

<400> SEQUENCE: 35

Ala Glu Met Lys Thr Asp Ala Ala Thr Leu
1               5                   10

<210> SEQ ID NO 36
<211> LENGTH: 9
<212> TYPE: PRT
<213> ORGANISM: Mycobacterium tuberculosis

<400> SEQUENCE: 36

Leu Leu Asp Ala His Ile Pro Gln Leu
1               5

<210> SEQ ID NO 37
<211> LENGTH: 9
<212> TYPE: PRT
<213> ORGANISM: Mycobacterium tuberculosis

<400> SEQUENCE: 37

Ala Ala His Ala Arg Phe Val Ala Ala
1               5

<210> SEQ ID NO 38
<211> LENGTH: 11
<212> TYPE: PRT
<213> ORGANISM: Mycobacterium tuberculosis

<400> SEQUENCE: 38

Ala Val Ile Asn Thr Thr Cys Asn Tyr Gly Gln
1               5                   10

<210> SEQ ID NO 39
<211> LENGTH: 95
<212> TYPE: PRT
<213> ORGANISM: Mycobacterium tuberculosis

<400> SEQUENCE: 39

Met Thr Glu Gln Gln Trp Asn Phe Ala Gly Ile Glu Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95

<210> SEQ ID NO 40
<211> LENGTH: 15
<212> TYPE: PRT
<213> ORGANISM: Mycobacterium tuberculosis

<400> SEQUENCE: 40
```

-continued

Met Thr Glu Gln Gln Trp Asn Phe Ala Gly Ile Glu Ala Ala Ala
1               5                   10                  15

<210> SEQ ID NO 41
<211> LENGTH: 15
<212> TYPE: PRT
<213> ORGANISM: Mycobacterium tuberculosis

<400> SEQUENCE: 41

Gln Trp Asn Phe Ala Gly Ile Glu Ala Ala Ala Ser Ala Ile Gln
1               5                   10                  15

<210> SEQ ID NO 42
<211> LENGTH: 15
<212> TYPE: PRT
<213> ORGANISM: Mycobacterium tuberculosis

<400> SEQUENCE: 42

Ala Gly Ile Glu Ala Ala Ala Ser Ala Ile Gln Gly Asn Val Thr
1               5                   10                  15

<210> SEQ ID NO 43
<211> LENGTH: 15
<212> TYPE: PRT
<213> ORGANISM: Mycobacterium tuberculosis

<400> SEQUENCE: 43

Ala Ala Ala Ser Ala Ile Gln Gly Asn Val Thr Ser Ile His Ser
1               5                   10                  15

<210> SEQ ID NO 44
<211> LENGTH: 15
<212> TYPE: PRT
<213> ORGANISM: Mycobacterium tuberculosis

<400> SEQUENCE: 44

Ala Ile Gln Gly Asn Val Thr Ser Ile His Ser Leu Leu Asp Glu
1               5                   10                  15

<210> SEQ ID NO 45
<211> LENGTH: 15
<212> TYPE: PRT
<213> ORGANISM: Mycobacterium tuberculosis

<400> SEQUENCE: 45

Asn Val Thr Ser Ile His Ser Leu Leu Asp Glu Gly Lys Gln Ser
1               5                   10                  15

<210> SEQ ID NO 46
<211> LENGTH: 15
<212> TYPE: PRT
<213> ORGANISM: Mycobacterium tuberculosis

<400> SEQUENCE: 46

Ile His Ser Leu Leu Asp Glu Gly Lys Gln Ser Leu Thr Lys Leu
1               5                   10                  15

<210> SEQ ID NO 47
<211> LENGTH: 16
<212> TYPE: PRT
<213> ORGANISM: Mycobacterium tuberculosis

<400> SEQUENCE: 47

Leu Asp Glu Gly Lys Gln Ser Leu Thr Lys Leu Ala Ala Ala Trp Gly
1               5                   10                  15

```
<210> SEQ ID NO 48
<211> LENGTH: 15
<212> TYPE: PRT
<213> ORGANISM: Mycobacterium tuberculosis

<400> SEQUENCE: 48

Lys Gln Ser Leu Thr Lys Leu Ala Ala Ala Trp Gly Gly Ser Gly
1               5                   10                  15

<210> SEQ ID NO 49
<211> LENGTH: 15
<212> TYPE: PRT
<213> ORGANISM: Mycobacterium tuberculosis

<400> SEQUENCE: 49

Thr Lys Leu Ala Ala Ala Trp Gly Gly Ser Gly Ser Glu Ala Tyr
1               5                   10                  15

<210> SEQ ID NO 50
<211> LENGTH: 15
<212> TYPE: PRT
<213> ORGANISM: Mycobacterium tuberculosis

<400> SEQUENCE: 50

Ala Ala Trp Gly Gly Ser Gly Ser Glu Ala Tyr Gln Gly Val Gln
1               5                   10                  15

<210> SEQ ID NO 51
<211> LENGTH: 15
<212> TYPE: PRT
<213> ORGANISM: Mycobacterium tuberculosis

<400> SEQUENCE: 51

Gly Ser Gly Ser Glu Ala Tyr Gln Gly Val Gln Gln Lys Trp Asp
1               5                   10                  15

<210> SEQ ID NO 52
<211> LENGTH: 15
<212> TYPE: PRT
<213> ORGANISM: Mycobacterium tuberculosis

<400> SEQUENCE: 52

Glu Ala Tyr Gln Gly Val Gln Gln Lys Trp Asp Ala Thr Ala Thr
1               5                   10                  15

<210> SEQ ID NO 53
<211> LENGTH: 15
<212> TYPE: PRT
<213> ORGANISM: Mycobacterium tuberculosis

<400> SEQUENCE: 53

Gly Val Gln Gln Lys Trp Asp Ala Thr Ala Thr Glu Leu Asn Asn
1               5                   10                  15

<210> SEQ ID NO 54
<211> LENGTH: 15
<212> TYPE: PRT
<213> ORGANISM: Mycobacterium tuberculosis

<400> SEQUENCE: 54

Lys Trp Asp Ala Thr Ala Thr Glu Leu Asn Asn Ala Leu Gln Asn
1               5                   10                  15

<210> SEQ ID NO 55
<211> LENGTH: 15
```

```
<212> TYPE: PRT
<213> ORGANISM: Mycobacterium tuberculosis

<400> SEQUENCE: 55

Thr Ala Thr Glu Leu Asn Asn Ala Leu Gln Asn Leu Ala Arg Thr
1               5                   10                  15

<210> SEQ ID NO 56
<211> LENGTH: 15
<212> TYPE: PRT
<213> ORGANISM: Mycobacterium tuberculosis

<400> SEQUENCE: 56

Leu Asn Asn Ala Leu Gln Asn Leu Ala Arg Thr Ile Ser Glu Ala
1               5                   10                  15

<210> SEQ ID NO 57
<211> LENGTH: 15
<212> TYPE: PRT
<213> ORGANISM: Mycobacterium tuberculosis

<400> SEQUENCE: 57

Leu Gln Asn Leu Ala Arg Thr Ile Ser Glu Ala Gly Gln Ala Met
1               5                   10                  15

<210> SEQ ID NO 58
<211> LENGTH: 15
<212> TYPE: PRT
<213> ORGANISM: Mycobacterium tuberculosis

<400> SEQUENCE: 58

Ala Arg Thr Ile Ser Glu Ala Gly Gln Ala Met Ala Ser Thr Glu
1               5                   10                  15

<210> SEQ ID NO 59
<211> LENGTH: 15
<212> TYPE: PRT
<213> ORGANISM: Mycobacterium tuberculosis

<400> SEQUENCE: 59

Ser Glu Ala Gly Gln Ala Met Ala Ser Thr Glu Gly Asn Val Thr
1               5                   10                  15

<210> SEQ ID NO 60
<211> LENGTH: 15
<212> TYPE: PRT
<213> ORGANISM: Mycobacterium tuberculosis

<400> SEQUENCE: 60

Gln Ala Met Ala Ser Thr Glu Gly Asn Val Thr Gly Met Phe Ala
1               5                   10                  15

<210> SEQ ID NO 61
<211> LENGTH: 99
<212> TYPE: PRT
<213> ORGANISM: Mycobacterium tuberculosis

<400> SEQUENCE: 61

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
                20                  25                  30

Glu Ser Thr Ala Gly Ser Leu Gln Gly Gln Trp Arg Gly Ala Ala Gly
        35                  40                  45
```

```
Thr Ala Ala Gln Ala Ala Val Val Arg Phe Gln Glu Ala Ala Asn Lys
        50                  55                  60

Gln Lys Gln Glu Leu Asp Glu Ile Ser Thr Asn Ile Arg Gln Ala Gly
 65                  70                  75                  80

Val Gln Tyr Ser Arg Ala Asp Glu Glu Gln Gln Ala Leu Ser Ser
                85                  90                  95

Gln Met Gly

<210> SEQ ID NO 62
<211> LENGTH: 15
<212> TYPE: PRT
<213> ORGANISM: Mycobacterium tuberculosis

<400> SEQUENCE: 62

Met Ala Glu Met Lys Thr Asp Ala Ala Thr Leu Ala Gln Glu Ala
 1               5                  10                  15

<210> SEQ ID NO 63
<211> LENGTH: 15
<212> TYPE: PRT
<213> ORGANISM: Mycobacterium tuberculosis

<400> SEQUENCE: 63

Lys Thr Asp Ala Ala Thr Leu Ala Gln Glu Ala Gly Asn Phe Glu
 1               5                  10                  15

<210> SEQ ID NO 64
<211> LENGTH: 15
<212> TYPE: PRT
<213> ORGANISM: Mycobacterium tuberculosis

<400> SEQUENCE: 64

Ala Thr Leu Ala Gln Glu Ala Gly Asn Phe Glu Arg Ile Ser Gly
 1               5                  10                  15

<210> SEQ ID NO 65
<211> LENGTH: 15
<212> TYPE: PRT
<213> ORGANISM: Mycobacterium tuberculosis

<400> SEQUENCE: 65

Gln Glu Ala Gly Asn Phe Glu Arg Ile Ser Gly Asp Leu Lys Thr
 1               5                  10                  15

<210> SEQ ID NO 66
<211> LENGTH: 15
<212> TYPE: PRT
<213> ORGANISM: Mycobacterium tuberculosis

<400> SEQUENCE: 66

Asn Phe Glu Arg Ile Ser Gly Asp Leu Lys Thr Gln Ile Asp Gln
 1               5                  10                  15

<210> SEQ ID NO 67
<211> LENGTH: 15
<212> TYPE: PRT
<213> ORGANISM: Mycobacterium tuberculosis

<400> SEQUENCE: 67

Ile Ser Gly Asp Leu Lys Thr Gln Ile Asp Gln Val Glu Ser Thr
 1               5                  10                  15

<210> SEQ ID NO 68
<211> LENGTH: 15
```

-continued

```
<212> TYPE: PRT
<213> ORGANISM: Mycobacterium tuberculosis

<400> SEQUENCE: 68

Leu Lys Thr Gln Ile Asp G

```
<400> SEQUENCE: 75

Ala Ala Val Val Arg Phe Gln Glu Ala Ala Asn Lys Gln Lys Gln
 1               5                  10                  15

<210> SEQ ID NO 76
<211> LENGTH: 15
<212> TYPE: PRT
<213> ORGANISM: Mycobacterium tuberculosis

<400> SEQUENCE: 76

Arg Phe Gln Glu Ala Ala Asn Lys Gln Lys Gln Glu Leu Asp Glu
 1               5                  10                  15

<210> SEQ ID NO 77
<211> LENGTH: 15
<212> TYPE: PRT
<213> ORGANISM: Mycobacterium tuberculosis

<400> SEQUENCE: 77

Ala Ala Asn Lys Gln Lys Gln Glu Leu Asp Glu Ile Ser Thr Asn
 1               5                  10                  15

<210> SEQ ID NO 78
<211> LENGTH: 15
<212> TYPE: PRT
<213> ORGANISM: Mycobacterium tuberculosis

<400> SEQUENCE: 78

Gln Lys Gln Glu Leu Asp Glu Ile Ser Thr Asn Ile Arg Gln Ala
 1               5                  10                  15

<210> SEQ ID NO 79
<211> LENGTH: 15
<212> TYPE: PRT
<213> ORGANISM: Mycobacterium tuberculosis

<400> SEQUENCE: 79

Leu Asp Glu Ile Ser Thr Asn Ile Arg Gln Ala Gly Val Gln Tyr
 1               5                  10                  15

<210> SEQ ID NO 80
<211> LENGTH: 15
<212> TYPE: PRT
<213> ORGANISM: Mycobacterium tuberculosis

<400> SEQUENCE: 80

Ser Thr Asn Ile Arg Gln Ala Gly Val Gln Tyr Ser Arg Ala Asp
 1               5                  10                  15

<210> SEQ ID NO 81
<211> LENGTH: 15
<212> TYPE: PRT
<213> ORGANISM: Mycobacterium tuberculosis

<400> SEQUENCE: 81

Arg Gln Ala Gly Val Gln Tyr Ser Arg Ala Asp Glu Glu Gln Gln
 1               5                  10                  15

<210> SEQ ID NO 82
<211> LENGTH: 15
<212> TYPE: PRT
<213> ORGANISM: Mycobacterium tuberculosis

<400> SEQUENCE: 82

Val Gln Tyr Ser Arg Ala Asp Glu Glu Gln Gln Gln Ala Leu Ser
```

-continued

```
<210> SEQ ID NO 83
<211> LENGTH: 15
<212> TYPE: PRT
<213> ORGANISM: Mycobacterium tuberculosis

<400> SEQUENCE: 83

Arg Ala Asp Glu Glu Gln Gln Gln Ala Leu Ser Ser Gln Met Gly
1               5                   10                  15

<210> SEQ ID NO 84
<211> LENGTH: 5
<212> TYPE: PRT
<213> ORGANISM: Artificial Sequence
<220> FEATURE:
<223> OTHER INFORMATION: peptide linker

<400> SEQUENCE: 84

Gly Gly Gly Gly Ser
1               5

<210> SEQ ID NO 85
<211> LENGTH: 9
<212> TYPE: PRT
<213> ORGANISM: Mycobacterium tuberculosis

<400> SEQUENCE: 85

Ala Ser Pro Val Ala Gln Ser Tyr Leu
1               5

<210> SEQ ID NO 86
<211> LENGTH: 10
<212> TYPE: PRT
<213> ORGANISM: Mycobacterium tuberculosis

<400> SEQUENCE: 86

Glu Leu Pro Gln Trp Leu Ser Ala Asn Arg
1               5                   10
```